United States Patent
Taniguchi et al.

(10) Patent No.: US 12,293,519 B2
(45) Date of Patent: May 6, 2025

(54) CELL EVALUATION METHOD, CELL EVALUATION SYSTEM AND PROGRAM

(71) Applicants: PUBLIC UNIVERSITY CORPORATION YOKOHAMA CITY UNIVERSITY, Kanagawa (JP); NIKON CORPORATION, Tokyo (JP)

(72) Inventors: Hideki Taniguchi, Yokohama (JP); Takanori Takebe, Yokohama (JP); Momotaro Ishikawa, Kamakura (JP); Masafumi Yamashita, Fujisawa (JP); Yasujiro Kiyota, Tokyo (JP)

(73) Assignees: PUBLIC UNIVERSITY CORPORATION YOKOHAMA CITY UNIVERSITY, Kanagawa (JP); NIKON CORPORATION, Tokyo (JP)

( * ) Notice: Subject to any disclaimer, the term of this patent is extended or adjusted under 35 U.S.C. 154(b) by 453 days.

(21) Appl. No.: 17/770,977

(22) PCT Filed: Nov. 2, 2020

(86) PCT No.: PCT/JP2020/041084
§ 371 (c)(1),
(2) Date: Aug. 24, 2022

(87) PCT Pub. No.: WO2021/085649
PCT Pub. Date: May 6, 2021

(65) Prior Publication Data
US 2023/0154003 A1    May 18, 2023

(30) Foreign Application Priority Data
Oct. 31, 2019 (JP) .................... 2019-198409

(51) Int. Cl.
G06T 7/00    (2017.01)
C12M 1/34    (2006.01)

(52) U.S. Cl.
CPC .......... G06T 7/0016 (2013.01); C12M 41/46 (2013.01); G06T 2207/30004 (2013.01)

(58) Field of Classification Search
CPC ........ G06T 7/0016; G06T 2207/30004; C12M 41/46
See application file for complete search history.

(56) References Cited

U.S. PATENT DOCUMENTS

2003/0095952 A1* 5/2003 Krause ................. C12N 5/0647
                                                               435/372
2012/0190059 A1    7/2012 Deng et al.
(Continued)

FOREIGN PATENT DOCUMENTS

EP    3196292 A1    7/2017
JP    2012-533310 A    12/2012
(Continued)

OTHER PUBLICATIONS

International Search Report mailed Jan. 19, 2021 for Application No. PCT/JP2020/041084, with English translation, 6 pages.
(Continued)

*Primary Examiner* — Myron Wyche
(74) *Attorney, Agent, or Firm* — Squire Patton Boggs (US) LLP

(57) ABSTRACT

A cell evaluation method includes acquiring a first evaluation index and a first index calculated using the first evaluation index with respect to comparative target cells in a culture process including a cell differentiation-inducing process in which cell differentiation is induced, calculating a second index on the basis of the first evaluation index with respect to evaluation target cells different from the comparative target cells, and evaluating differentiation of the evaluation target cells by comparing the first index with the second index.

14 Claims, 33 Drawing Sheets

(56) References Cited

U.S. PATENT DOCUMENTS

| | | | |
|---|---|---|---|
| 2013/0274124 A1 | 10/2013 | Bhatia et al. | |
| 2014/0289877 A1* | 9/2014 | Taniguchi et al. | |
| 2016/0237400 A1* | 8/2016 | Xian | A61K 35/30 |
| 2017/0191021 A1* | 7/2017 | Wakui | C12M 41/46 |
| 2018/0147242 A1 | 5/2018 | Miyajima et al. | |

FOREIGN PATENT DOCUMENTS

| | | |
|---|---|---|
| JP | 2015-514396 A | 5/2015 |
| WO | WO 2013/047639 A1 | 4/2013 |
| WO | WO 2016/042956 A1 | 3/2016 |
| WO | WO 2016/148216 A1 | 9/2016 |

OTHER PUBLICATIONS

Written Opinion of the International Searching Authority mailed Jan. 19, 2021 for Application No. PCT/JP2020/041084, with English translation, 8 pages.

Notice of Reasons for Refusal dated Oct. 29, 2024 for Japanese Patent Application No. 2021-553751; with English translation, 7 pages.

\* cited by examiner

ADHESION REGION AR3

DEAD CELL REGION AR4

DYING AND DEAD CELL REGION AR5

CELL EVALUATION METHOD, CELL EVALUATION SYSTEM AND PROGRAM

TECHNICAL FIELD

The present invention relates to a cell evaluation method, a cell evaluation system, and a program.

This application is a National Stage filing under 35 U.S.C. § 371 of International Patent Application No. PCT/JP2020/041084, filed Nov. 2, 2020, which claims the benefit of and priority to Japanese Patent Application No. 2019-198409, filed Oct. 31, 2019, the content of which is incorporated herein by reference.

BACKGROUND ART

In recent years, a differentiation-inducing method for differentiation of stem cells into differentiated cells has been established and technology for a stable cell culture process has become known. Patent Literature 1 describes technology related to a cell culture process using a method of inducing terminal differentiation of human functional cells based on tissue reconstruction (see Patent Literature 1). Here, the cell culture state is required to be evaluated using an index according to a cell type and each differentiation-inducing process.

CITATION LIST

Patent Literature

Patent Literature 1
PCT International Publication No. WO 2013/047639

SUMMARY OF INVENTION

According to a first aspect of the present invention, there is provided a cell evaluation method including: acquiring a first evaluation index and a first index calculated using the first evaluation index with respect to comparative target cells in a culture process including a cell differentiation-inducing process; calculating a second index on the basis of the first evaluation index with respect to evaluation target cells different from the comparative target cells; and evaluating differentiation of the evaluation target cells by comparing the first index with the second index.

According to a second aspect of the present invention, there is provided a cell evaluation system for evaluating cell differentiation in a culture process including a cell differentiation-inducing process, the cell evaluation system including: an acquisition unit configured to acquire a first evaluation index and a first index calculated using the first evaluation index with respect to comparative target cells; a calculation unit configured to calculate a second index on the basis of the first evaluation index with respect to evaluation target cells different from the comparative target cells; and an evaluation unit configured to evaluate differentiation of the evaluation target cells by comparing the first index with the second index.

According to a third aspect of the present invention, there is provided a program for evaluating cell differentiation in a culture process including a cell differentiation-inducing process, the program causing a computer to execute: an acquisition step of acquiring a first evaluation index and a first index calculated using the first evaluation index with respect to comparative target cells; a calculation step of calculating a second index on the basis of the first evaluation index with respect to evaluation target cells different from the comparative target cells; and an evaluation step of evaluating differentiation of the evaluation target cells by comparing the first index with the second index.

DESCRIPTION OF EMBODIMENTS

Regarding Mature Hepatocyte Culture Process

Figure 1:
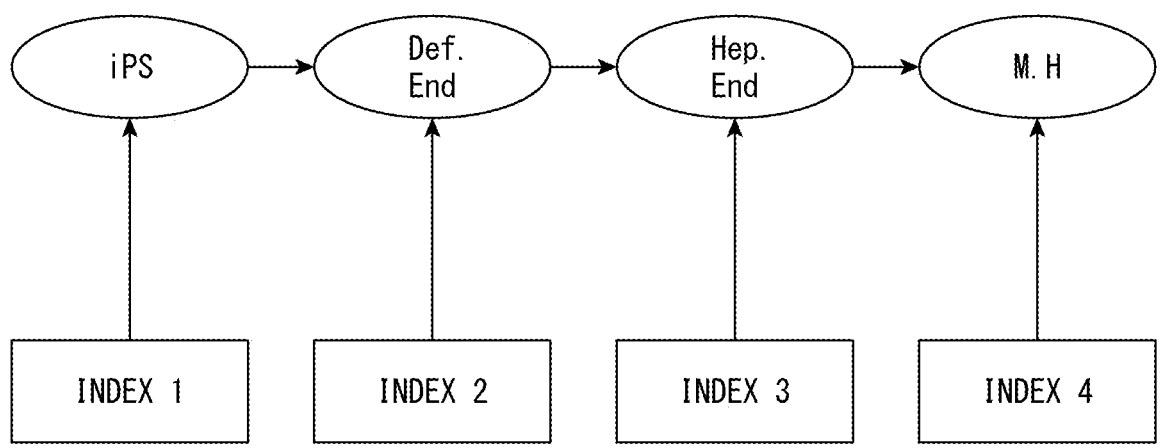
FIG. 1 is a schematic diagram showing an example of a culture process until differentiation of induced pluripotent stem (iPS) cells into mature hepatocytes is performed.

First, the differentiation of iPS cells into mature hepatocytes, which are an example of mature cells, will be described with reference to FIG. 1. FIG. 1 is a schematic diagram showing an example of a culture process from iPS cells to mature hepatocytes. As shown in FIG. 1, the iPS cells differentiate into the mature hepatocytes through a plurality of differentiation-inducing processes. Specifically, iPS cells differentiate into mature hepatocytes (M. H) via endoderm cells (Def. End) and hepatic endoderm cells (Hep. End). In the following description, a process of a period (for example, days 1 to 7) during which iPS cells differentiate into endoderm cells is referred to as a "first differentiation-inducing process," a process of a period (for example, days 8 to 10) during which the endoderm cells differentiate into hepatic endoderm cells is referred to as a "second differentiation-inducing process," a process of a period (for example, days 10 to 14) during which hepatic endoderm cells differentiate into mature hepatocytes is referred to as a "third differentiation-inducing process," and a process of a period (for example, days 15 to 21) during which mature hepatocytes mature appropriately is described as a "fourth differentiation-inducing process." Although cells to be cultured will be described as iPS cells as an example, the cells to be cultured are not limited to iPS cells and any stem cells having differentiation potency may be used. In addition to iPS cells, stem cells may be existing pluripotent stem cells such as embryonic stem (ES) cells and Muse cells, may be somatic stem cells (tissue stem cells or adult stem cells) capable of differentiating into a plurality of prescribed cell types, or may be unipotent stem cells that differentiate into a specific type of cells.

It is determined whether or not the above-described cells have differentiated in each differentiation-inducing process using an index according to each differentiation-inducing process. Here, for example, determining whether or not the cells have differentiated is also evaluating a differentiation progress state, so that it can be paraphrased as evaluating the differentiation. Also, for example, determining whether or not cells have differentiated is determining a degree of maturation of cells in each differentiation-inducing process, so that it can be rephrased as determining whether or not the cells have matured and determining the degree of maturity. For example, when it is determined that the present time is an appropriate time on the basis of index 1 with respect to the iPS cells that have been expanded and cultured, activin is added to a culture medium thereof. Thereby, the iPS cells are induced to differentiate into endoderm cells. Also, it is determined whether or not the endoderm cells have differentiated on the basis of index 2 according to the differentiation-inducing process for the endoderm cells. When it is determined that the cells have differentiated into endoderm cells, bone morphogenetic protein-4 (BMP-4) and fibroblast growth factor-2 (FGF-2) are added to the endoderm cells. Thereby, the endoderm cells are induced to differentiate into hepatic endoderm cells. Also, it is determined whether or not the hepatic endoderm cells have differentiated on the basis of index 3 according to the differentiation-inducing process for the hepatic endoderm cells. Also, it is determined whether or not the mature hepatocytes have differentiated on the basis of index 4 according to the differentiation-inducing process for the mature hepatocytes. Examples of these indices include a difference in color between a region where cells adhere to a culture vessel and a region where cells do not adhere to the culture vessel, a contrast between a cell membrane and cytoplasm, and the like. Also, the mature hepatocytes are, for example, hepatocytes in which an amount of albumin that has been produced is greater than or equal to a known standard.

In the conventional method, cells may be visually observed on the basis of these indices to determine whether or not the cells have differentiated. In this case, it may be difficult to perform an appropriate determination process depending on a proficiency level of a person making the determination. A case where the image determination device 10 of the present embodiment uses captured images captured in each differentiation process, determines whether the cells have differentiated on the basis of the index according to each captured image, and performs cell evaluation regardless of the proficiency level of the person making the determination will be described.

In the following description, a case where target cells that are evaluated (determined) by the image determination device 10 are hepatocytes will be described as an example. Also, the target cells that are evaluated (determined) by the image determination device 10 may be cells other than hepatocytes. In this case, the number of cell differentiation processes may be less than four or more than four. The target cells that are evaluated (determined) by the image determination device 10 may be, for example, existing cells such as somatic cells (nerve cells, blood cells, pancreatic cells, kidney cells, heart cells, and the like), germ cells, cancer cells, and the like.

First Embodiment

Figure 2:
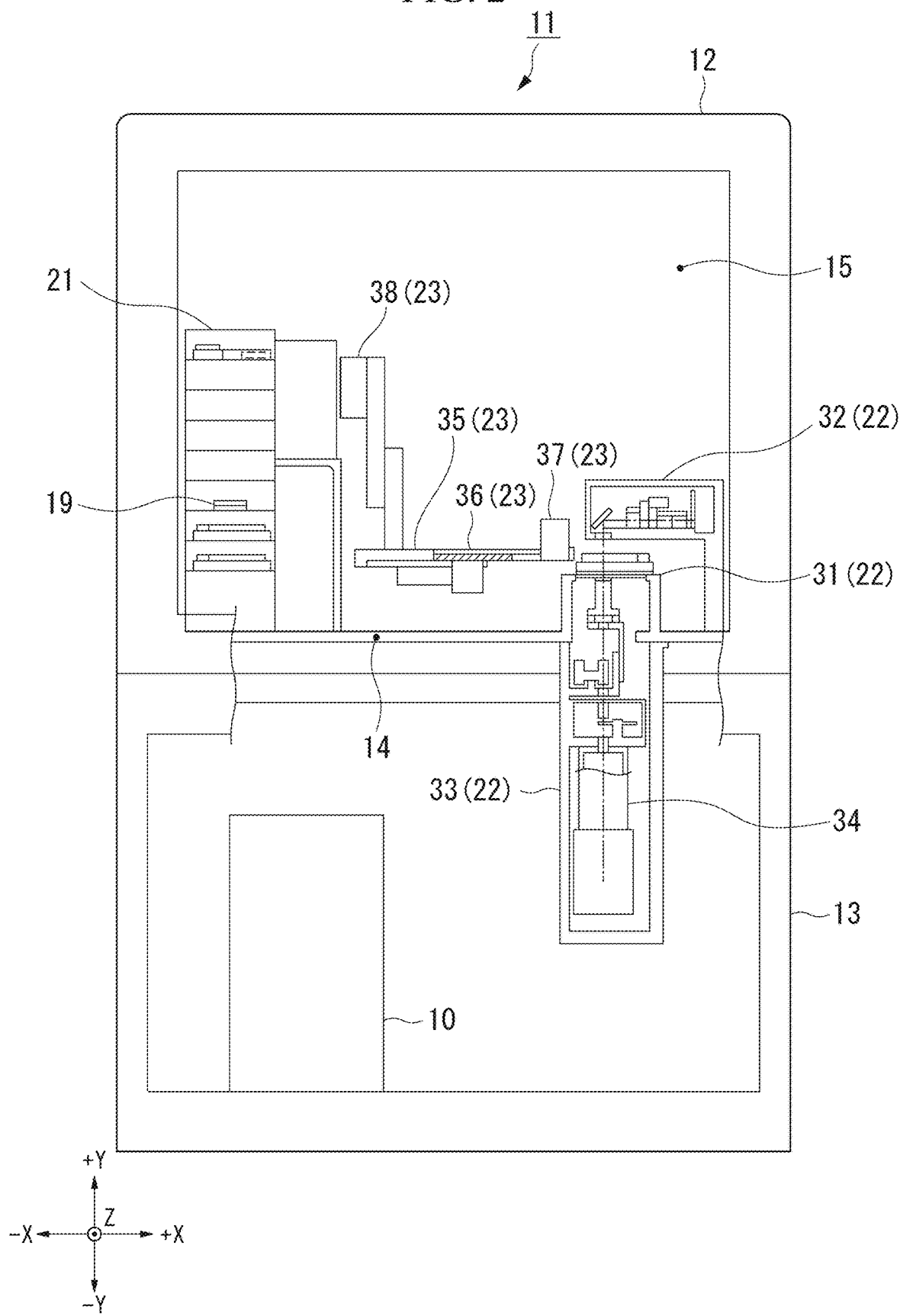
FIG. 2 is a front view of a culture observation device of the present embodiment.
Figure 3:
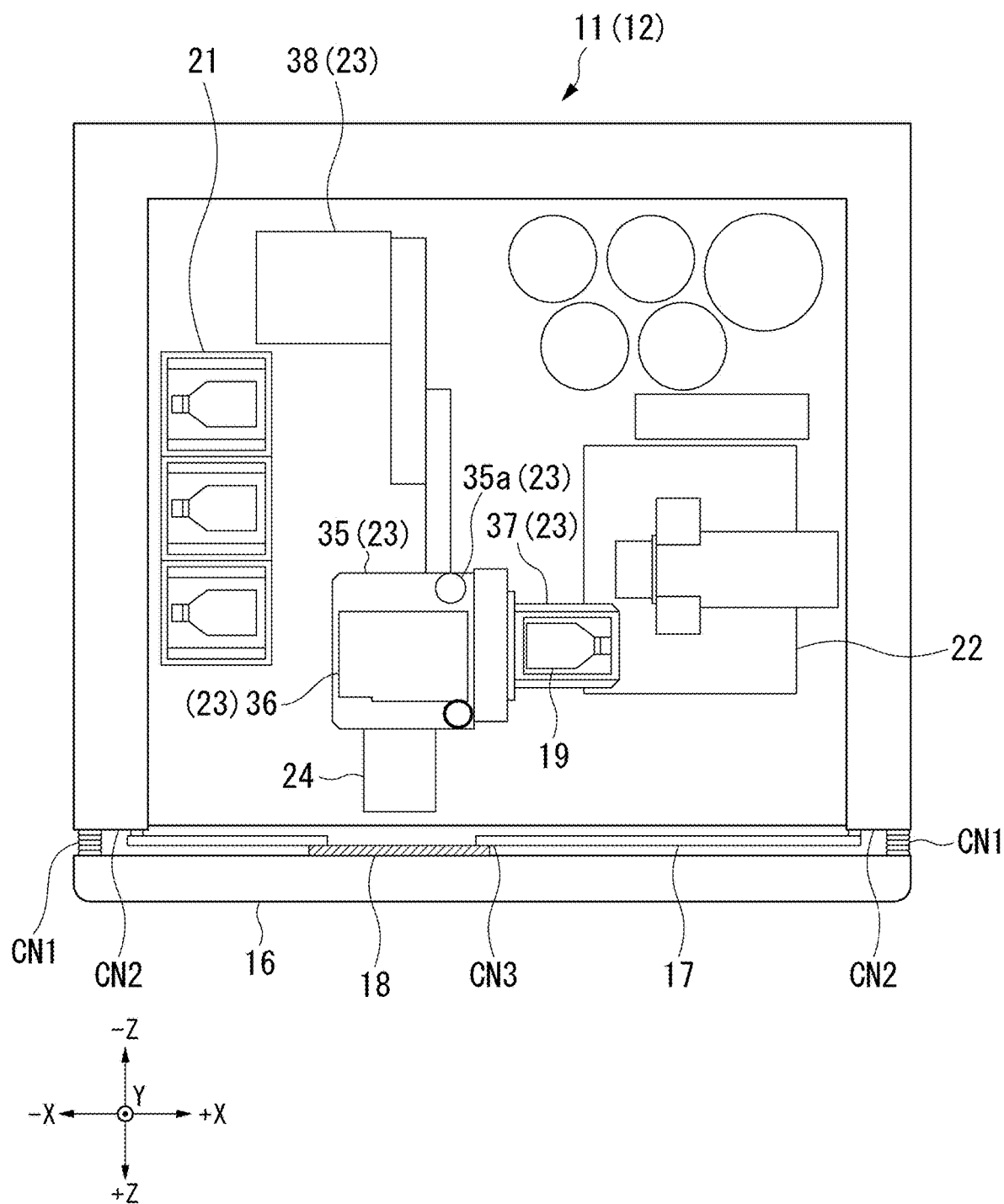
FIG. 3 is a plan view of the culture observation device of the present embodiment.

Hereinafter, a first embodiment of the present invention will be described with reference to the drawings. First, an overview of a culture observation device 11 in the present embodiment will be described with reference to FIGS. 2 and 3. FIG. 2 is a front view of the culture observation device 11 of the present embodiment. Also, FIG. 3 is a plan view of the culture observation device 11 of the present embodiment. Here, a +X-direction, a −X-direction, a +Y-direction, a −Y-direction, a +Z-direction, and a −Z-direction shown in FIGS. 2 and 3 are defined. As shown in FIG. 2, the +X-direction and the −X-direction are directions along a lateral direction of the culture observation device 11. The X-direction is opposite to the +X-direction. In the following description, the +X-direction is referred to as a "right" direction, the −X-direction is referred to as a "left" direction, and the +X-direction and the −X-direction are referred to as an "X-direction when they are not distinguished from each other. The +Y-direction and the −Y-direction are directions different from the X-direction (for example, substantially orthogonal thereto). The +Y-direction is a direction that becomes a normal line of an installation surface of the culture observation device 11. The −Y-direction is opposite to the +Y-direction. In the following description, the +Y-direction is referred to as an "upward" direction, the −Y-direction is referred to as a "downward" direction, and the +Y-direction and the −Y-direction are referred to as a "Y-direction" when they are not distinguished from each other. The +Z-direction and the −Z-direction are directions different from (for example, substantially orthogonal to) the X-direction and the Y-direction. The +Z-direction is a direction along a depth direction of the culture observation device 11. The −Z-direction is opposite to the +Z-direction. In the following description, the +Z-direction is referred to as a "front" or "forward" direction, the −Z-direction is referred to as a "back" or "backward" direction, and the +Z-direction and the −Z-direction are referred to as a "Z-direction" when they are not distinguished from each other.

As shown in FIGS. 2 and 3, the culture observation device 11 includes an upper casing 12 and a lower casing 13. The upper casing 12 and the lower casing 13 are arranged to be in contact with each other vertically via a base plate 14. The upper casing 12 internally includes a constant temperature compartment 15, a stocker 21, an observation unit 22, a vessel conveyance device 23, a conveyance table 24, and an image determination device 10.

There is an opening on a front surface of the constant temperature compartment 15 and this opening is covered with a large door 16, a middle door 17, and a small door 18. Specifically, the large door 16 covers the front surfaces of the upper casing 12 and the lower casing 13 and the middle door 17 covers the front surface of the upper casing 12. That is, the upper casing 12 has a double door of the large door 16 and the middle door 17. Thereby, the constant temperature compartment 15 is isolated from an external environment by the middle door 17 even if the large door 16 is opened. The small door 18 is a door for carrying in and out a culture vessel 19 for culturing cells and is attached to the middle door 17. Thereby, the culture vessel 19 can be carried in and out of the constant temperature room 15 via the small door 18. Also, it is possible to limit an environmental change of the constant temperature compartment 15 in the case where the small door 18 is opened as compared with the case where the middle door 17 is opened. Airtightness of the large door 16, the middle door 17, and the small door 18 is maintained by packings CN1, CN2, and CN3, respectively.

Also, a stocker 21, an observation unit 22, a vessel conveyance device 23, and a conveyance table 24 are disposed in the constant temperature compartment 15. Here, the conveyance table 24 is disposed in front of the small door 18 and the culture vessel 19 is carried in and out from the small door 18.

The stocker 21 is disposed on the left side within the constant temperature compartment 15. The stocker 21 has a plurality of shelves and a plurality of culture vessels 19 are stored in each shelf of the stocker 21. Also, in each culture vessel 19, culture target cells are accommodated together with a culture medium. Also, the culture vessel 19 is, for example, a well plate. The culture vessel 19 is not limited to the well plate and may be an existing culture vessel such as a flask or a dish.

The observation unit 22 is disposed so that it is fitted into the opening of the base plate 14. The observation unit 22 includes a sample table 31, a stand arm 32 protruding above the sample table 31, and a main body portion 33 in which a microscopic optical system (not shown) for phase difference observation and an imaging device 34 are embedded. Within the observation unit 22, the sample table 31 and the stand arm 32 are disposed in the constant temperature compartment 15 and the main body portion 33 is accommodated within the lower casing 13. The observation unit 22 performs time-lapse observation of the cells within the culture vessel 19. Details of the time-lapse observation will be described below.

The sample table 31 is made of a translucent material and the culture vessel 19 can be placed on the sample table 31. The sample table 31 is configured to be movable in the horizontal direction and the position of the culture vessel 19 placed on the upper surface can be adjusted. Also, an LED light source (not shown) and an illumination ring diaphragm (not shown) are provided on the stand arm 32 and a light intensity distribution of illumination light from the LED light source with which the sample table 31 is irradiated can be variably adjusted. Also, a condenser lens, an objective lens, a phase plate, and the like are provided on the microscopic optical system (not shown) and the microscopic optical system (not shown) is configured as in an optical system of a known phase contrast microscope. That is, the observation unit 22 functions as a phase contrast microscope. The imaging device 34 acquires a microscopic image of cells by imaging the cells of the culture vessel 19 transmitted and illuminated from above the sample table 31 by the stand arm 32 via the optical system of the microscope. Also, this microscopic image is, for example, a phase difference image in which a phase shift of light is detected as a contrast.

The vessel conveyance device 23 has a vertical robot 38 having an articulated arm, a rotary stage 35, a mini-stage 36, and an arm portion 37. The rotary stage 35 is attached to the tip of the vertical robot 38 so that it is rotatable 180° in the horizontal direction via the rotary shaft 35a. Thus, in the rotary stage 35, the arm portion 37 can be made to face the stocker 21, the sample table 31, and the conveyance table 24, respectively. The mini-stage 36 is slidably attached to the rotary stage 35 in the horizontal direction. The arm portion 37 for gripping the culture vessel 19 is attached to the mini-stage 36. Thereby, the vessel conveyance device 23 conveys the culture vessel 19 between the stocker 21, the sample table 31, and the conveyance table 24.

Regarding Image Determination Device 10

Figure 4:
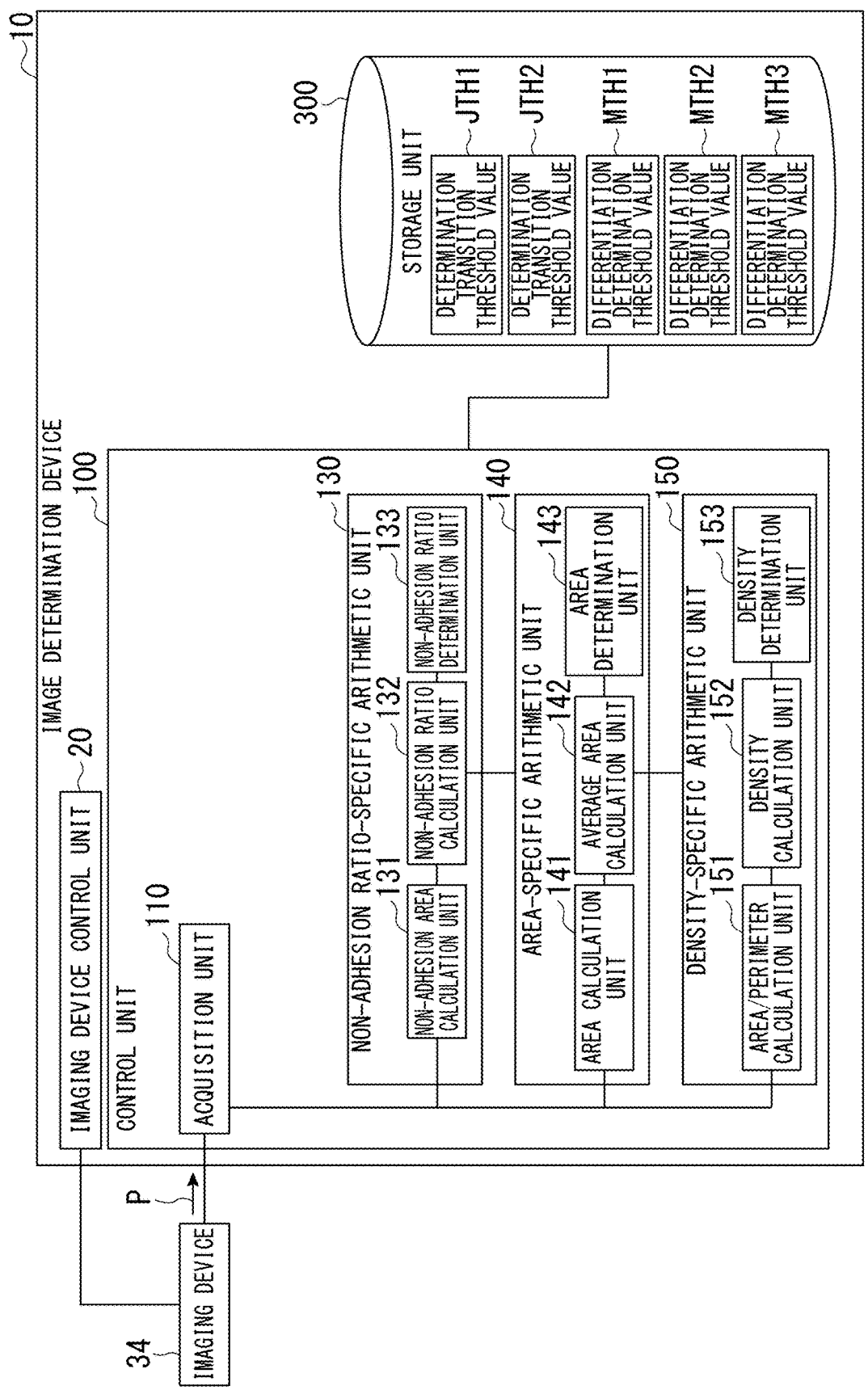
FIG. 4 is a diagram showing an example of a configuration of an image determination device according to a first embodiment.

FIG. 4 is a diagram showing an example of a configuration of the image determination device 10 according to the first embodiment. The image determination device 10 implements the imaging device control unit 20 and the control unit 100 as functional units when a hardware processor such as a central processing unit (CPU) executes a program (software) stored in the storage unit. Some or all of the components of the image determination device 10 may be implemented by hardware such as a large-scale integration (LSI) circuit, an application-specific integrated circuit (ASIC), a field-programmable gate array (FPGA), or a graphics processing unit (GPU) or may be implemented by software and hardware in cooperation. The storage unit 300 is implemented by, for example, a read-only memory (ROM), a flash memory, a secure digital (SD) card, a random access memory (RAM), a register, or the like.

The imaging device control unit 20 controls, for example, the vessel conveyance device 23 at prescribed time intervals, places the culture vessel 19 within the stocker 21 on the sample table 31, and causes the cells within the culture vessel 19 to be imaged by the imaging device 34. Thereby, the cells within the culture vessel 19 are time-lapse observed. The control unit 100 executes a process of determining whether or not the cells have differentiated on the basis of a captured image obtained by capturing the cells within the culture vessel 19 by the imaging device 34.

Also, the imaging device control unit 20 may be provided separately instead of the configuration provided in the image determination device 10. In this case, the imaging device control unit 20 and the image determination device 10 are connected so that information can be transmitted and received and the imaging device control unit 20 supplies the image of the cells captured by the imaging device 34 to the image determination device 10. Also, the image determination device 10 may have a configuration in which it is determined whether or not cells shown in an image have differentiated on the basis of the image of the cells acquired in another method instead of a configuration in which it is determined whether or not the cells within the culture vessel 19 have differentiated on the basis of the image of the cells captured by the imaging device 34 provided in the culture observation device 11. In this case, the image determination device 10 may not be provided within the culture observation device 11.

The imaging device 34 images the cells being cultured in the culture medium with the elapse of time. Specifically, the imaging device 34 captures an image P, which is an image of cells containing the culture medium, with the elapse of time. The imaging device 34 supplies the captured image P to the image determination device 10. For convenience of description, the image is an image itself output by the output unit 230 (the display device) to be described below and also represents data (image data) of the image. Here, the image data is, for example, data based on a signal intensity of each pixel of the imaging device 34.

First Differentiation-Inducing Process

Figure 5:
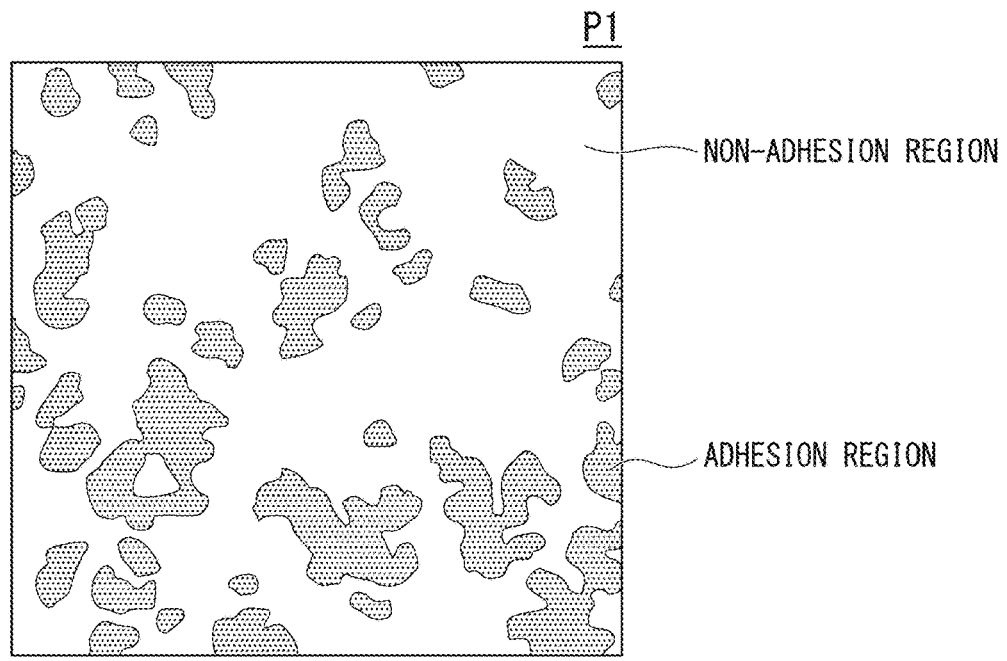
FIG. 5 is a schematic diagram showing an example of a first differentiation-inducing process image.

Hereinafter, an example of the image P captured in the first differentiation-inducing process will be described with reference to FIG. 5. FIG. 5 is a schematic diagram showing an example of a first differentiation-inducing process image P1. The first differentiation-inducing process image P1 is an image in which a culture medium containing cells in the first differentiation-inducing process is imaged among a plurality of images P. As shown in FIG. 5, in the first differentiation-inducing process, there are a location where cells adhere and a location where cells do not adhere. Here, the term "cells adhere" indicates that cells adhere to a culture vessel. The image determination device 10 determines whether or not the cells have differentiated on the basis of a non-adhesion ratio UBR in the first differentiation-inducing process. Here, the non-adhesion ratio UBR is a ratio of an area where the cells do not adhere to an area of the culture medium in which the cells are cultured. In the first differentiation-inducing process, the non-adhesion ratio UBR increases as the time elapsed after the cells were cultured decreases and the non-adhesion ratio UBR decreases as the time elapsed after the cells were cultured increases. That is, the non-adhesion ratio UBR decreases as the cell differentiation progresses.

Also, the culture vessel is provided with, for example, a layer (for example, a substrate (matrix), an extracellular matrix, an intercellular matrix, or the like) that serves as a scaffold for cells on the surface (the bottom surface) of the culture vessel so that cells can easily adhere thereto. Therefore, the term "cells adhere" also includes a case where cells adhere to the culture vessel via the substrate. In the following description, a case where "cells adhere to the culture vessel" and a case where "cells adhere to the culture vessel via the substrate" are collectively referred to as the case where "cells adhere."

Second Differentiation-Inducing Process

Figure 6:
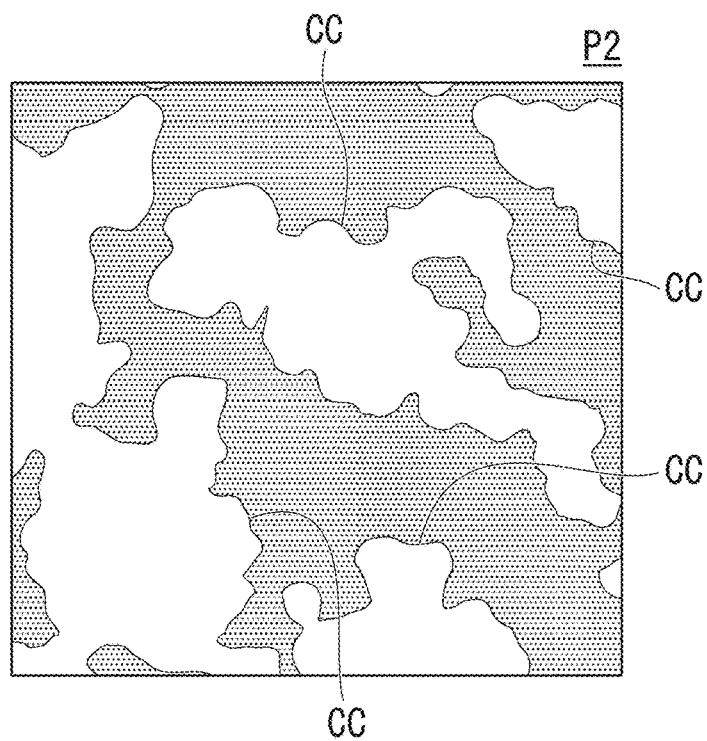
FIG. 6 is a schematic diagram showing an example of a second differentiation-inducing process image.

Next, an example of an image P captured in the second differentiation-inducing process will be described with reference to FIG. 6. FIG. 6 is a schematic diagram showing an example of the second differentiation-inducing process image P2. The second differentiation-inducing process image P2 is an image in which a culture medium containing cells in the second differentiation-inducing process is imaged among a plurality of images P. As shown in FIG. 6, in the second differentiation-inducing process, there are a plurality of cell clusters CC in which cells are clustered. Here, the cell cluster CC is, for example, a colony. The image determination device 10 determines whether or not the cells have differentiated on the basis of an average area CAA in the second differentiation-inducing process. Here, the average area CAA is an average of areas of the cell clusters CC present in the culture medium. In the second differentiation-inducing process, the average area CAA increases as the time elapsed after the cells were cultured decreases and the average area CAA decreases as the time elapsed after the cells were cultured increases.

Third Differentiation-Inducing Process

Figure 7:
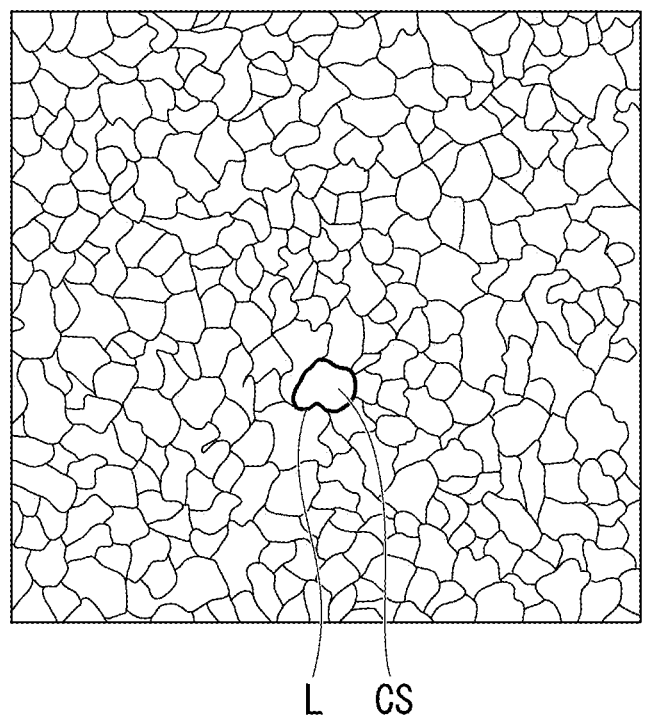
FIG. 7 is a schematic diagram showing an example of a third differentiation-inducing process image.

Next, an example of an image P captured in a third differentiation-inducing process will be described with reference to FIG. 7. FIG. 7 is a schematic diagram showing an example of a third differentiation-inducing process image P3. The third differentiation-inducing process image P3 is an image in which a culture medium containing cells in the third differentiation-inducing process is imaged among a plurality of images P. As shown in FIG. 7, in the third differentiation-inducing process, there are a plurality of cells having an area smaller than the area of the cell cluster CC. The image determination device 10 determines whether or not the cells have differentiated on the basis of a density CPT in the third differentiation-inducing process. Here, the density CPT is a ratio of a perimeter of a certain cell (a cell perimeter L shown in FIG. 7) to a cell area of the certain cell (a cell area CS shown in FIG. 7). The density CPT becomes higher when the cells become more elliptical and becomes lower when the cells become closer to a circle. Also, in the third differentiation-inducing process, the cells become circular as they mature. That is, the density CPT increases as the time elapsed after the cells were cultured decreases and the density CPT decreases as the time elapsed after the cells were cultured increases.

In this example, cells differentiate through the differentiation-inducing processes in the order of the first differentiation-inducing process, the second differentiation-inducing process, and the third differentiation-inducing process. That is, the imaging device 34 captures the images P in the order of the first differentiation-inducing process image P1, the second differentiation-inducing process image P2, and the third differentiation-inducing process image P3. Also, the imaging device 34 supplies the images P captured in the order of the first differentiation-inducing process image P1, the second differentiation-inducing process image P2, and the third differentiation-inducing process image P3 to the image determination device 10.

Regarding Differentiation Determination Threshold Value MTH and Determination Transition Threshold Value JTH Returning to FIG. 4, the image determination device 10 includes a control unit 100 and a storage unit 300. The storage unit 300 stores a determination transition threshold value JTH1, a determination transition threshold value JTH2, a differentiation determination threshold value MTH1, a differentiation determination threshold value MTH2, and a differentiation determination threshold value MTH3. The differentiation determination threshold value MTH is an index according to each differentiation-inducing process and is a threshold value indicating a degree of differentiation when it is determined whether or not cells have differentiated. Therefore, the differentiation determination threshold value MTH1 is an index used when it is determined whether or not cells have differentiated in the first differentiation-inducing process, and is a value indicating a prescribed non-adhesion ratio UBR. The differentiation determination threshold value MTH2 is an index used when it is determined whether or not cells have differentiated in the second differentiation-inducing process, and is a value indicating a prescribed average area CAA. Also, the differentiation determination threshold value MTH3 is an index used when it is determined whether or not cells have differentiated in the third differentiation-inducing process, and is a value indicating a prescribed density CPT.

Here, preferably, the image determination device 10 determines whether or not cells have differentiated using an appropriate index among the differentiation determination threshold values MTH1 to MTH3 at an appropriate time in accordance with the degree of cell differentiation. The determination transition threshold value JTH is a threshold value indicating whether or not the transition to the determination based on the index (i.e., the differentiation determination threshold values MTH2 to MTH3) according to the next differentiation-inducing process is possible when a determination process based on an index (any one of the differentiation determination threshold values MTH1 to MTH3 in the present example) according to a certain differentiation-inducing process is performed in the differentiation-inducing process. The determination transition threshold value JTH1 is a threshold value indicating whether or not the transition to the determination based on the differentiation determination threshold value MTH2 in the second differentiation-inducing process is possible when the determination process based on the differentiation determination threshold value MTH1 is performed in the first differentiation-inducing process and is a value indicating a prescribed non-adhesion ratio UBR. The determination transition threshold value JTH2 is a threshold value indicating whether or not the transition to the determination based on the differentiation determination threshold value MTH3 in the third differentiation-inducing process is possible when the determination process based on the differentiation determination threshold value MTH2 is performed in the second differentiation-inducing process and is a value indicating a prescribed average area CAA.

That is, in the cell evaluation method using the image determination device 10, when a magnitude relationship between the second index and the first index has changed, a second evaluation index and a third index calculated using the second evaluation index are acquired with respect to comparative target cells, a fourth index calculated using the second evaluation index is acquired with respect to evaluation target cells, and differentiation of the evaluation target cells is evaluated by comparing the third index with the fourth index.

Regarding Control Unit 100

The control unit 100 includes an acquisition unit 110, a non-adhesion ratio-specific arithmetic unit 130, an area-specific arithmetic unit 140, and a density-specific arithmetic unit 150 as its functional units. The acquisition unit 110 acquires an image P captured by the imaging device 34. The acquisition unit 110 supplies the acquired image P to the non-adhesion ratio-specific arithmetic unit 130, the area-specific arithmetic unit 140, and the density-specific arithmetic unit 150. Specifically, the acquisition unit 110 supplies the first differentiation-inducing process image P1 among images P acquired from the imaging device 34 to the non-adhesion ratio-specific arithmetic unit 130. The acquisition unit 110 supplies the second differentiation-inducing process image P2 among the images P acquired from the imaging device 34 to the area-specific arithmetic unit 140. The acquisition unit 110 supplies the third differentiation-inducing process image P3 among the images P acquired from the imaging device 34 to the density-specific arithmetic unit 150.

Regarding Non-Adhesion Ratio-Specific Arithmetic Unit 130

The non-adhesion ratio-specific arithmetic unit 130 includes a non-adhesion area calculation unit 131, a non-adhesion ratio calculation unit 132, and a non-adhesion ratio determination unit 133.

The non-adhesion area calculation unit 131 acquires the first differentiation-inducing process image P1 from the acquisition unit 110. The non-adhesion area calculation unit 131 extracts a non-adhesion portion image UBP, which is an image of the non-adhesion portion in which cells do not adhere to the culture vessel, from the acquired first differentiation-inducing process image P1. Also, the non-adhesion area calculation unit 131 extracts a culture medium image CMP, which is an image of the culture medium portion, from the acquired first differentiation-inducing process image P1. The non-adhesion area calculation unit 131 supplies the extracted non-adhesion portion image UBP and the culture medium image CMP to the non-adhesion ratio calculation unit 132.

The non-adhesion ratio calculation unit 132 acquires the non-adhesion portion image UBP and the culture medium image CMP from the non-adhesion area calculation unit 131. The non-adhesion ratio calculation unit 132 calculates a non-adhesion area UBS, which is an area of the non-adhesion portion where cells do not adhere to the culture vessel, on the basis of the acquired non-adhesion portion image UBP. Also, the non-adhesion ratio calculation unit 132 calculates an image-specific culture medium area CMS, which is an area of the culture medium contained in the captured image P, on the basis of the acquired culture medium image CMP. The non-adhesion ratio calculation unit 132 calculates the non-adhesion ratio UBR on the basis of the calculated non-adhesion area UBS and the calculated image-specific culture medium area CMS. In this example, a case where the non-adhesion ratio UBR is a value obtained by dividing the non-adhesion area UBS by the image-specific culture medium area CMS will be described. The non-adhesion ratio calculation unit 132 supplies the calculated non-adhesion ratio UBR to the non-adhesion ratio determination unit 133 and the area-specific arithmetic unit 140.

The non-adhesion ratio determination unit 133 determines whether or not cells have differentiated in the first differentiation-inducing process. The non-adhesion ratio determination unit 133 acquires the non-adhesion ratio UBR from the non-adhesion ratio calculation unit 132. The non-adhesion ratio determination unit 133 determines whether or not cells have differentiated in the first differentiation-inducing process on the basis of the acquired non-adhesion ratio UBR and the differentiation determination threshold value MTH1. In this example, the non-adhesion ratio determination unit 133 determines that cells have differentiated when the non-adhesion ratio UBR is less than the differentiation determination threshold value MT1.

The non-adhesion ratio determination unit 133 determines whether or not cells have differentiated after a point in time when the cells started to be cultured in the culture medium. That is, the non-adhesion ratio determination unit 133 determines whether or not cells have differentiated in the first differentiation-inducing process. Also, the non-adhesion ratio determination unit 133 ends the determination based on the non-adhesion ratio UBR and the differentiation determination threshold value MTH1 when the non-adhesion ratio UBR is less than the determination transition threshold value JTH1 on the basis of the non-adhesion ratio UBR and the determination transition threshold value JTH1. In other words, the non-adhesion ratio determination unit 133 determines whether or not cells have differentiated on the basis of the non-adhesion ratio UBR and the differentiation determination threshold value MTH1 until the non-adhesion ratio UBR is less than the determination transition threshold value JTH1 from the start of the cell culture process in the culture medium.

Figure 8:
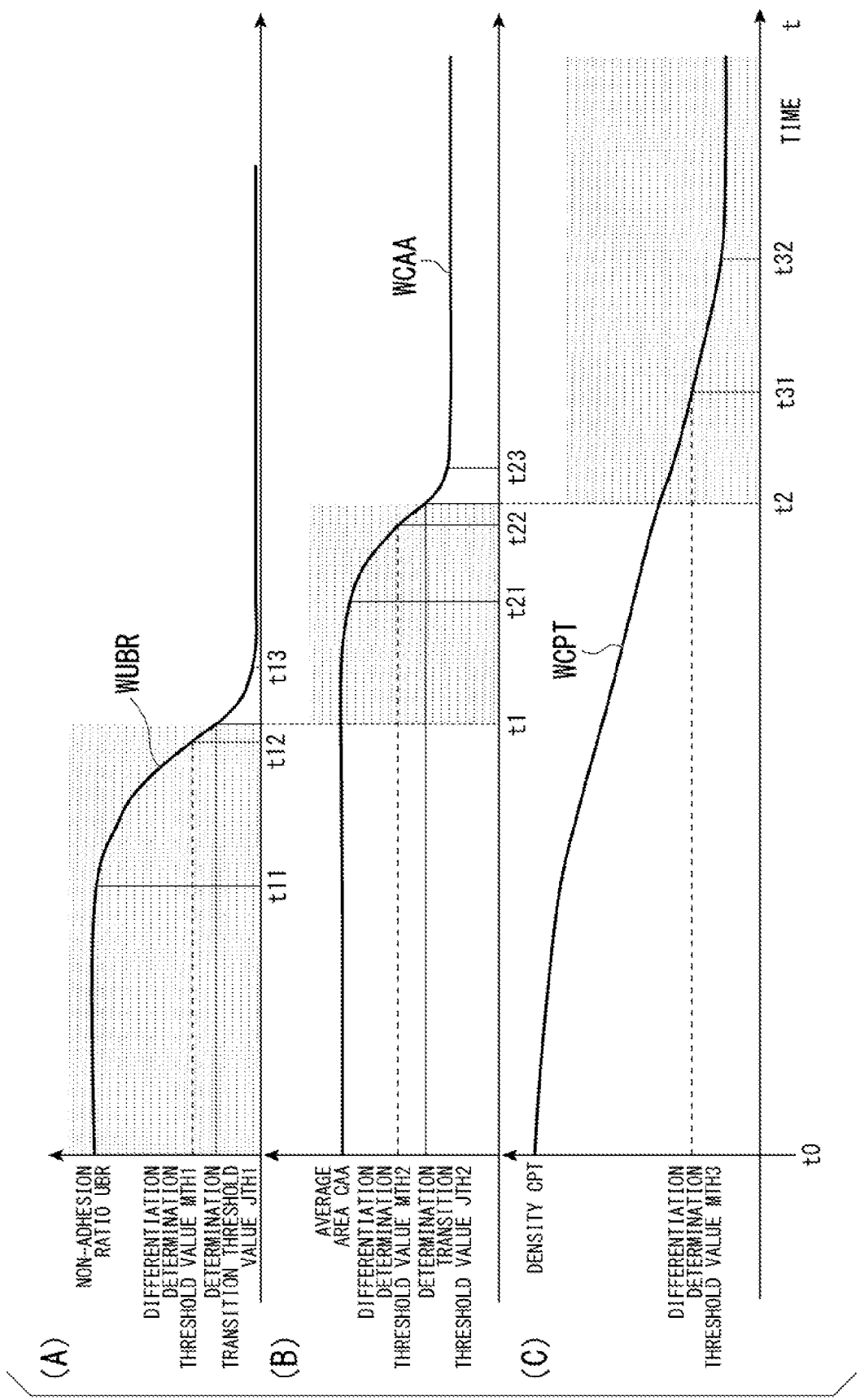
FIG. 8 is a graph showing an example of a determination process of a determination unit according to the first embodiment.

Hereinafter, the determination process of the non-adhesion ratio determination unit 133 will be described with reference to FIG. 8. FIG. 8 is a graph showing an example of a determination process of the determination unit according to the first embodiment. FIG. 8(A) shows a graph of a change over time in the non-adhesion ratio UBR. In FIG. 8(A), the vertical axis represents a non-adhesion ratio UBR and the horizontal axis represents time. Also, time t0 here indicates a time when the cells started to be cultured in the culture medium. In FIG. 8(A), a change over time in the non-adhesion ratio UBR is indicated by a waveform WUBR. Also, in FIG. 8(A), change points of the non-adhesion ratio UBR according to time transition are referred to as time t11, time t12, and time t13, respectively. In this example, a case where the waveform WUBR indicating the non-adhesion ratio UBR shows a constant value from time t0 to time t11, decreases from time t12 to time t13, and shows a constant value at time t13 will be described.

As shown in FIG. 8(A), the non-adhesion ratio calculation unit 132 determines whether or not cells in the first differentiation-inducing process have differentiated from time t0. Also, as shown in FIG. 8(A), at time t12, the waveform WUBR indicating the non-adhesion ratio UBR calculated by the non-adhesion ratio calculation unit 132 is less than the differentiation determination threshold value MTH1. That is, at time t12, it is shown that the area where the cells adhere to the culture vessel is larger than that at the start of the culture process. That is, the non-adhesion ratio determination unit 133 determines that the cells in the first differentiation-inducing process have differentiated at time t12.

Also, as shown in FIG. 8(A), at time t1, the waveform WUBR indicating the non-adhesion ratio UBR calculated by the non-adhesion ratio calculation unit 132 is less than the determination transition threshold value JTH1. That is, the non-adhesion ratio determination unit 133 determines whether or not cells have differentiated from time to to time t1.

Regarding Area-Specific Arithmetic Unit 140

Next, the area-specific arithmetic unit 140 will be described with reference to FIG. 4. The area-specific arithmetic unit 140 includes an area calculation unit 141, an average area calculation unit 142, and an area determination unit 143. The area calculation unit 141 acquires the second differentiation-inducing process image P2 from the acquisition unit 110. The area calculation unit 141 extracts a cell cluster image CCP, which is an image of a portion of a cell cluster CC, from the acquired second differentiation-inducing process image P2. In this example, the second differentiation-inducing process image P2 includes a plurality of imaged cell clusters CC. The area calculation unit 141 supplies the plurality of cell cluster images CCP that have been extracted to the average area calculation unit 142.

The average area calculation unit 142 acquires a plurality of cell cluster images CCP from the area calculation unit 141. The average area calculation unit 142 calculates a cell cluster area CSS, which is an area of the cell cluster CC, on the basis of the plurality of cell cluster images CCP that have been acquired. In this example, the average area calculation unit 142 calculates an average area CAA, which is an average value of a plurality of cell cluster areas CSS calculated on the basis of a plurality of cell cluster images CCP that have been acquired. The average area calculation unit 142 supplies the calculated average area CAA to the area determination unit 143 and the density-specific arithmetic unit 150.

The area determination unit 143 determines whether or not cells have differentiated in the second differentiation-inducing process. Specifically, the area determination unit 143 acquires the average area CAA from the average area calculation unit 142. The area determination unit 143 determines whether or not cells have differentiated in the second differentiation-inducing process on the basis of the acquired average area CAA and the differentiation determination threshold value MTH2. In this example, the area determination unit 143 determines that cells have differentiated when the average area CAA is less than the differentiation determination threshold value MTH2.

The area-specific arithmetic unit 140 acquires the non-adhesion ratio UBR from the non-adhesion ratio calculation unit 132. The area calculation unit 141 starts the calculation of the average area CAA when the non-adhesion ratio UBR is less than the determination transition threshold value JTH1. The area determination unit 143 starts the determination after the non-adhesion ratio determination unit 133 ends the determination process for the cells based on the non-adhesion ratio UBR and the differentiation determination threshold value MTH1. Also, the area determination unit 143 determines whether or not cells have differentiated on the basis of the calculated average area CAA and the differentiation determination threshold value MTH2. Also, when the calculated average area CAA is less than the determination transition threshold value JTH2, the area determination unit 143 ends the determination process for the cells based on the average area CAA and the differentiation determination threshold value MTH2. That is, the area determination unit 143 determines whether or not cells have differentiated on the basis of the average area CAA and the differentiation determination threshold value MTH2 until the average area CAA is less than the determination transition threshold value JTH2 after the transition from the first differentiation-inducing process to the second differentiation-inducing process.

Hereinafter, the determination process of the area determination unit 143 will be described with reference to FIG. 8. In FIG. 8(B), a graph of a change over time in the average area CAA is shown. In FIG. 8(B), the vertical axis represents an average area CAA and the horizontal axis represents time. Also, in FIG. 8(B), a change over time in the average area CAA is indicated by a waveform WCAA. Also, in FIG. 8(B), change points of the average area CAA due to the time transition are referred to as time t21, time t22, and time t23, respectively. In this example, a case where the waveform WCAA indicating the average area CAA shows a constant value from time t0 to time t21, decreases from time t22 to time t23, and shows a constant value at time t23 will be described.

As shown in FIG. 8(B), the area determination unit 143 determines whether or not cells in the second differentiation-inducing process have differentiated from time t1. Also, as shown in FIG. 8(B), at time t22, the average area CAA calculated by the average area calculation unit 142 is less than the differentiation determination threshold value MTH2. That is, at time t22, it is shown that the cell cluster area CSS is smaller than that at the start of the culture process. That is, the area determination unit 143 determines that cells in the second differentiation-inducing process have differentiated at time t22.

Also, as shown in FIG. 8(B), at time t2, the waveform WCAA indicating the average area CAA calculated by the area determination unit 143 is less than the determination transition threshold value JTH2. That is, the area determination unit 143 determines whether or not cells have differentiated between time t1 and time t2.

Regarding Density-Specific Arithmetic Unit 150

Next, the density-specific arithmetic unit 150 will be described with reference to FIG. 4. The density-specific arithmetic unit 150 includes an area/perimeter calculation unit 151, a density calculation unit 152, and a density determination unit 153.

The area/perimeter calculation unit 151 acquires the third differentiation-inducing process image P3 from the acquisition unit 110. The area/perimeter calculation unit 151 extracts a portion of the cell image CP from the acquired third differentiation-inducing process image P3. In this example, the third differentiation-inducing process image P3 includes a plurality of imaged cells. The area/perimeter calculation unit 151 supplies a plurality of pieces of information indicating the extracted cell image CP to the density calculation unit 152.

The density calculation unit 152 acquires a plurality of cell images CP from the area/perimeter calculation unit 151. The density calculation unit 152 calculates a cell area CS on the basis of the plurality of cell images CP that have been acquired. Also, the density calculation unit 152 calculates perimeters of cells on the basis of the acquired plurality of cell images CP and calculates an average cell perimeter CL on the basis of the calculated perimeters of the cells. The density calculation unit 152 calculates a ratio of the average cell perimeter CL to the cell area CS for each acquired cell image CP. Also, the density calculation unit 152 calculates a density CPT, which is an average value of the ratio of the average cell perimeter CL to the cell area CS calculated for each cell image CP. The density calculation unit 152 supplies the calculated density CPT to the density determination unit 153.

The density determination unit 153 determines whether or not cells have differentiated in the third differentiation-inducing process. Specifically, the density determination unit 153 acquires the density CPT from the density calculation unit 152. The density determination unit 153 determines whether or not cells have differentiated in the third differentiation-inducing process on the basis of the acquired density CPT and the differentiation determination threshold value MTH3. In this example, the density determination unit 153 determines that cells have differentiated when the density CPT is less than the differentiation determination threshold value MTH3.

The density-specific arithmetic unit 150 acquires the average area CAA from the average area calculation unit 142. The density-specific arithmetic unit 150 starts the calculation when the average area CAA is less than the determination transition threshold value JTH2. The density determination unit 153 starts the determination after the transition from the second differentiation-inducing process to the third differentiation-inducing process. That is, the density determination unit 153 starts the determination from the time when the area determination unit 143 has ended the determination.

Hereinafter, the determination process of the density determination unit 153 will be described with reference to FIG. 8(C). In FIG. 8(C), a graph of a change over time in the density CPT is shown. In FIG. 8(C), the vertical axis represents a density CPT and the horizontal axis represents time. Also, in FIG. 8(C), a change over time in the density CPT is indicated by a waveform WCPT. Also, in FIG. 8(C), change points due to the time transition in the density CPT are referred to as time t31 and time 32, respectively. In this example, a case where the waveform WCPT indicating the density CPT gradually decreases from time t0 to time t32 and shows a constant value at time t32 will be described.

As shown in FIG. 8(C), the density determination unit 153 determines whether or not cells in the third differentiation-inducing process have differentiated from time t1. Also, as shown in FIG. 8(C), at time 31, the waveform WCPT indicating the density CPT calculated by the density calculation unit 152 is less than the differentiation determination threshold value MTH3. Here, when cells have various shapes, gaps may occur between the cells. On the other hand, when the shape of the cells becomes uniform (for example, circular), gaps between the cells are unlikely to occur (i.e., the density CPT becomes high). In other words, when the density CPT becomes high, the cell shape may be close to a circle. That is, it is shown that the shape of the cells is closer to a circle at time t31 than at the start of the culture process. That is, the density determination unit 153 determines that cells in the third differentiation-inducing process have differentiated at time 31.

Figure 9:
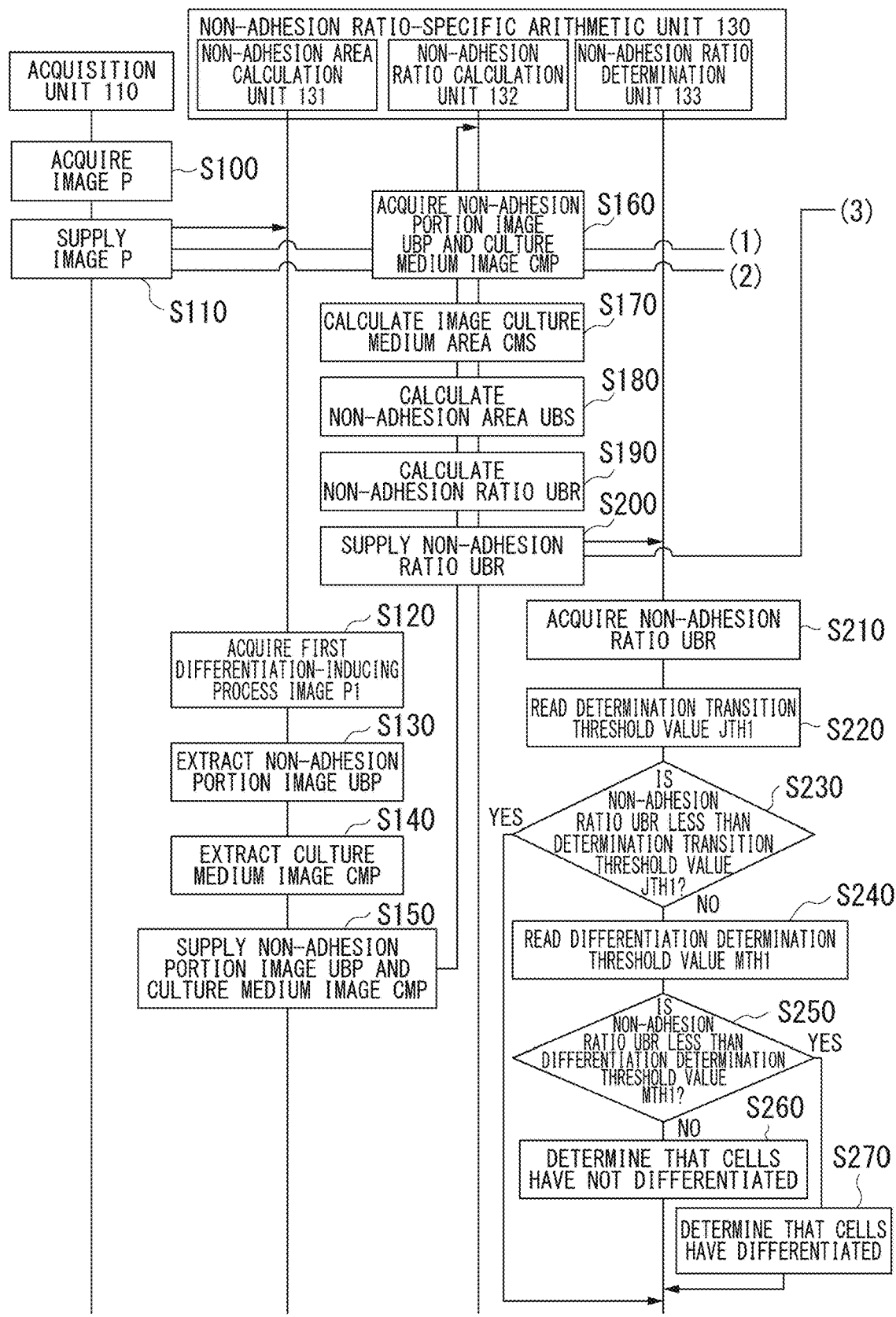
FIG. 9 is a flowchart (Part 1) showing an example of an operation of the image determination device according to the first embodiment.
Figure 10:
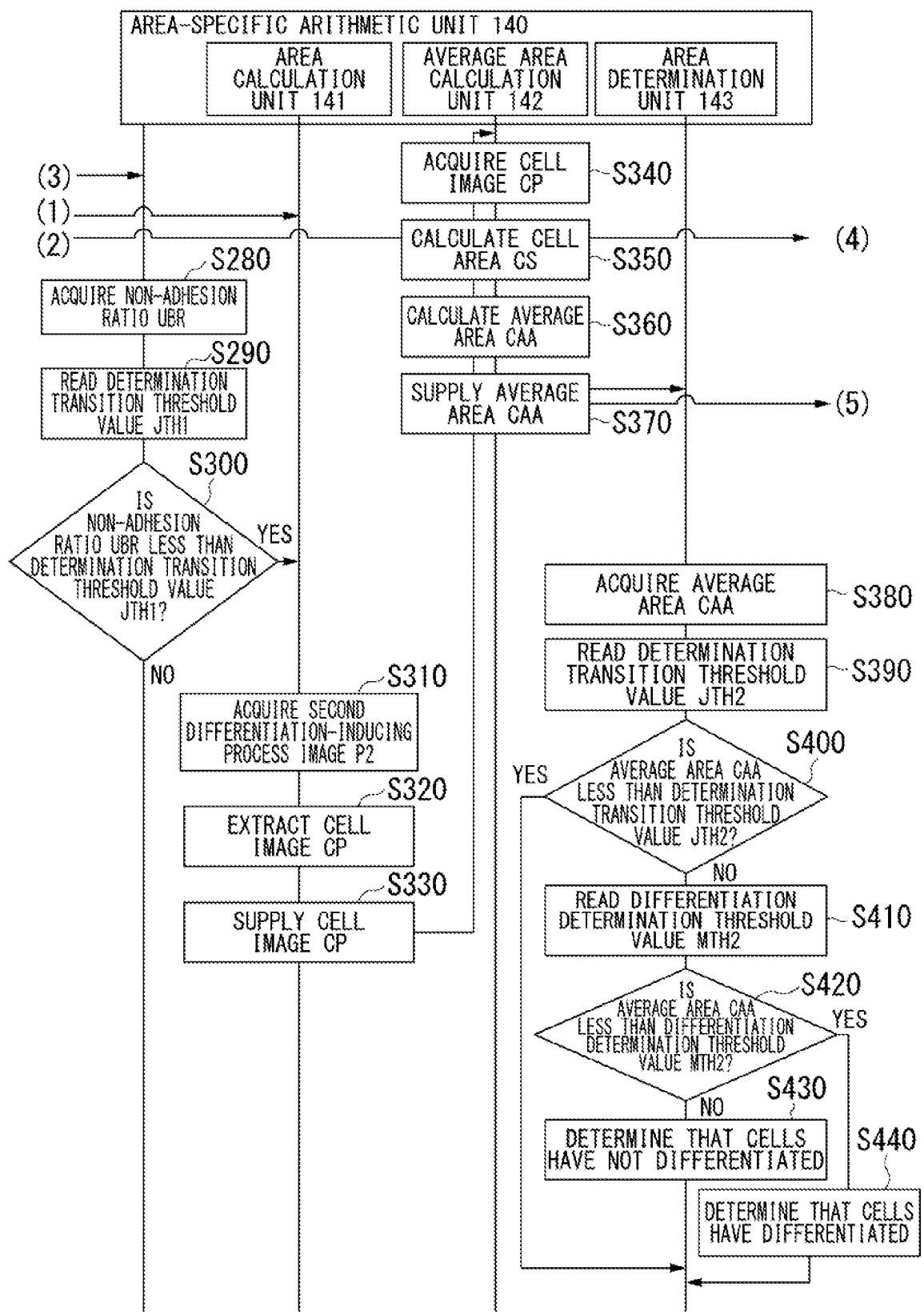
FIG. 10 is a flowchart (Part 2) showing an example of the operation of the image determination device according to the first embodiment.
Figure 11:
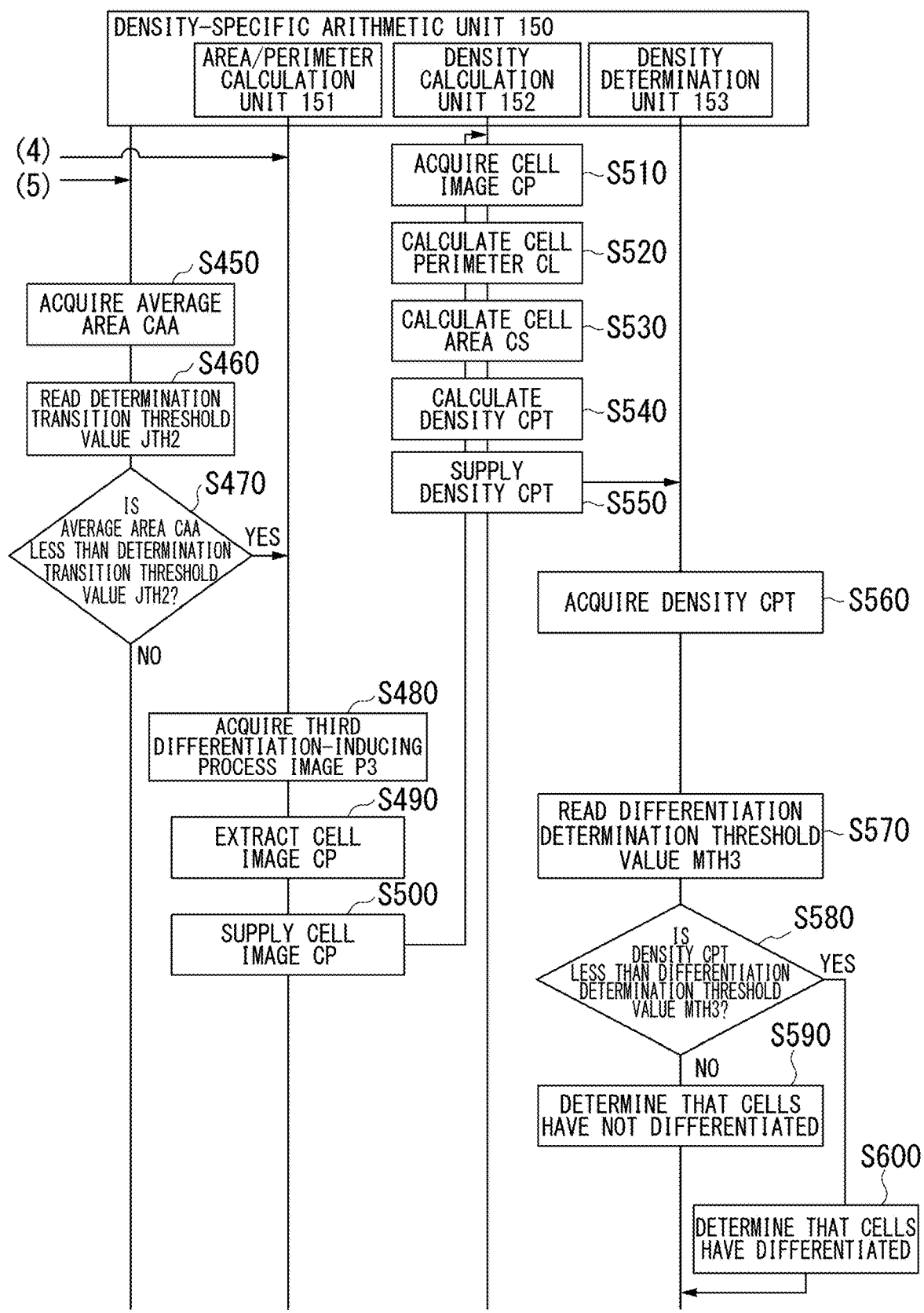
FIG. 11 is a flowchart (Part 3) showing an example of the operation of the image determination device according to the first embodiment.

Hereinafter, an operation of the image determination device 10 will be described with reference to FIG. 9. FIG. 9 is a flowchart (Part 1) showing an example of the operation of the image determination device 10 according to the first embodiment FIG. 10 is a flowchart (Part 2) showing an example of the operation of the image determination device 10 according to the first embodiment. FIG. 11 is a flowchart (Part 3) showing an example of the operation of the image determination device 10 according to the first embodiment. The acquisition unit 110 acquires an image P from the imaging device 34 (step S100). The acquisition unit 110 supplies the image P to each part provided in the control unit 100 (step S110).

The non-adhesion area calculation unit 131 provided in the non-adhesion ratio-specific arithmetic unit 130 acquires a first differentiation-inducing process image P1 from among a plurality of images P (the first differentiation-inducing process image P1, the second differentiation-inducing process image P2, and the third differentiation-inducing process image P3) in each differentiation step acquired by the acquisition unit 110 from the imaging device 34 (step S120). The non-adhesion area calculation unit 131 extracts a non-adhesion portion image UBP from the first differentiation-inducing process image P1 (step S130). The non-adhesion area calculation unit 131 extracts a culture medium image CMP from the first differentiation-inducing process image P1 (step S140). The non-adhesion area calculation unit 131 supplies the non-adhesion portion image UBP and the culture medium image CMP to the non-adhesion ratio calculation unit 132 (step S150). The non-adhesion ratio calculation unit 132 provided in the non-adhesion ratio-specific arithmetic unit 130 acquires the non-adhesion portion image UBP and the culture medium image CMP from the non-adhesion area calculation unit 131 (step S160). The non-adhesion ratio calculation unit 132 calculates an image-specific culture medium area CMS on the basis of the acquired culture medium image CMP (step S170). The non-adhesion ratio calculation unit 132 calculates the non-adhesion area UBS on the basis of the acquired non-adhesion portion image UBP (step S180). The non-adhesion ratio calculation unit 132 calculates anon-adhesion ratio UBR on the basis of the calculated image-specific culture medium area CMS and the non-adhesion area UBS (step S190). The non-adhesion ratio calculation unit 132 supplies the calculated non-adhesion ratio UBR to the non-adhesion ratio determination unit 133 and the area-specific arithmetic unit 140 (step S200).

The non-adhesion ratio determination unit 133 provided in the non-adhesion ratio-specific arithmetic unit 130 acquires the non-adhesion ratio UBR from the non-adhesion ratio calculation unit 132 (step S210). The non-adhesion ratio determination unit 133 reads the determination transition threshold value JTH1 from the storage unit 300 (step S220).

The non-adhesion ratio determination unit 133 determines whether or not the non-adhesion ratio UBR is less than the determination transition threshold value JTH1 (step S230). When it is determined that the non-adhesion ratio UBR is less than the determination transition threshold value JTH1 (step S230; YES), the non-adhesion ratio determination unit 133 ends the process without making the determination. Also, when it is determined that the non-adhesion ratio UBR exceeds the determination transition threshold value JTH1 (step S230; NO), the non-adhesion ratio determination unit 133 reads the differentiation determination threshold value MTH1 from the storage unit 300 (step S240). The non-adhesion ratio determination unit 133 determines whether or not the non-adhesion ratio UBR is less than the differentiation determination threshold value MTH1 (step S250). When it is determined that the non-adhesion ratio UBR is less than the differentiation determination threshold value MTH1 (step S250; YES), the non-adhesion ratio determination unit 133 determines that cells have differentiated in the first differentiation-inducing process (step S260). Also, when it is determined that the non-adhesion ratio UBR exceeds the differentiation determination threshold value MTH1 (step S250; NO), the non-adhesion ratio determination unit 133 determines that cells have not differentiated in the first differentiation-inducing process (step S270).

The area-specific arithmetic unit 140 acquires the non-adhesion ratio UBR from the non-adhesion ratio calculation unit 132 (step S280). The area-specific arithmetic unit 140 reads the determination transition threshold value JTH1 from the storage unit 300 (step S290). The area-specific arithmetic unit 140 determines whether or not the non-adhesion ratio UBR is less than the determination transition threshold value JTH1 (step S300). When it is determined that the non-adhesion ratio UBR is less than the determination transition threshold value JTH1 (step S300; YES), the area-specific arithmetic unit 140 moves the process to step S310. The area calculation unit 141 does not start the process while it is determined that the non-adhesion ratio UBR exceeds the determination transition threshold value JTH1 (step S300; NO). The area calculation unit 141 provided in the area-specific arithmetic unit 140 acquires an image P acquired (captured) at a timing after an image P in which it is determined that the non-adhesion ratio UBR is less than the determination transition threshold value JTH1 among the plurality of images P acquired by the acquisition unit 110 as the second differentiation-inducing process image P2 (step S310). The area calculation unit 141 extracts a plurality of cell cluster images CCP from the acquired second differentiation-inducing process image P2 (step S320). The area calculation unit 141 supplies information indicated by the plurality of cell cluster images CCP that have been extracted to the average area calculation unit 142 (step S330).

The average area calculation unit 142 provided in the area-specific arithmetic unit 140 acquires a plurality of cell cluster images CCP from the area calculation unit 141 (step S340). The average area calculation unit 142 calculates a cell cluster area CSS on the basis of the plurality of cell cluster images CCP that have been acquired (step S350). The average area calculation unit 142 calculates an average area CAA on the basis of the calculated cell cluster area CSS (step S360). The average area calculation unit 142 supplies the calculated average area CAA to the area determination unit 143 and the density-specific arithmetic unit 150 (step S370).

The area determination unit 143 provided in the area-specific arithmetic unit 140 acquires the average area CAA from the average area calculation unit 142 (step S380). The area determination unit 143 reads the determination transition threshold value JTH2 from the storage unit 300 (step S390). The area determination unit 143 determines whether or not the average area CAA is less than the determination transition threshold value JTH2 (step S400). When the area determination unit 143 determines that the average area CAA is not less than the determination transition threshold value JTH2 (step S400; NO), the area determination unit 143 reads the differentiation determination threshold value MTH2 from the storage unit 300 (step S410). Also, when it is determined that the average area CAA is less than the determination transition threshold value JTH2 (step S400; YES), the area determination unit 143 ends the process without making the determination. The area determination unit 143 reads the differentiation determination threshold value MTH2 from the storage unit 300 (step S410). The area determination unit 143 determines whether or not the average area CAA is less than the differentiation determination threshold value MTH2 (step S420). When it is determined that the average area CAA is less than the differentiation determination threshold value MTH2 (step S420; YES), the area determination unit 143 determines that cells have differentiated in the second differentiation-inducing process (step S440). Also, when it is determined that the average area CAA exceeds the differentiation determination threshold value MTH2 (step S420; NO), the area determination unit 143 determines that cells have not differentiated in the second differentiation-inducing process (step S430).

The density-specific arithmetic unit 150 acquires the average area CAA from the average area calculation unit 142 (step S450). The density-specific arithmetic unit 150 reads the determination transition threshold value JTH2 from the storage unit 300 (step S460). The density-specific arithmetic unit 150 determines whether or not the average area CAA is less than the determination transition threshold value JTH2 (step S470). When it is determined that the average area CAA is less than the determination transition threshold value JTH2 (step S470; YES), the density-specific arithmetic unit 150 moves the process to step S480. The density-specific arithmetic unit 150 does not start the process while it is determined that the average area CAA exceeds the determination transition threshold value JTH2 (step S470; NO). The area/perimeter calculation unit 151 provided in the density-specific arithmetic unit 150 acquires an image P acquired (captured) at a timing after an image P in which it is determined that the average area CAA is less than the determination transition threshold value JTH2 among the plurality of images P acquired by the acquisition unit 110 as the third differentiation-inducing process image P3 (step S480). The area/perimeter calculation unit 151 extracts a plurality of cell images CP from the acquired third differentiation-inducing process image P3 (step S490). The area/perimeter calculation unit 151 supplies a plurality of cell images CP that have been extracted to the density calculation unit 152 (step S500).

The density calculation unit 152 provided in the density-specific arithmetic unit 150 acquires the plurality of cell images CP from the area/perimeter calculation unit 151 (step S510). The density calculation unit 152 calculates an average cell perimeter CL on the basis of the plurality of cell images CP that have been acquired (step S520). The density calculation unit 152 calculates a cell area CS on the basis of the plurality of cell images CP that have been acquired (step S530). Also, the density calculation unit 152 calculates the average cell perimeter CL on the basis of the plurality of cell images CP that have been acquired (step S540). The density calculation unit 152 calculates a density CPT on the basis of the calculated cell area CS and the average cell perimeter CL (step S540). The density calculation unit 152 supplies the calculated density CPT to the density determination unit 153 (step S550).

The density calculation unit 152 provided in the density-specific arithmetic unit 150 acquires the density CPT from the density calculation unit 152 (step S560). The density determination unit 153 reads the differentiation determination threshold value MTH3 from the storage unit 300 (step S570). The density determination unit 153 determines whether or not the density CPT is less than the differentiation determination threshold value MTH3 (step S580). When it is determined that the density CPT is less than the differentiation determination threshold value MTH3 (step S580; YES), the density determination unit 153 determines that cells have differentiated in the third differentiation-inducing process (step S600). Also, when it is determined that the density CPT exceeds the differentiation determination threshold value MTH3 (step S580; NO), the density determination unit 153 determines that cells have not differentiated in the third differentiation-inducing process (step S590). Subsequently, the image determination device 10 iterates the processing of steps S100 to S600 at a user's input or at a prescribed timing.

As described above, the image determination device 10 includes an acquisition unit 110, a non-adhesion ratio-specific arithmetic unit 130, an area-specific arithmetic unit 140, and a density-specific arithmetic unit 150. The non-adhesion ratio-specific arithmetic unit 130 includes a non-adhesion ratio calculation unit 132 and a non-adhesion ratio determination unit 133. The area-specific arithmetic unit 140 includes an average area calculation unit 142 and an area determination unit 143. The density-specific arithmetic unit 150 includes the density calculation unit 152 and the density determination unit 153. The acquisition unit 110 acquires a plurality of images P obtained by the imaging device 34 imaging cells being cultured in the culture medium according to the elapse of time. The non-adhesion ratio-specific arithmetic unit 130, the area-specific arithmetic unit 140, and the density-specific arithmetic unit 150 determine whether or not cells have differentiated in each differentiation-inducing process on the basis of various types of information.

Thereby, the image determination device 10 can determine whether or not cells have differentiated on the basis of an image P obtained by imaging the cells being culture, a plurality of calculation units, and a plurality of determination units. That is, the image determination device 10 can determine whether or not cells have differentiated on the basis of an index according to each differentiation-inducing process of the first differentiation-inducing process, the second differentiation-inducing process, and the third differentiation-inducing process. Thereby, the image determination device 10 can reduce the time and effort for determining a cell culture state on the basis of information according to the cell differentiation-inducing process.

Also, the non-adhesion ratio calculation unit 132 calculates a non-adhesion ratio UBR on the basis of the image-specific culture medium area CMS and the non-adhesion area UBS. The average area calculation unit 142 calculates an average area CAA on the basis of the cell cluster area CSS. The density calculation unit 152 calculates a density CPT on the basis of the cell area CS and the average cell perimeter CL. Thereby, the image determination device 10 can determine whether or not cells have differentiated on the basis of indices according to the differentiation-inducing processes calculated by the plurality of calculation units. That is, the image determination device 10 can determine whether or not cells have differentiated on the basis of an index according to each differentiation-inducing process of the first differentiation-inducing process, the second differentiation-inducing process, and the third differentiation-inducing process.

Also, the area determination unit 143 provided in the area-specific arithmetic unit 140 starts the determination on the basis of the fact that the non-adhesion ratio UBR calculated by the non-adhesion ratio calculation unit 132 is less than the determination transition threshold value JTH1. Thereby, the image determination device 10 can determine whether or not cells have differentiated on the basis of an index according to the transition from the first differentiation-inducing process to the second differentiation-inducing process. That is, the image determination device 10 can determine whether or not cells have differentiated on the basis of indices according to the first differentiation-inducing process and the second differentiation-inducing process.

Also, the density-specific arithmetic unit 150 starts the determination on the basis of the fact that the average area CAA calculated by the average area calculation unit 142 is less than the determination transition threshold value JTH2. Thereby, the image determination device 10 can determine whether or not cells have differentiated on the basis of an index according to the transition from the second differentiation-inducing process to the third differentiation-inducing process. That is, the image determination device 10 can determine whether or not cells have differentiated on the basis of indices according to the second differentiation-inducing process and the third differentiation-inducing process.

Second Embodiment

Figure 12:
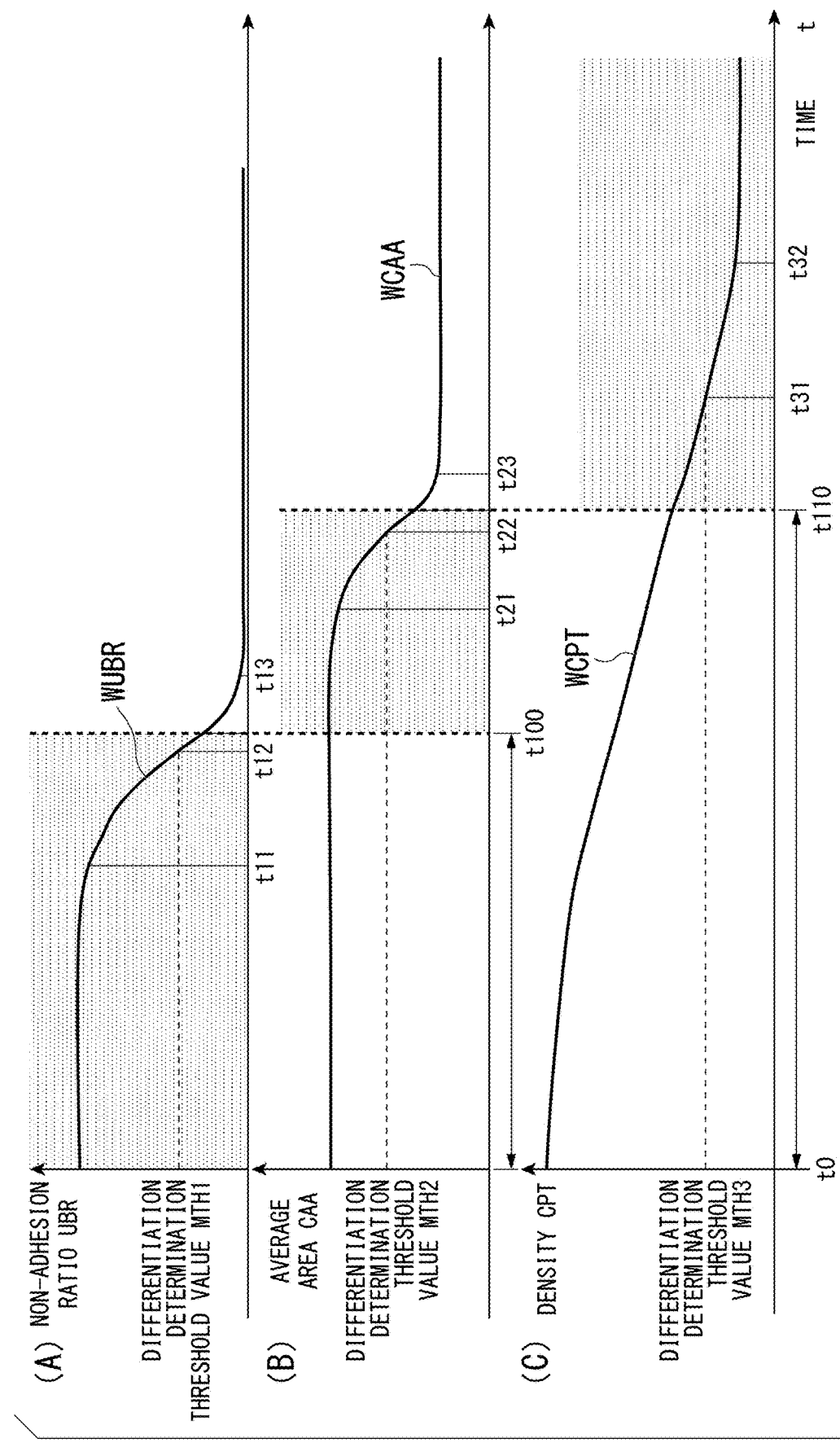
FIG. 12 is a graph showing an example of a determination process of a determination unit according to a second embodiment.

Hereinafter, a second embodiment of the present invention will be described with reference to FIG. 12. FIG. 12 is a graph showing an example of a determination process of a determination unit according to the second embodiment. Components and operations that are similar to those of the first embodiment described above are denoted by the same reference signs and description thereof will be omitted. In the present embodiment, a case where determination processes of the non-adhesion ratio determination unit 133, the area determination unit 143, and the density determination unit 153 are started on the basis of the elapsed time of culturing of cells will be described. Specifically, during a period from time t0 to time t100, which is a prescribed time, the non-adhesion ratio determination unit 133 determines whether or not cells in a first differentiation-inducing process have differentiated on the basis of a non-adhesion ratio UBR calculated by the non-adhesion ratio calculation unit 132 and a differentiation determination threshold value MTH1. Also, the non-adhesion ratio determination unit 133 ends the determination at time t100. Also, during a period from time t100 to time t110, which is a prescribed time, the area determination unit 143 determines whether or not cells in a second differentiation-inducing process have differentiated on the basis of an average area CAA calculated by the average area calculation unit 142 and a differentiation determination threshold value MTH2. Also, the area determination unit 143 ends the determination at time t110. Also, after time t110, the density determination unit 153 determines whether or not cells in a third differentiation-inducing process have differentiated on the basis of a density CPT calculated by the density calculation unit 152 and a differentiation determination threshold value MTH3.

As described above, the non-adhesion ratio determination unit 133, the area determination unit 143, and the density determination unit 153 provided in the non-adhesion ratio-specific arithmetic unit 130, the area-specific arithmetic unit 140, and the density-specific arithmetic unit 150 start the determination processes on the basis of the elapsed time of culturing of cells. Thereby, the image determination device 10 can determine whether or not cells have differentiated on the basis of an index according to the transition to each differentiation-inducing process at the time of culturing of cells for which a period of each differentiation-inducing process is already clear. That is, the image determination device 10 can determine whether or not cells have differentiated on the basis of the index according to each differentiation-inducing process.

In a cell evaluation method using the image determination device 10 according to the present embodiment, a first evaluation index based on the elapsed time from the start of the culture process is acquired.

Modified Example 1

Figure 13:
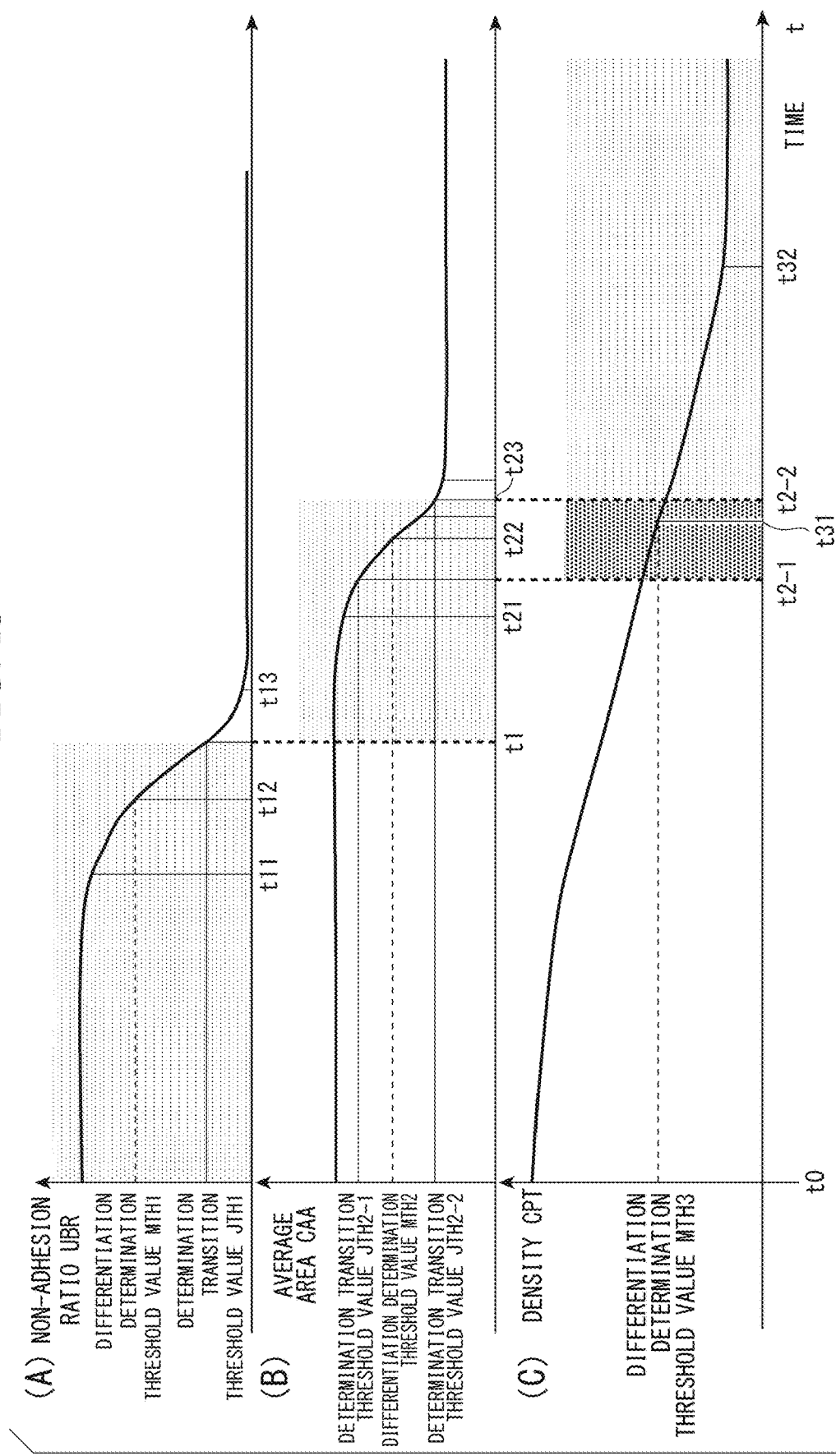
FIG. 13 is a graph showing an example of a determination process of a determination unit according to Modified Example 1.

Hereinafter, Modified Example 1 of the first embodiment described above will be described with reference to FIG. 13. FIG. 13 is a graph showing an example of a determination process of the determination unit in Modified Example 1. Components and operations that are similar to those of the first embodiment described above are denoted by the same reference signs and description thereof will be omitted.

In Modified Example 1, a case where the determination times of the non-adhesion ratio determination unit 133, the area determination unit 143, and the density determination unit 153 overlap will be described.

In this example, a case where two threshold values of a determination transition threshold value JTH2-1 and a determination transition threshold value JTH2-2 for a determination transition threshold value JTH indicating the end of the determination process of the area determination unit 143 and the start of the determination process of the density determination unit 153 are set will be described. In this case, as shown in FIG. 13, time t2-1 is a time when the area determination unit 143 determines that the average area CAA is less than the determination transition threshold value JTH2-1. Time t2-2 is a time when it is determined that the average area CAA is less than the determination transition threshold value JTH2-2. In the image determination device 10, during a period from time t2-1 to time t2-2, the area determination unit 143 may determine whether or not cells have differentiated and the density determination unit 153 may determine whether or not cells have differentiated.

In the above-described first embodiment, after a result of determining the average area CAA in the area-specific arithmetic unit 140 indicates that cells have differentiated, a process of determining the density CPT in the density-specific arithmetic unit 150 is started. Thus, when the result of determining the average area CAA in the area-specific arithmetic unit 140 indicates that cells have not differentiated, a process of determining the density CPT in the density-specific arithmetic unit 150 may not be started. Therefore, in the above-described first embodiment, the result of determining the density CPT in the density-specific arithmetic unit 150 may not be obtained according to a state of the cell cluster image CCP.

On the other hand, in Modified Example 1, the process of determining the density CPT in the density-specific arithmetic unit 150 is started regardless of the result of determining the average area CAA in the area-specific arithmetic unit 140. Therefore, in Modified Example 1, a result of determining the density CPT in the density-specific arithmetic unit 150 can be obtained regardless of the state of the cell cluster image CCP. That is, according to Modified Example 1, it is possible to reduce a frequency with which the result of determining the density CPT in the density-specific arithmetic unit 150 cannot be obtained.

Although the case where the determination times set by the determination transition threshold value JTH overlap has been described in this example, the present invention is not limited thereto. In the determination processes of the non-adhesion ratio determination unit 133, the area determination unit 143, and the density determination unit 153, determination periods may overlap according to the elapsed time of culturing of cells. Specifically, time t2-2 at which the determination process of the area determination unit 143 ends and time t2-1 at which the determination process of the density determination unit 153 starts may be set on the basis of the elapsed time of culturing of cells.

Modified Example 2

Figure 14:
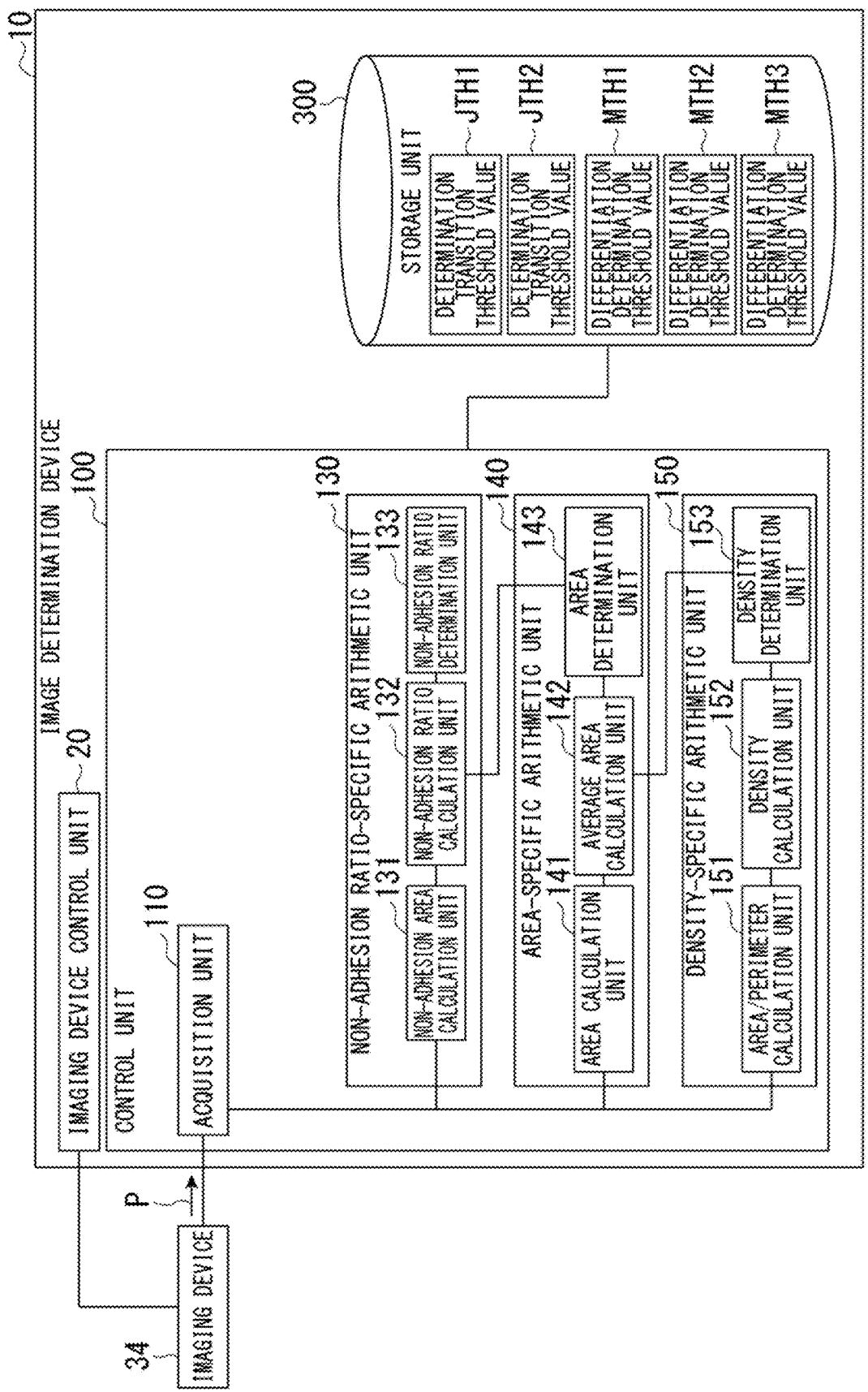
FIG. 14 is a schematic diagram showing an example of a configuration of an image determination device according to Modified Example 2.

Hereinafter, Modified Example 2 of each of the above-described embodiments will be described with reference to FIG. 14. FIG. 14 is a schematic diagram showing an example of a configuration of the image determination device in Modified Example 2. Components and operations that are similar to those of each embodiment described above are denoted by the same reference signs and description thereof will be omitted. In Modified Example 2, an image P acquired by the image determination device 10 from the imaging device 34 may be an image P obtained by imaging cells in any differentiation-inducing process. In this example, the non-adhesion ratio-specific arithmetic unit 130, the area-specific arithmetic unit 140, and the density-specific arithmetic unit 150 calculate indices in parallel on the basis of the image P supplied by the acquisition unit 110. Specifically, the non-adhesion area calculation unit 131 and the non-adhesion ratio calculation unit 132 calculate a non-adhesion ratio UBR on the basis of the image P supplied by the acquisition unit 110. Also, the area calculation unit 141 and the average area calculation unit 142 calculate an average area CAA on the basis of the image P supplied by the acquisition unit 110. Also, the area/perimeter calculation unit 151 and the density calculation unit 152 calculate a density CPT on the basis of the image P supplied by the acquisition unit 110. The non-adhesion ratio determination unit 133, the area determination unit 143, and the density determination unit 153 perform the determination processes when conditions are satisfied. Specifically, when the non-adhesion ratio UBR exceeds the determination transition threshold value JTH1, the non-adhesion ratio determination unit 133 determines whether or not cells have differentiated on the basis of the non-adhesion ratio UBR. Also, the area determination unit 143 determines whether or not cells have differentiated on the basis of the average area CAA when the non-adhesion ratio UBR is less than the determination transition threshold value JTH1 and when the average area CAA exceeds the determination transition threshold value JTH2. Also, when the average area CAA is less than the determination transition threshold value JTH2, the density determination unit 153 determines whether or not cells have differentiated on the basis of the density CPT.

Thereby, even if the image P captured by the imaging device 34 is any one of the first differentiation-inducing process image P1, the second differentiation-inducing process image P2, and the third differentiation-inducing process image P3, it is possible to determine whether or not cells have differentiated.

Third Embodiment

Hereinafter, a third embodiment of the present invention will be described with reference to FIGS. 15 to 34. In the above-described embodiments and modified examples, a configuration in which it is determined whether or not cells have differentiated on the basis of each differentiation-inducing process-specific index according to each differentiation-inducing process has been described. In the third embodiment, a configuration in which the quality of cell differentiation is determined using at least one common index regardless of the differentiation-inducing process will be described. Also, determining the quality of cell differentiation can be rephrased as evaluating cell differentiation and can be rephrased as determining the quality of cell maturation or evaluating cell maturation because differentiation is also a cell maturation process. Components and operations that are similar to those of the above-described embodiments and modified examples are denoted by the same reference signs and description thereof will be omitted. In the third embodiment, an undifferentiated state maintaining culture process in which cells are maintained and cultured in an undifferentiated state and a culture process of differentiating cells into mature hepatocytes among culture processes of differentiating iPS cell-derived endoderm cells into mature cells will be described as an example.

Even in the third embodiment, the mature cells are not limited to mature hepatocytes. The mature cells in the third embodiment are cells in which a paving stone region (to be described below) appears in a process of normal differentiation. Examples of such cells include adhesive epithelial cells derived from liver, ovary, skin, cornea, various types of digestive organs, tracheas, and various other types of mucous membranes.

Figure 15:
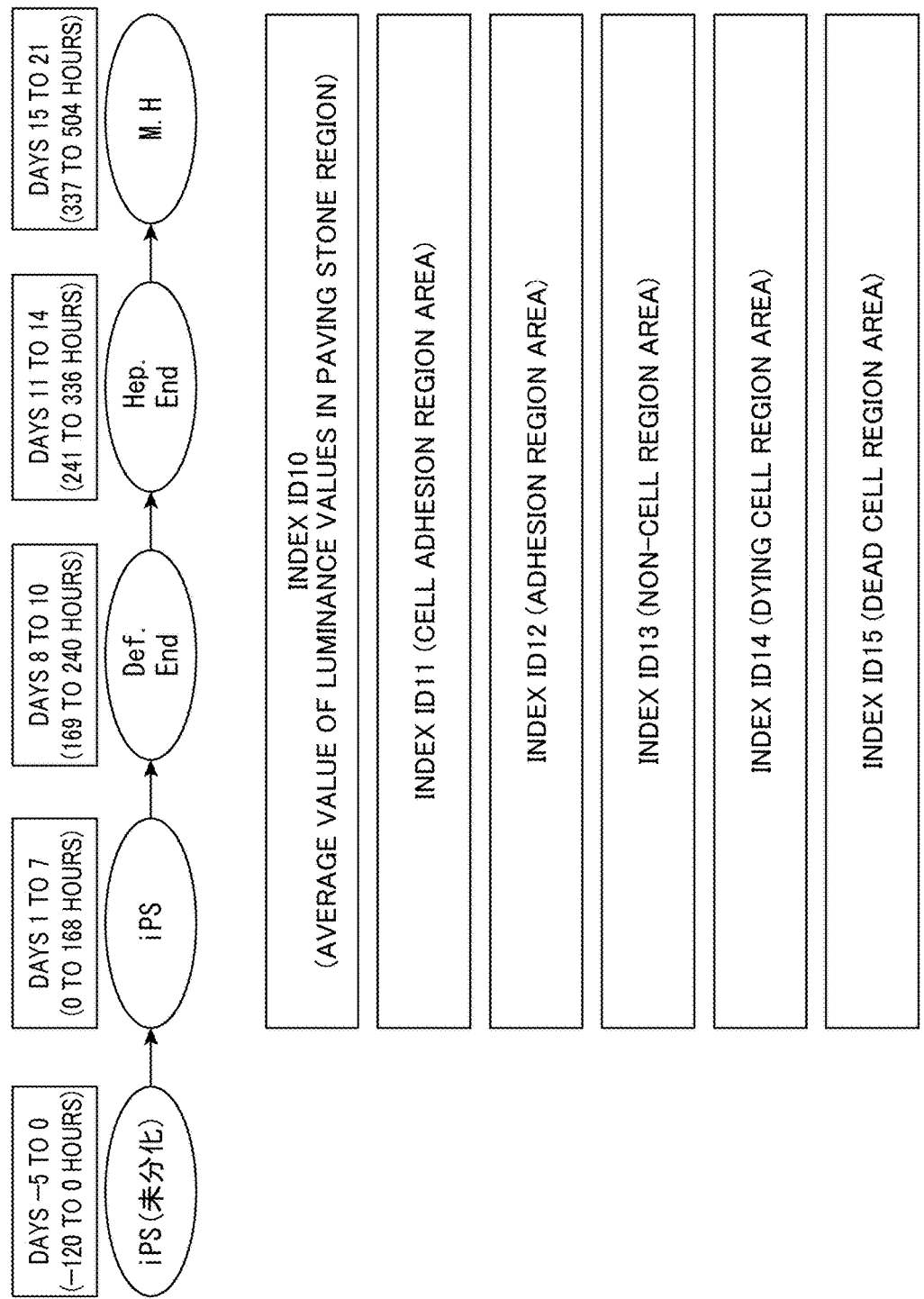
FIG. 15 is a schematic diagram showing an example of a culture process until differentiation of iPS cells into mature hepatocytes is performed according to a third embodiment.

FIG. 15 is a schematic diagram showing an example of a culture process until differentiation of iPS cells into mature hepatocytes is performed according to the third embodiment. The undifferentiated state maintaining culture process for iPS cells is a culture process (for example, 5 days) for increasing the number of iPS cells while maintaining the iPS cells in an undifferentiated state. The undifferentiated state maintaining culture process is performed during a period before the culture process for differentiation into mature hepatocytes. In the present embodiment, the undifferentiated state maintaining culture process is performed for days −5 to 0 (i.e., −120 to 0 hours) after the iPS cells are cultured in the culture medium. A first differentiation-inducing process in which iPS cells are induced to differentiate into endoderm cells is performed for days 1 to 7 (i.e., 0 to 168 hours) after the iPS cells are cultured in the culture medium. Also, a second differentiation-inducing process in which endoderm cells are induced to differentiate into hepatic endoderm cells is performed for days 8 to 10 (i.e., 169 to 240 hours) after the cell culture process is started. Also, a third differentiation-inducing process in which endoderm cells are induced to differentiate into hepatic endoderm cells is performed for days 11 to 14 (i.e., 241 to 336 hours) after the cell culture process is started. Also, a fourth differentiation-inducing process in which hepatic endoderm cells are induced to differentiate into mature hepatocytes is performed for days 15 to 21 (i.e., 337 to 504 hours) after the cell culture process is started.

The image determination device 10 determines the quality of cell differentiation on the basis of six evaluation indices obtained from images (i.e., time-lapse images of cells) acquired during the first to fourth differentiation-inducing processes (i.e., days 1 to 21). As shown in FIG. 15, the six evaluation indices are an average value of luminance values in the paving stone region (an index ID10), an area of the cell adhesion region (an index ID11), an area of the adhesion region (an index ID12), an area of the non-cell region (an index ID13), an area of the dying and dead cell region (an index ID14), an area of the dead cell region (an index ID15).

Also, the time-lapse images of the cells are images of cells captured in time series. The time-lapse images include at least two or more images captured at different times. Hereinafter, the configuration of the image determination device 10 will be described.

Figure 16:
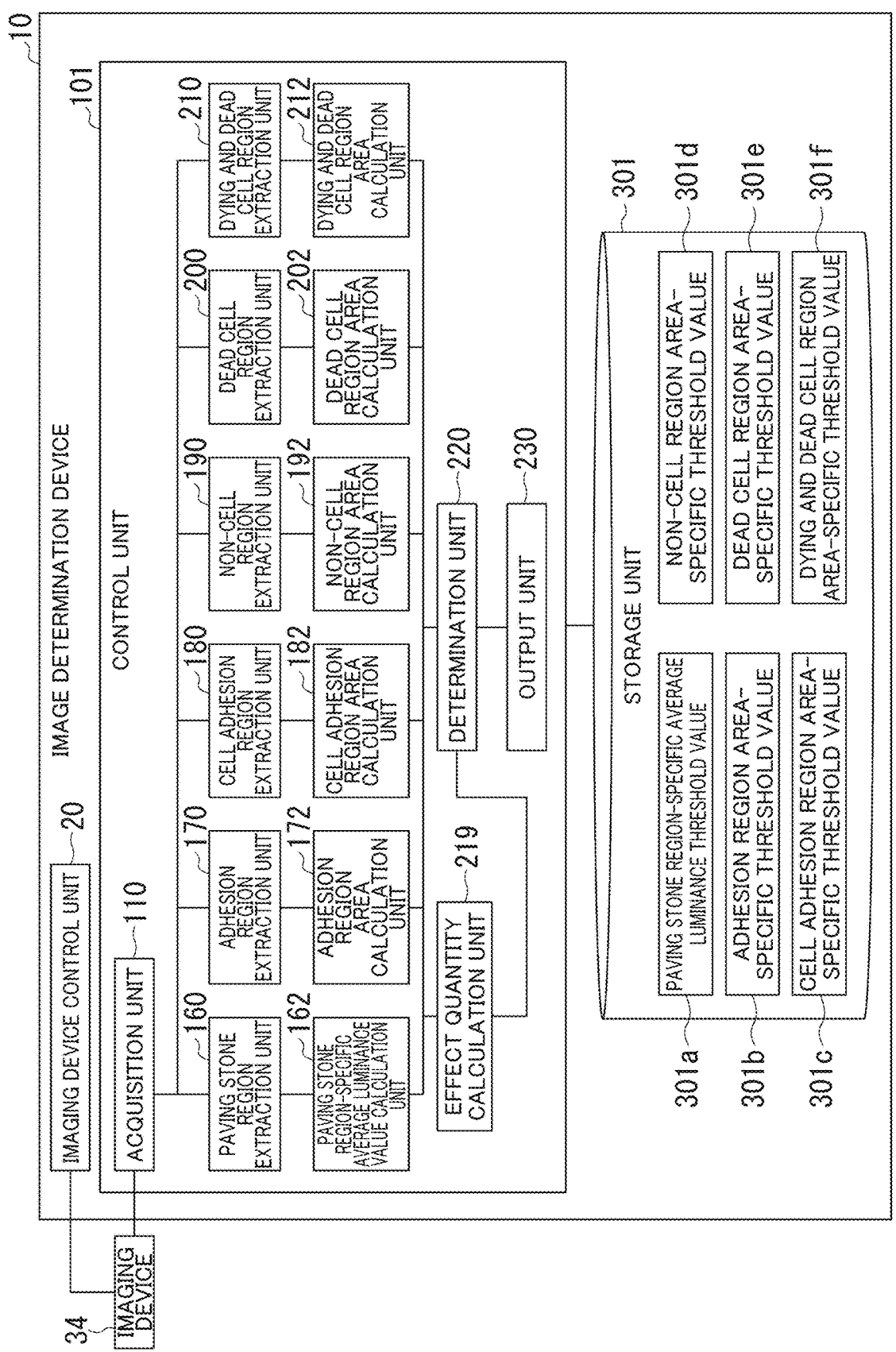
FIG. 16 is a diagram showing an example of a configuration of the image determination device of the third embodiment.

FIG. 16 is a diagram showing an example of a configuration of the image determination device 10 of the third embodiment. As shown in FIG. 16, the imaging device 34 and the image determination device 10 are connected so that they can transmit and receive information. The imaging device 34 images the cells being cultured in the culture medium according to the elapse of time. Specifically, the imaging device 34 captures an image P, which is an image of cells containing the culture medium, according to the elapse of time. The imaging device 34 captures an image of the cells and supplies the image P that has been generated to the image determination device 10.

As shown in FIG. 16, the image determination device 10 of the third embodiment includes a control unit 101 and a storage unit 301. The control unit 101 implements an acquisition unit 110, a paving stone region extraction unit 160, a paving stone region-specific average luminance value calculation unit 162, an adhesion region extraction unit 170, an adhesion region area calculation unit 172, an cell adhesion region extraction unit 180, a cell adhesion region area calculation unit 182, a non-cell region extraction unit 190, a non-cell region area calculation unit 192, a dead cell region extraction unit 200, a dead cell region area calculation unit 202, a dying and dead cell region extraction unit 210, a dying and dead cell region area calculation unit 212, an effect quantity calculation unit 219, a determination unit 220, and an output unit 230 as functional units when a hardware processor such as a CPU executes a program (software) stored in the storage unit 301. Some or all of these components may be implemented by hardware such as an LSI circuit, an ASIC, an FPGA, or a GPU or may be implemented by software and hardware in cooperation. The storage unit 301 is implemented by, for example, a ROM, a flash memory, an SD card, a RAM, a register, or the like. The storage unit 301 stores various types of values such as a paving stone region-specific average luminance threshold value 301a, an adhesion region area-specific threshold value 301b, a cell adhesion region area-specific threshold value 301c, a non-cell region area-specific threshold value 301d, a dead cell region area-specific threshold value 301e, and a dying and dead cell region area-specific threshold value 301f in advance.

These threshold values are values predetermined by comparing indices (for example, a paving stone region luminance value, an adhesion region area, a cell adhesion region area, a non-cell region area, a photoreceptor cell region area, a dying and dead cell region area, and the like) based on an image P for which the observer observes cells and determines that the observed cells have become normal mature hepatocytes with indices (for example, a paving stone region luminance value, an adhesion region area, a cell adhesion region area, a non-cell region area, a photoreceptor cell region area, a dying and dead cell region area, and the like) based on an image P for which the observer observes cells and determines that the observed cells have not become normal mature hepatocytes (for example, that the observed cells have not become mature hepatocytes, that the observed cells have become abnormal mature hepatocytes, or the like). Details of information will be described below.

Also, the observer may not determine whether or not cells have become mature hepatocytes by observing the cells. The observer may make the determination, for example, using existing biochemical indices. In this case, for example, it may be determined whether or not the hepatocytes have become mature hepatocytes in an enzyme-linked immunosorbent assay (ELISA) method.

The acquisition unit 110 of the present embodiment supplies the image P acquired from the imaging device 34 to the paving stone region extraction unit 160, the adhesion region extraction unit 170, the cell adhesion region extraction unit 180, the non-cell region extraction unit 190, the dead cell region extraction unit 200, and the dying and dead cell region extraction unit 210.

<Regarding Paving Stone Region>

Figure 17:
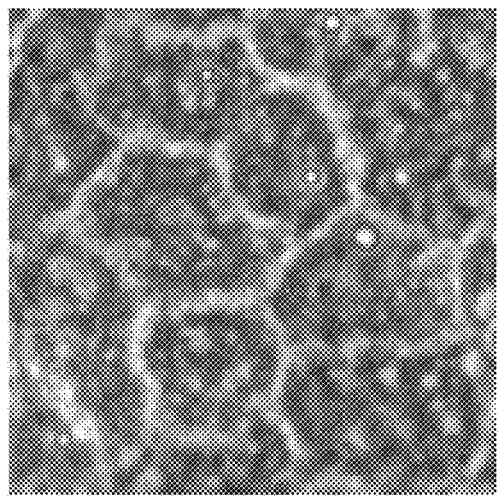
FIG. 17 is a diagram showing an example of cells having a paving stone-shaped form.

The paving stone region extraction unit 160 extracts a paving stone-shaped region from the image P. FIG. 17 is a diagram showing an example of cells having a paving stone-shaped form. As shown in FIG. 17, the contrast between the cell membrane of the cell and the inside of the cell membrane (i.e., cytoplasm, nucleus, or the like) increases as the differentiation of iPS cells into hepatic endoderm cells progresses. The cells (hepatic endoderm cells) are arranged while adhering to the culture vessel as if the cells are laid out with paving stones and spread in the culture medium. In the following description, a paving stone laying pattern in which the cells spread in the culture medium while adhering to the culture vessel is also referred to as a paving stone shape. The paving stone laying pattern is, for example, a pattern in which plane figures having irregular sizes and shapes are laid out in a plane with almost no gap between them. Also, cells that form the paving stone laying pattern are also referred to as "cells having a paving stone-shaped form." The paving stone laying pattern may be formed by one "cell having a paving stone-shaped form" or may be formed by a plurality of "cells having a paving stone-shaped form." Also, it can be said that the cells having a paving stone-shaped form are cells in which differentiation from iPS cells is normally progressing. The paving stone region extraction unit 160 extracts a region (in other words, a cell membrane of a cell having the paving stone-shaped form and a cytoplasmic region of the cell) of the image P surrounded by a contour of outer circumference of a cell having the paving stone-shaped form as a paving stone-shaped region (hereinafter referred to as a paving stone region). Also, the paving stone region extraction unit 160 may extract a region of the image P surrounded by a contour of outer circumference around which a plurality of cells having a paving stone-shaped form are gathered or may further extract a set of pixels of a plurality of paving stone regions within the image P as the paving stone region.

Also, the paving stone region extraction unit 160 determines whether or not cells have formed the paving stone region. Here, the paving stone region extraction unit 160 determines whether or not cells have formed a paving stone region on the basis of, for example, an average value obtained by averaging differences between luminance values in the cytoplasm of the cells imaged in the image P and luminance values of the cell membranes thereof with respect to all cells imaged in the image P. Also, it may be determined whether or not cells have formed the paving stone region on the basis of an average luminance value of pixels in a region where a cell form shows a prescribed feature among the plurality of cells imaged in the image P. The paving stone region extraction unit 160 is an example of a paving stone region determination unit.

The paving stone region-specific average luminance value calculation unit 162 calculates an average value of luminance values in pixels indicating a paving stone region extracted by the paving stone region extraction unit 160. The paving stone region-specific average luminance value calculation unit 162 may calculate a median value of the luminance values instead of (or in addition to) the configuration in which the average value of the luminance values is calculated, may calculate the most frequent value of the luminance values, may calculate variance of the luminance values, may calculate a coefficient of variation of the luminance value (a value by dividing standard deviation of the luminance value by the average value of the luminance values), may calculate an average value, a median value, variance, a coefficient of variation, and the like with respect to a luminance value of a paving stone region having an area greater than or equal to the threshold value, or may calculate an area of the paving stone region. In the following description, a case where the paving stone region-specific average luminance value calculation unit 162 calculates an average value of luminance values in pixels showing the paving stone region will be described as an example and the average value will also be referred to as an "average value of luminance values in the paving stone region."

<Regarding Adhesion Region>

The adhesion region extraction unit 170 extracts an adhesion region from the image P. As described above, iPS cells adhere to a culture vessel as the differentiation-inducing process for hepatic endoderm cells progresses. Here, cells having the above-described paving stone-shaped form, cells whose quality of differentiation is low, cells that are undergoing differentiation, or impurities in the cell culture process may adhere to the culture vessel. The impurities in the cell culture process include, for example, garbage generated when the culture medium is replaced, cell residue generated when cells are crushed, and the like. The adhesion region extraction unit 170 extracts a region of cells having a paving stone-shaped form (i.e., a paving stone region), a region of cells whose quality of differentiation is low, a region of cells that are undergoing differentiation (a cell adhesion region to be described below), and a region containing a region of impurities and the like in the cell culture process as an adhesion region. In other words, the adhesion region is a region containing cells in culture adhering to the culture vessel 19 or the substrate of the culture vessel 19 and impurities in the cell culture process. Also, the adhesion region area calculation unit 172 calculates an area of the adhesion region extracted by the adhesion region extraction unit 170.

<Regarding Cell Adhesion Region>

The cell adhesion region extraction unit 180 extracts a cell adhesion region from the image P. As described above, in addition to the cells having the paving stone-shaped form described above, cells whose quality of differentiation is low or cells that are undergoing differentiation may adhere to the culture vessel. Cells whose quality of differentiation is low or cells that are undergoing differentiation do not form a paving stone-shaped form and are, for example, densely packed. The cell adhesion region extraction unit 180 extracts a region within the image P or a region of cells whose quality of differentiation is low or a region of cells that are undergoing differentiation among cell regions shown in the image P as a cell adhesion region. Here, the cell adhesion region is a region of cells adhering to the culture vessel other than the paving stone-shaped region (a region of cells having a paving stone-shaped form). Although the case where a factor that causes the cell adhesion region is that cells whose quality of differentiation is low or cells that are undergoing differentiation are densely packed without forming a paving stone-shaped form has been described above as an example, the factor that causes the cell adhesion region is not limited thereto. The cell adhesion region area calculation unit 182 calculates an area of the cell adhesion region extracted by the cell adhesion region extraction unit 180.

<Regarding Non-Cell Region>

The non-cell region extraction unit 190 extracts a non-cell region from the image P. Here, the image P also shows a region where no cell is present. The region where no cell is present is, for example, a region where there are no cells in the culture medium or a region where there are no cells within the bottom surface (surface) of the culture vessel 19. The non-cell region extraction unit 190 extracts a region where there are no cells as a non-cell region. The non-cell region area calculation unit 192 calculates an area of the non-cell region extracted by the non-cell region extraction unit 190.

<Regarding Dead Cell Region>

The dead cell region extraction unit 200 extracts a dead cell region from the image P. Here, the cell may become a dead cell because the differentiation is not performed in the differentiation process. The dead cell region extraction unit 200 extracts a region of dead cells among the cells shown in the image P as the dead cell region. The dead cell region area calculation unit 202 calculates an area of the dead cell region extracted by the dead cell region extraction unit 200. Also, the dead cells are, for example, cells in which the appearance of caspase 3, caspase 5, or the like is detected as fluorescence by staining with an existing fluorescent dye and fluorescence is detected by a 4',6-diamidino-2-phenylindole (DAPI) stain.

<Regarding Dying and Dead Cell Region>

The dying and dead cell region extraction unit 210 extracts a dying and dead cell region from the image P. As described above, cells may become dead cells due to low-quality differentiation during a differentiation process. In the following description, cells that are likely to become dead cells with the elapse of time or cells that do not become dead cells and continue to differentiate in a state of live cells by subsequently giving an appropriate environment, an appropriate culture medium, or appropriate additives even if they will be likely to become dead cells are collectively referred to as dying cells. Also, the dying cells are, for example, cells in which the appearance of caspase 3, caspase 5, or the like is detected as fluorescence by staining with an existing fluorescent dye and which is not stained with 4',6-diamidino-2-phenylindole (DAPI) (in which fluorescence based on DAPI is not detected). The dying and dead cell region extraction unit 210 extracts a region where a dying cell region and a dead cell region are combined as a dying and dead cell region. The dying and dead cell region area calculation unit 212 calculates an area of the dying and dead cell region extracted by the dying and dead cell region extraction unit 210.

<Regarding Image Processing on Image P>

Figure 18:
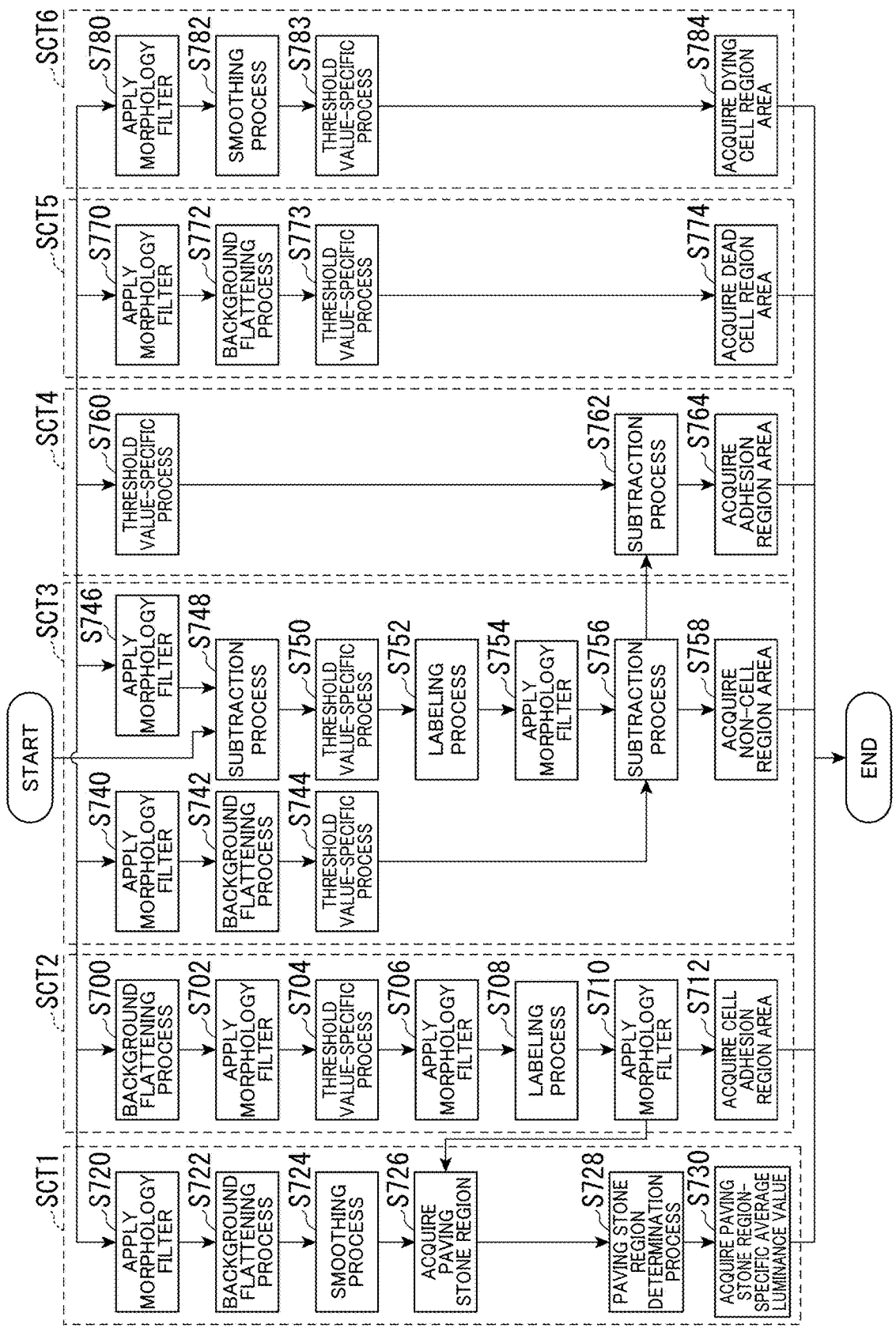
FIG. 18 is a flowchart showing an example of a process of the image determination device of the third embodiment.

FIG. 18 is a flowchart showing an example of a process of the image determination device 10 of the third embodiment. The flowchart shown in FIG. 18 is executed, for example, when the image P is acquired by the acquisition unit 110. The paving stone region extraction unit 160 and the paving stone region-specific average luminance value calculation unit 162 extract a paving stone region according to the processing of steps S720 to S730 on a section SCT1 and calculate an average value of luminance values in the paving stone region. The cell adhesion region extraction unit 180 and the cell adhesion region area calculation unit 182 extract a cell adhesion region according to the processing of steps S700 to S712 on a section SCT2 and calculate an area of the cell adhesion region.

The non-cell region extraction unit 190 and the non-cell region area calculation unit 192 extract a non-cell region according to the processing of steps S740 to S758 on a section SCT3 and calculate an area of the non-cell region. The adhesion region extraction unit 170 and the adhesion region area calculation unit 172 extract an adhesion region according to the processing of steps S760 to S764 on a section SCT4 and calculate an area of the adhesion region. The dead cell region extraction unit 200 and the dead cell region area calculation unit 202 extract a dead cell region according to the processing of steps S770 to S774 on a section SCT5 and calculate an area of the dead cell region. The dying and dead cell region extraction unit 210 and the dying and dead cell region area calculation unit 212 extract a dying and dead cell region according to the processing of steps S780 to S784 on a section SCT6 and calculate an area of the dying and dead cell region.

In the present embodiment, a case where the image determination device 10 calculates any one of the average value of the luminance values in the paving stone region, the area of the adhesion region, the area of the cell adhesion region, the area of the non-cell region, the area of the dead cell region, and the area of the dying and dead cell region will be described. That is, the image determination device 10 executes the processing of any one of steps S700 to S784 shown in FIG. 18. Also, when the image determination device 10 calculates any one of the average value of the luminance values in the paving stone region, the area of the adhesion region, the area of the cell adhesion region, the area of the non-cell region, the area of the dead cell region, and the area of the dying and dead cell region, a configuration in which the section SCT according to a calculation target among the sections SCT1 to SCT6 is executed may be adopted.

<Regarding Brightness of Each Part Shown in Image P>

Figure 19:
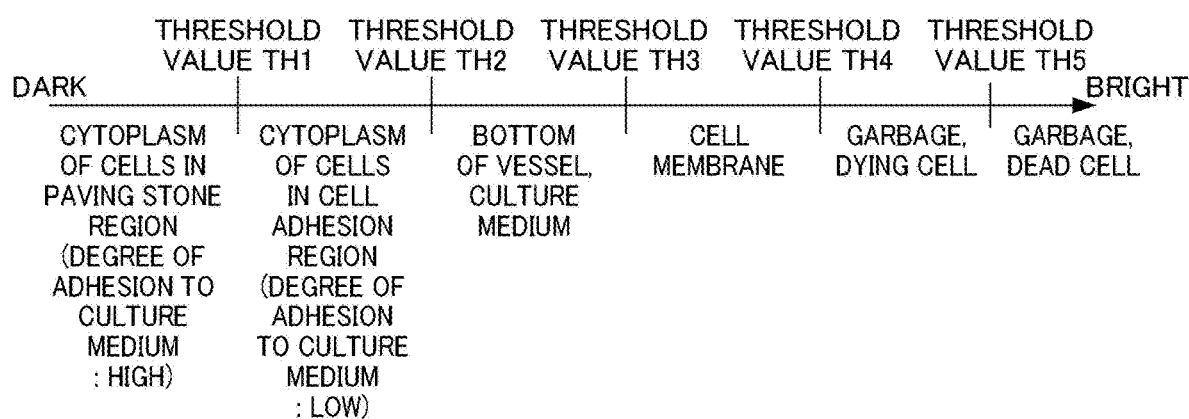
FIG. 19 is a diagram showing an overview of light and shade of each part shown in an image P.

Hereinafter, the light and shade of each pixel constituting the image P will be described before description of details of the processing on each section SCT. FIG. 19 is a diagram showing an overview of light and shade of each pixel constituting the image P. As described above, the image P imaged by the imaging device 34 provided in the culture observation device 11 of the present embodiment is a phase difference image in which a phase shift of light is detected as a contrast. A darkest portion imaged in this image P is the cytoplasm of the cells that adhere to the culture vessel. Also, the cytoplasm of cells (i.e., the cytoplasm of cells in the paving stone region) whose degree of adhesion to the culture vessel (hereinafter referred to as a degree of adhesion) is high among the cells that adhere to the culture vessel is imaged to be darker than the cytoplasm of cells (i.e., the cytoplasm of cells in the cell adhesion region) having a low degree of adhesion. As shown in FIG. 19, the luminance of the pixel showing the cytoplasm of a cell having a high degree of adhesion is luminance less than a threshold value TH1 and the luminance of the pixel showing the cytoplasm of a cell having a low degree of adhesion is luminance greater than or equal to the threshold value TH1.

Next to the cytoplasm, a darkest portion that is imaged is the bottom surface of the culture vessel 19 or the culture medium. As shown in FIG. 19, the luminance of the pixel showing the cytoplasm of the cell (i.e., the cytoplasm of the cell in the cell adhesion region) having a low degree of adhesion is luminance less than a threshold value TH2 and the luminance of the pixel showing the bottom surface of the culture vessel 19 or the culture medium is luminance greater than or equal to the threshold value TH2. The threshold value TH1 and the threshold value 112 have a relationship of threshold value TH1<threshold value TH2. Next to the bottom surface of the culture vessel 19 or the culture medium, a darkest portion that is imaged is the cell membrane of the cell. As shown in FIG. 19, the luminance of the pixel showing the bottom surface of the culture vessel 19 or the culture medium is luminance less than a threshold value TH3 and the luminance of the pixel showing the cell membrane of the cell is luminance greater than or equal to the threshold value TH3. The threshold value TH2 and the threshold value TH3 have a relationship of threshold value TH2<threshold value TH3.

Next to the cell membrane of the cell, a darkest portion that is imaged is garbage generated when the culture medium is replaced, cell residue generated when the cell is crushed, or a dying cell. As shown in FIG. 19, the luminance of the pixel showing the cell membrane of the cell is luminance less than a threshold value TH4 and the luminance of the pixel showing garbage generated when the culture medium is replaced, cell residue generated when the cell is crushed, or a dying cell is luminance greater than or equal to the threshold value TH4. The threshold value TH3 and the threshold value TH4 have a relationship of threshold value TH3<threshold value TH4. A brightest portion imaged in this image P is garbage generated when the culture medium is replaced, cell residue generated when the cell is crushed, or a dead cell. As shown in FIG. 19, the luminance of the pixel showing garbage generated when the culture medium is replaced, cell residue generated when the cell is crushed, or a dying cell is luminance less than the threshold value TH5 and the luminance of the pixel showing garbage generated when the culture medium is replaced, cell residue generated when the cell is crushed, or a dead cell is luminance greater than or equal to the threshold value TH5. The threshold value TH4 and the threshold value TH5 have a relationship of threshold value TH4<threshold value TH5. The above description of light and shade is reversed according to whether a phase difference caused when diffracted light passing through the phase plate and direct light not passing through the phase plate interfere with each other when cells are imaged is a weakening phase difference (½ wavelength) or a strengthening phase difference (0 wavelengths).

<Regarding Section SCT2: Image Processing on Cell Adhesion Region>

Details of each section SCT will be described below with reference to FIG. 18. Because data acquired in the section SCT2 is used for processing on the section SCT1, the section SCT2 will first be described and then description will be given in the order of the section SCT1 and the sections SCT3 to 6.

In the section SCT2, the cell adhesion region extraction unit 180 performs a process of flattening the background of an image P with respect to the image P acquired by the acquisition unit 110 (step S700) and applies the morphology filter (step S702). Also, the process of flattening the background of the image P is, for example, the existing image processing for limiting the variation in a luminance value of the background of the image P. Here, the image P includes a region having high luminance caused by garbage generated when the culture medium is replaced, shot noise at the time of imaging by the imaging device 34, or the like. In the section SCT2, the cell adhesion region extraction unit 180 performs a process of making an image of a structure finer than the cell adhesion region (for example, an image of a fine structure or the like within the cytoplasm such as an organelle) existing in the image P inconspicuous while correcting the luminance value of the image P so that a region having high luminance is inconspicuous according to steps S700 and S702.

Subsequently, the cell adhesion region extraction unit 180 performs a threshold value-specific process on the image P and extracts a region having a luminance value less than or equal to the luminance value of the cell adhesion region (step S704). As described above, the cell adhesion region is a region where cells whose quality of differentiation is low or cells that are undergoing differentiation are densely packed. Therefore, in step S704, the cell adhesion region extraction unit 180 extracts a region of the image P having a luminance value less than the threshold value TH2. Subsequently, the cell adhesion region extraction unit 180 applies the morphology filter to clarify the extracted region (step S706).

Subsequently, the cell adhesion region extraction unit 180 performs a labeling process for the region clarified by the morphology filter (step S708). The cell adhesion region extraction unit 180 can extract pixels labeled in the labeling process as a region and fill the missing pixels generated in the region with the extracted pixels. The missing pixels are, for example, a portion (for example, about several pixels) of the cell adhesion region having a luminance value greater than the threshold value TH2, and is a portion not extracted in step S704. Also, when a labeling value (i.e., an area of the region) of the region labeled in the labeling process does not match a value according to a size (an area) of the cell adhesion region (for example, excessively large), the cell adhesion region extraction unit 180 excludes the region from an extraction target. Here, in step S704, the extracted region of the luminance value less than the threshold value TH2 includes a cytoplasmic region of the cell having a paving stone-shaped form (see FIG. 19). Generally, the cell adhesion region is a region smaller than the paving stone region. Therefore, the cell adhesion region extraction unit 180 excludes the paving stone region by excluding a region (for example, excessively large) that does not match the value according to the size (the area) of the cell adhesion region from the extracted region in the labeling process. Subsequently, the cell adhesion region extraction unit 180 applies the morphology filter to make the contour of the extracted region clearer (step S710). The cell adhesion region extraction unit 180 can extract the cell adhesion region according to the processing of steps S700 to S710 described above.

Figure 20:
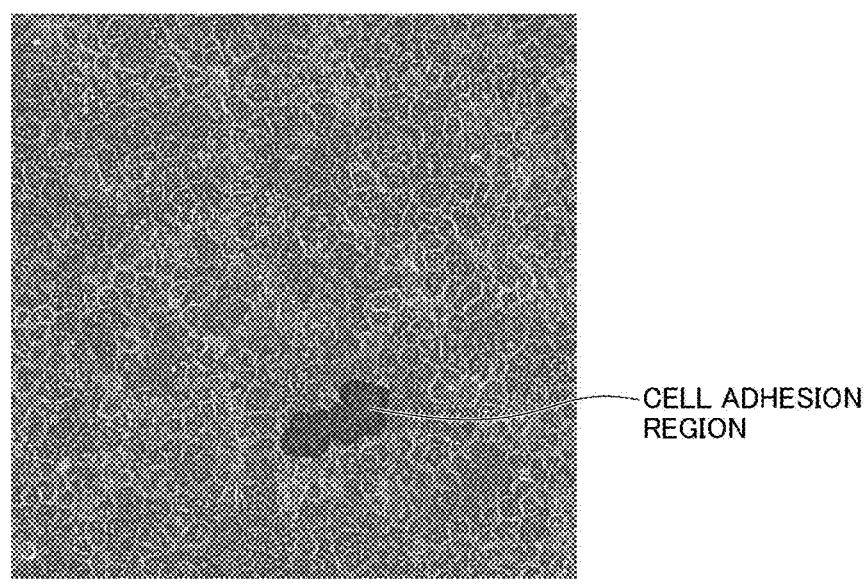
FIG. 20 is a diagram showing an example of a cell adhesion region.

FIG. 20 is a diagram showing an example of a cell adhesion region. The cell adhesion region extraction unit 180 can extract the cell adhesion region as shown in FIG. 20 by performing the above-described processing of steps S700 to S710 on the image P. Returning to FIG. 18, the cell adhesion region area calculation unit 182 calculates an area of the cell adhesion region extracted by the cell adhesion region extraction unit 180 (step S712).

<Section SCT1: Image Processing on Paving Stone Region>

In the section SCT1, the paving stone region extraction unit 160 applies the morphology filter to the image P acquired by the acquisition unit 110 (step S720), performs a process of flattening the background of the image P (step S722), and performs a process of smoothing the entire image P (step S724). The paving stone region extraction unit 160 performs a process of making an image of a structure finer than a cell having the paving stone-shaped form (for example, an image of a fine structure or the like within the cytoplasm such as an organelle) existing in the image P inconspicuous while correcting the luminance value of the image P so that a region having high luminance caused by garbage generated when the culture medium is replaced, shot noise at the time of imaging by the imaging device 34, or the like is inconspicuous to clarify a region of cells having a paving stone-shaped form according to the processing of steps S720 to S724.

Subsequently, the paving stone region extraction unit 160 acquires a cell adhesion region extracted by the cell adhesion region extraction unit 180 performing the processing of steps S700 to S710 on the section SCT2 and extracts a region matching a region other than the cell adhesion region. In the region, a region having a luminance value greater than or equal to a prescribed threshold value is extracted (step S726). Subsequently, the paving stone region extraction unit 160 determines whether or not cells have formed the paving stone region (step S728).

Here, the paving stone region extraction unit 160 determines whether or not cells have formed the paving stone region on the basis of, for example, an average value obtained by averaging differences between luminance values in the cytoplasm of the cells imaged in the image P and luminance values in the cell membranes with respect to all cells imaged in the image P. The paving stone region extraction unit 160 determines that cells have formed the paving stone region when the average value is greater than or equal to a prescribed threshold value (for example, a threshold value obtained by subtracting a prescribed constant from the threshold value calculated as the paving stone region-specific average luminance threshold value or the paving stone region-specific average luminance threshold value in the region within the image P). On the other hand, when the average value is less than a prescribed threshold value, the paving stone region extraction unit 160 determines that cells have not formed the paving stone region. Also, the paving stone region extraction unit 160 may determine that cells have formed the paving stone region, for example, when an area of the paving stone region extracted from the image P is larger than a prescribed value.

Subsequently, the paving stone region-specific average luminance value calculation unit 162 calculates an average value of luminance values of the pixels showing the paving stone region extracted by the paving stone region extraction unit 160 (luminance values of pixels showing a region of cells having a paving stone-shaped form) (step S730).

Figure 21:
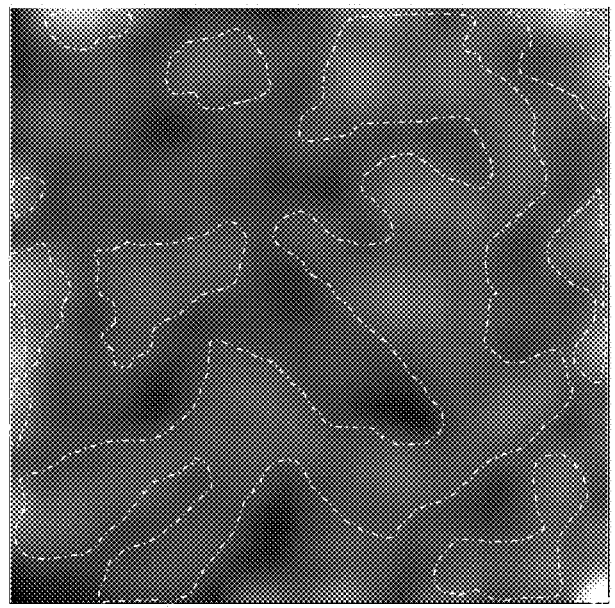
FIG. 21 is a diagram showing an example of a paving stone region.

FIG. 21 is a diagram showing an example of a paving stone region (a region surrounded by an alternate long and short dash line) extracted by the paving stone region extraction unit 160 through step S726. The paving stone region extraction unit 160 can reduce a luminance value difference between the cell membrane and the cytoplasm between which the luminance value difference is larger in the cells having the paving stone-shaped form on the image P by performing the above-described processing of steps S720 to S726 on the image P and facilitate a threshold value comparison process. Also, in the example shown in FIG. 21, a portion having a high-luminance value is indicated by a light color and a portion having a low-luminance value is indicated by a dark color.

<Section SCT3: Image Processing on Non-Cell Region>

In the section SCT3, the non-cell region extraction unit 190 applies the morphology filter to the image P acquired by the acquisition unit 110 (step S740) and performs a process of flattening the background of the image P (step S742). The non-cell region extraction unit 190 performs a process of making an image of a structure finer than the paving stone region and the cell adhesion region (for example, an image of a fine structure or the like within the cytoplasm such as an organelle) existing in the image P inconspicuous while correcting the luminance value of the image P so that a region having high luminance caused by garbage generated when the culture medium is replaced, shot noise at the time of imaging by the imaging device 34, or the like is inconspicuous according to the processing of steps S740 and S742. Subsequently, the non-cell region extraction unit 190 performs a threshold value-specific process on the image P and extracts a region having luminance less than or equal to that of the cytoplasm of the cell having a low degree of adhesion (step S744). Specifically, the non-cell region extraction unit 190 extracts a region of pixels having a luminance value less than the threshold value TH2 (i.e., the cytoplasm of the paving stone region and the cytoplasm of the cell adhesion region) in the image P.

Figure 22:
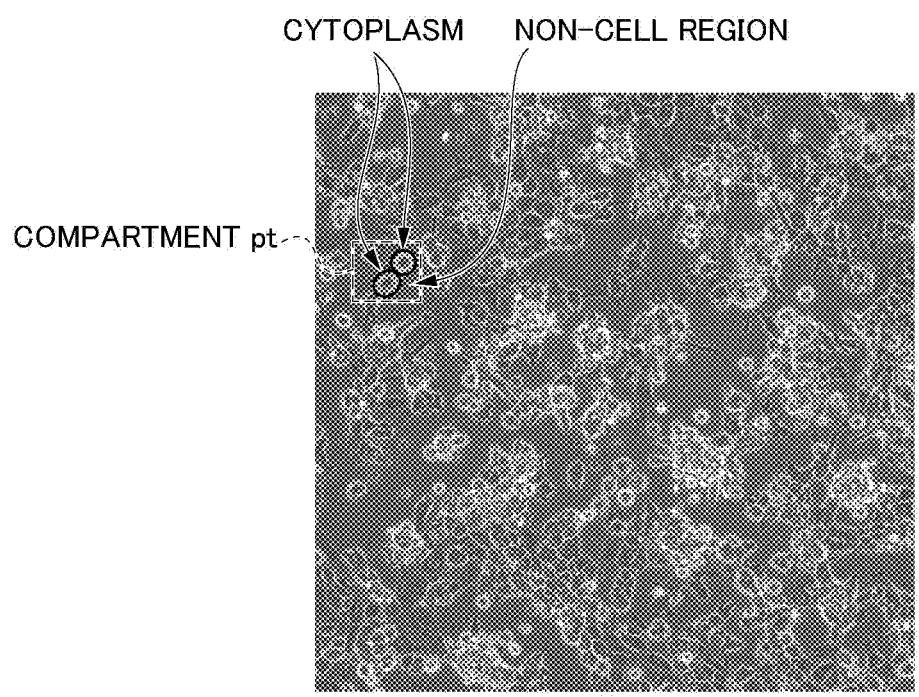
FIG. 22 is a diagram showing an example of a region extracted in step S744.

FIG. 22 is a diagram showing an example of a region to be extracted in step S744. As shown in a compartment pt of FIG. 22, the luminance values in the cytoplasm of the paving stone region and the cytoplasm of the cell adhesion region among the cytoplasm of the paving stone region, the cytoplasm of the cell adhesion region, and the non-cell region are less than the luminance value in the non-cell region. In step S744, regions of the cytoplasm of the paving stone region and the cytoplasm of the cell adhesion region are extracted. The regions extracted in step S744 are used in the processing of step S756 to be described below.

Figure 23:
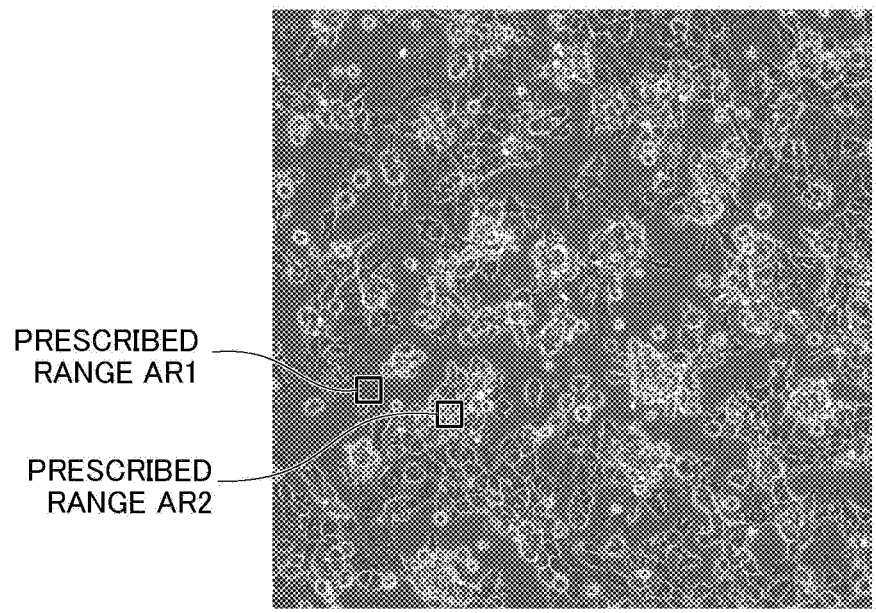
FIG. 23 is a diagram conceptually showing a local change.

Subsequently, the non-cell region extraction unit 190 applies the morphology filter to clarify a portion where a local change is large in the image P (step S746). FIG. 23 is a diagram conceptually showing local changes. In FIG. 23, two prescribed ranges (prescribed ranges AR1 and AR2 shown in FIG. 23) among prescribed ranges (hereinafter, prescribed ranges AR) are shown in the image P. In FIG. 23, the prescribed range AR1 is set in, for example, a non-cell region or a cell region having relatively large cytoplasm in the image P and the prescribed range AR2 is set in a region (for example, a paving stone region, a cell adhesion region, an adhesion region, or the like) where there are cells in the image P. As shown in FIG. 23, in general, a change in the luminance value between adjacent pixels is larger (i.e., a local change is larger) with respect to pixels within the prescribed range AR2 among pixels within the prescribed range AR1 which is a non-cell region or a cell region having relatively large cytoplasm and pixels within the prescribed range AR2 of a region where there are cells of a paving stone-shaped form or the like. In step S746, the non-cell region extraction unit 190 clarifies the portion where the local change is large (i.e., the region where there are cells) in the image P.

Subsequently, the non-cell region extraction unit 190 performs a subtraction process of subtracting a region where a portion having a large local change is clarified in step S746 from the image P acquired by the acquisition unit 110 (step S748). Specifically, the non-cell region extraction unit 190 acquires a portion obtained by subtracting the portion having the large local change from the image P. Thereby, the non-cell region extraction unit 190 can acquire a region having a small local change (i.e., a non-cell region or a region of a cell having large cytoplasm).

Subsequently, the non-cell region extraction unit 190 performs a threshold value-specific process on a region having a small local change acquired according to the processing of steps S746 and S748 and extracts a region having a luminance value less than or equal to the luminance value of the non-cell region (step S750). Here, a region having a small local change may also not be a non-cell region (for example, a region of a cell having large cytoplasm or the like). In step S750, the non-cell region extraction unit 190 can exclude a region (for example, a cell region with large cytoplasm or the like) that is not the non-cell region by extracting a region having a luminance value less than the threshold value TH3 from among regions having small local changes acquired according to the processing of steps S746 and S748.

Subsequently, the non-cell region extraction unit 190 performs a labeling process for the regions extracted according to the processing of steps S746 to S750 (step S752). By performing the labeling process, the missing pixels occurring in the extracted region are filled in. These missing pixels are, for example, a portion having a luminance value greater than the threshold value TH3 only for a part (for example, about several pixels) within a region having a small local change. Subsequently, the non-cell region extraction unit 190 applies the morphology filter and makes the contour of the region filled with the missing pixels clearer (step S754).

The cell adhesion region extraction unit 180 can extract a region having a small local change and a luminance value less than the threshold value TH3 according to the processing of steps S746 to S754 described above.

Subsequently, the non-cell region extraction unit 190 performs a subtraction process of subtracting a region having a luminance value less than the threshold value TH2 extracted according to the processing of steps S740 to S744 from a region having a luminance value less than the threshold value TH3 extracted according to the processing of steps S746 to S754 described above (step S756). As shown in FIG. 19, the bottom surface of the culture vessel 19 or the region of the culture medium (i.e., the non-cell region) can be extracted by subtracting the region having the luminance value less than the threshold value TH2 from the region having the luminance value less than the threshold value TH3.

Figure 24:
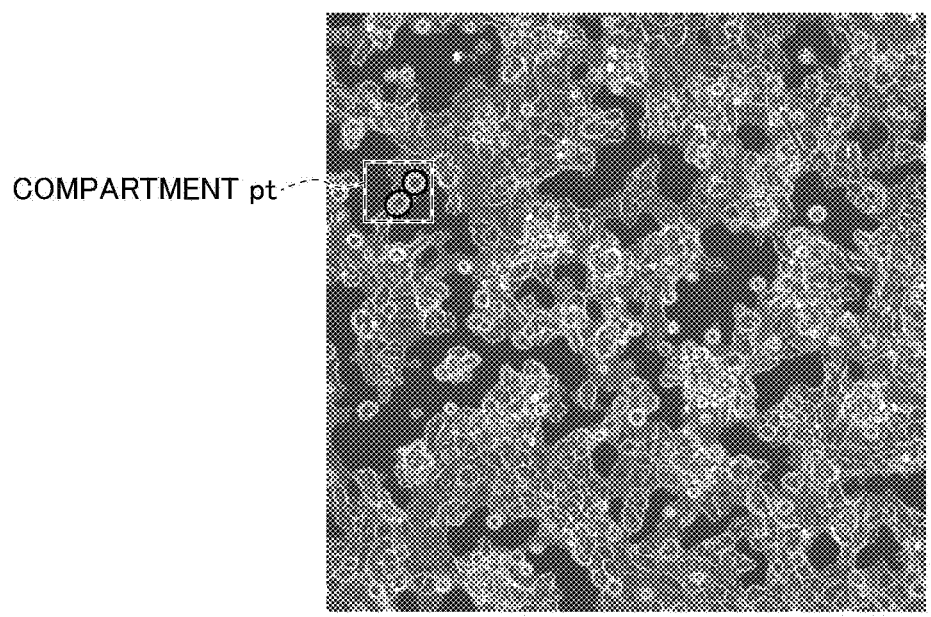
FIG. 24 is a diagram showing an example of a non-cell region.

FIG. 24 is a diagram showing an example of a non-cell region. In FIG. 24, a non-cell region (a darkly colored region shown in FIG. 24) is shown in the image P. Also, a compartment pt shown in FIG. 24 shows the same position as the compartment pt shown in FIG. 22. As shown in the compartment pt of FIG. 24, the non-cell region does not include the cytoplasmic region of the cell because the cytoplasmic region is subtracted in step S756. Returning to FIG. 18, the non-cell region area calculation unit 192 calculates an area of the non-cell region extracted by the non-cell region extraction unit 190 (step S758).

<Section SCT4: Image Processing on Adhesion Region>

In the section SCT4, the adhesion region extraction unit 170 performs a threshold value-specific process of extracting a region having a luminance value less than the threshold value TH3 from the image P acquired by the acquisition unit 110 (step S760). As described above, the region having the luminance value less than the threshold value TH3 includes an adhesion region and a non-cell region (see FIG. 19). Subsequently, the adhesion region extraction unit 170 acquires the non-cell region extracted by the non-cell region extraction unit 190 according to the processing of steps S740 to S756 and performs a subtraction process of subtracting the non-cell region from the region having the luminance value less than the threshold value TH3 (step S762).

Figure 25:
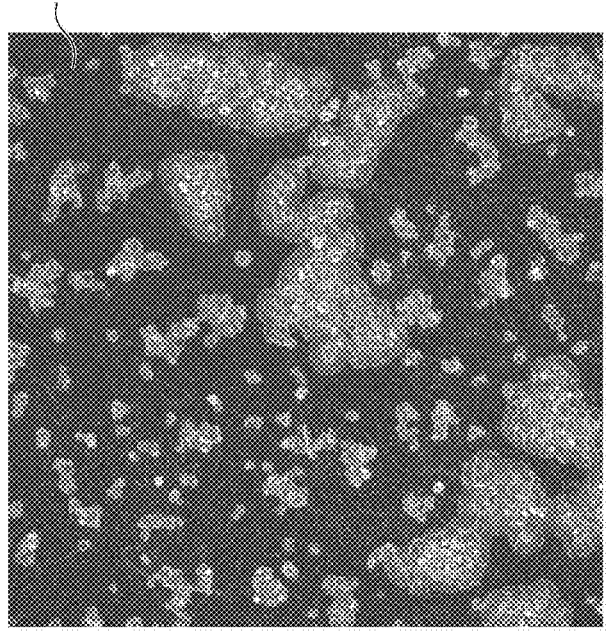
FIG. 25 is a diagram showing an example of an adhesion region.

FIG. 25 is a diagram showing an example of an adhesion region. In FIG. 25, the adhesion region (an adhesion region AR3 shown in FIG. 25) is shown in the image P. Returning to FIG. 18, the adhesion region area calculation unit 172 subsequently calculates an area of the adhesion region extracted by the adhesion region extraction unit 170 (step S764).

<Section SCT5: Image Processing on Dead Cell Region>

In the section SCT5, the dead cell region extraction unit 200 applies the morphology filter to the image P acquired by the acquisition unit 110 (step S770) and performs a process of flattening the background of the image P (step S772). The dead cell region extraction unit 200 performs a process of making an image of a structure finer than a dead cell (for example, an image of a fine structure or the like within the cytoplasm such as an organelle) existing in the image P inconspicuous while correcting the luminance value of the image P so that a region having high luminance caused by garbage generated when the culture medium is replaced, shot noise at the time of imaging by the imaging device 34, or the like is inconspicuous to clarify a dead cell region according to the processing of steps S770 and S772.

Figure 26:
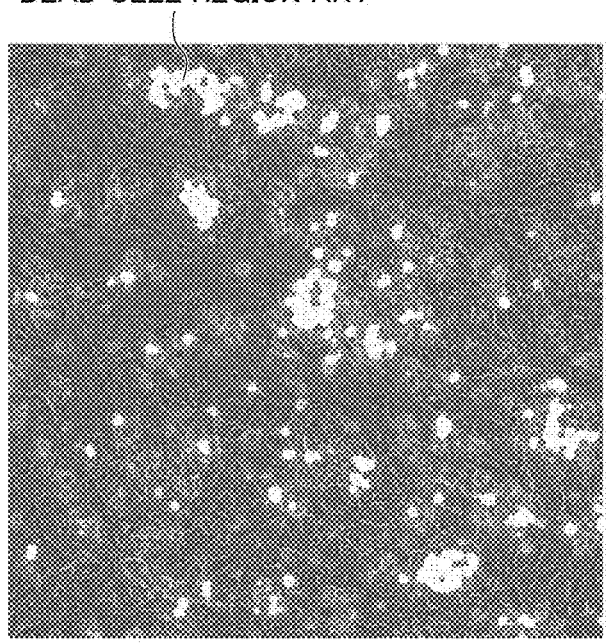
FIG. 26 is a diagram showing an example of a dead cell region.

Subsequently, the dead cell region extraction unit 200 performs a threshold value-specific process for the image P and extracts a region having luminance higher than or equal to that of the dead cell region (step S773). Specifically, the dead cell region extraction unit 200 extracts a region of pixels having a luminance value greater than or equal to the threshold value TH5 in the image P. FIG. 26 is a diagram showing an example of a dead cell region. In FIG. 26, the dead cell region (a dead cell region AR4 shown in FIG. 26) is shown in the image P. Returning to FIG. 18, the dead cell region area calculation unit 202 subsequently calculates an area of the dead cell region extracted by the dead cell region extraction unit 200 (step S774).

<Section SCT6: Image Processing on Dying and Dead Cell Region>

In the section SCT6, the dying and dead cell region extraction unit 210 applies the morphology filter to the image P acquired by the acquisition unit 110 (step S780) and performs a process of flattening the background of the image P (step S782). The dying and dead cell region extraction unit 210 performs a process of making an image of a structure finer than a dying and dead cell region (for example, an image of a fine structure or the like within the cytoplasm such as an organelle) existing in the image P inconspicuous while correcting the luminance value of the image P so that a region having high luminance caused by garbage generated when the culture medium is replaced, shot noise at the time of imaging by the imaging device 34, or the like is inconspicuous to clarify the dying and dead cell region according to the processing of steps S780 and S782. Thereby, the dying and dead cell region extraction unit 210 can clarify the dying and dead cell region.

Figure 27:
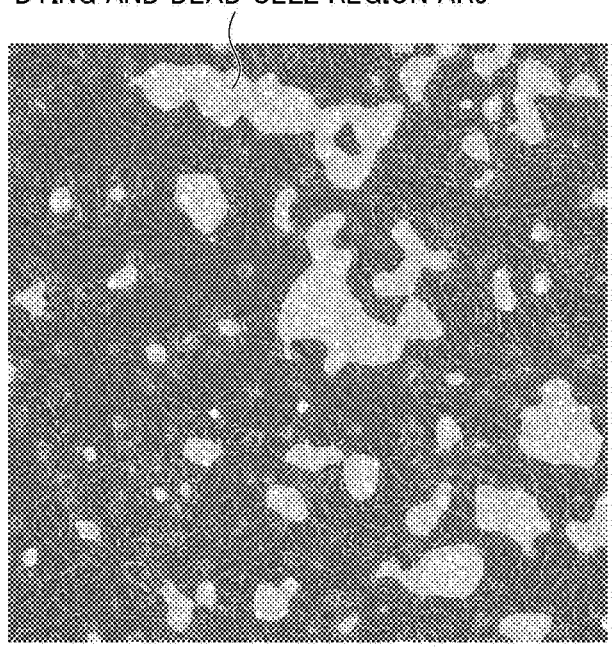
FIG. 27 is a diagram showing an example of a dying and dead cell region.

Subsequently, the dying and dead cell region extraction unit 210 performs a threshold value-specific process for the image P and extracts a region having luminance higher than or equal to that of the dying and dead cell region (step S783). Specifically, the dying and dead cell region extraction unit 210 extracts a region of a pixel having a luminance value greater than or equal to the threshold value TH4 in the image P. FIG. 27 is a diagram showing an example of a dying and dead cell region. In FIG. 27, a dying and dead cell region (a dying and dead cell region AR5 shown in FIG. 27) is shown in the image P. Returning to FIG. 18, the dying and dead cell region area calculation unit 212 subsequently calculates an area of the dying and dead cell region extracted by the dying and dead cell region extraction unit 210 (step S784).

Also, the extraction process for each region in the above-described sections SCT1 to SCT6 is an example and the present invention is not limited thereto. The combination and order of region extraction processes may be changed as appropriate, all or some extraction processes may be replaced with other existing image processing, or the other existing image processing may be added to the extraction processes.

<Regarding Determination Unit 220: Determination Based on Average Value of Luminance Values in Paving Stone Region>

The determination unit 220 determines the quality of cell differentiation on the basis of the average value of the luminance values in the paving stone region calculated by the paving stone region-specific average luminance value calculation unit 162 and the paving stone region-specific average luminance threshold value 301a stored in the storage unit 301. Here, the paving stone region-specific average luminance threshold value 301a is a threshold value for the average value of the luminance values in the paving stone region. The determination unit 220 determines the quality of cell differentiation by comparing the average value of the luminance values in the paving stone region with the paving stone region-specific average luminance threshold value 301a. For example, the determination unit 220 determines that the quality of cell differentiation is high when the acquired average luminance value of the paving stone region is greater than or equal to the average value of the luminance values in the paving stone region indicated by the paving stone region-specific average luminance threshold value 301a and determines that the quality of cell differentiation is low when the acquired average luminance value of the paving stone region is less than the average value of the luminance values in the paving stone region indicated by the paving stone region-specific average luminance threshold value 301a.

Here, as described above, the paving stone region-specific average luminance threshold value 301a is a value predetermined by comparing an index based on an image P in which the cell observer observes cells and a cell determined to be a normal mature hepatocyte is imaged with an index based on an image P in which the cell observer observes cells and a cell determined not to be a normal mature hepatocyte is imaged. That is, the paving stone region-specific average luminance threshold value 301a is a value based on a result of determining the quality of differentiation in a time-lapse image. Therefore, the determination unit 220 determines the quality of cell differentiation by comparing an index value based on the time-lapse image (the average value of the luminance values in the paving stone region) with an index value based on the result of determining the quality of differentiation in the time-lapse image (the paving stone region-specific average luminance threshold value 301a).

<Regarding Determination Unit 220: Determination Based on Adhesion Region>

Also, the determination unit 220 determines the quality of cell differentiation on the basis of the area of the adhesion region calculated by the adhesion region area calculation unit 172 and the adhesion region area-specific threshold value 301b stored in the storage unit 301. Here, the adhesion region area-specific threshold value 301b is a threshold value for the area of the adhesion region. For example, the determination unit 220 determines that the quality of cell differentiation is high when the value of the acquired area of the adhesion region is a value greater than or equal to the threshold value for the area of the adhesion region indicated by the adhesion region area-specific threshold value 301b and determines that the quality of cell differentiation is low when the value of the acquired area of the adhesion region is a value less than the threshold value for the area of the adhesion region indicated by the adhesion region area-specific threshold value 301b.

<Regarding Determination Unit 220: Determination Based on Cell Adhesion Region>

Also, the determination unit 220 determines the quality of cell differentiation on the basis of the area of the cell adhesion region calculated by the cell adhesion region area calculation unit 182 and the cell adhesion region area-specific threshold value 301c stored in the storage unit 301. Here, the cell adhesion region area-specific threshold value 301c is a threshold value for the area of the cell adhesion region. For example, the determination unit 220 determines that the quality of cell differentiation is low when the value of the acquired area of the cell adhesion region is a value greater than or equal to the threshold value for the area of the cell adhesion region indicated by the cell adhesion region area-specific threshold value 301c and determines that the quality of cell differentiation is high when the value of the acquired area of the cell adhesion region is a value less than the threshold value for the area of the cell adhesion region indicated by the cell adhesion region area-specific threshold value 301c.

<Determination Unit 220: Determination Based on Non-Cell Region>

Also, the determination unit 220 determines the quality of cell differentiation on the basis of an area of the non-cell region calculated by the non-cell region area calculation unit 192 and the non-cell region area-specific threshold value 301d stored in the storage unit 301. Here, the non-cell region area-specific threshold value 301d is a threshold value for the area of the non-cell region. For example, the determination unit 220 determines that the quality of cell differentiation is low when the value of the acquired area of the non-cell region is a value greater than or equal to the threshold value for the area of the non-cell region indicated by the non-cell region area-specific threshold value 301d and determines that the quality of cell differentiation is high when the value of the acquired area of the non-cell region is a value less than the threshold value for the area of the non-cell region indicated by the non-cell region area-specific threshold value 301d.

<Determination Unit 220: Determination Based on Dead Cell Region>

Also, the determination unit 220 determines the quality of cell differentiation on the basis of the area of the dead cell region calculated by the dead cell region area calculation unit 202 and the dead cell region area-specific threshold value 301e stored in the storage unit 301. Here, the dead cell region area-specific threshold value 301e is a threshold value for the area of the dead cell region. For example, the determination unit 220 determines that the quality of cell differentiation is low when the value of the acquired area of the dead cell region is a value greater than or equal to the threshold value for the area of the dead cell region indicated by the dead cell region area-specific threshold value 301e and determines that the quality of cell differentiation is high when the value of the acquired area of the dead cell region is a value less than the threshold value for the area of the dead cell region indicated by the dead cell region area-specific threshold value 301e.

<Determination Unit 220: Determination Based on Dying and Dead Cell Regions>

Also, the determination unit 220 determines the quality of cell differentiation on the basis of the area of the dying and dead cell region calculated by the dying and dead cell region area calculation unit 212 and the dying and dead cell region area-specific threshold value 301f stored in the storage unit 301. Here, the dying and dead cell region area-specific threshold value 301f is a threshold value for the area of the dying and dead cell region. For example, the determination unit 220 determines that the quality of the cell differentiation is low when the value of the acquired area of the dying and dead cell region is a value greater than or equal to the threshold value for the area of the dying and dead cell region indicated by the dying and dead cell region area-specific threshold value 301f and determines that the quality of the cell differentiation is high when the value of the acquired area of the dying and dead cell region is a value less than the threshold value for the area of the dying and dead cell region indicated by the dying and dead cell region area-specific threshold value 301f.

<Regarding Output Unit 230>

The output unit 230 outputs a determination result in a determination process of the determination unit 220. The output unit 230 is, for example, a display device including a liquid crystal display panel or an organic electroluminescence (EL) display panel. Also, the output unit 230 is connected to, for example, a collection device for collecting the determination result via a network, and outputs the determination result in the determination process of the determination unit 220 to the collection device. This collection device is, for example, a terminal device used by a referrer who refers to a result of determining the quality of cell differentiation, and may be implemented by a portable communication terminal device such as a smartphone or a tablet-type computer (a tablet PC) or may be implemented by a stationary personal computer or the like.

Also, when the magnification of a lens of the imaging device 34 and the resolution of the image P are predetermined, the adhesion region area calculation unit 172, the cell adhesion region area calculation unit 182, the non-cell region area calculation unit 192, the dead cell region area calculation unit 202, and the dying and dead cell region area calculation unit 212 may be configured to supply the number of pixels indicating the extracted region as an area to the determination unit 220. In this case, the adhesion region area-specific threshold value 301b, the cell adhesion region area-specific threshold value 301c, the non-cell region area-specific threshold value 301d, the dead cell region area-specific threshold value 301e, and the dying and dead cell region area-specific threshold value 301f are threshold values for the number of pixels and the determination unit 220 determines the quality of cell differentiation on the basis of the number of pixels calculated in each functional unit and the threshold value for the number of pixels stored in the storage unit 301.

<Regarding Effect Quantity r>

Here, it may be preferable to use an image P of cells imaged by the imaging device 34 at a specific time in a process in which each functional unit extracts each region and a process of calculating each value. Hereinafter, a process in which the effect quantity calculation unit 219 calculates an effect quantity r in the paving stone region and identifies an image P suitable for use in an evaluation process of the determination unit 220 will be described as an example. Because a process of calculating the effect quantity r in the other regions in the effect quantity calculation unit 219 is basically similar, description thereof will be omitted.

As described above, the imaging device 34 generates an image P according to time-lapse observation in a series of culture processes (for 21 days of the first to fourth differentiation-inducing processes). In the storage unit 301, for example, the time when the image P was acquired by the imaging device 34 and the average value of the luminance values in the paving stone region calculated by the paving stone region-specific average luminance value calculation unit 162 using the image P acquired at the time are stored in association with each other. The observer determines the quality of cell differentiation by observing the final image P (for example, an image after 21 days from the start of the culture process when the culture process ends in the 21 days) among a plurality of images P stored in the storage unit 301. Hereinafter, it is assumed that the determination results of the observer are all associated with the plurality of images P related to the series of culture processes stored in the storage unit 301.

Here, the plurality of images P are time-lapse images each associated with the time when the image P is acquired by the imaging device 34 (i.e., the elapsed time from the start of the culture process). Also, the average value of the luminance values in the paving stone region is an index value calculated on the basis of the image P. Therefore, the index value for determining the quality of differentiation in the time-lapse image is calculated from the time-lapse image in which the elapsed time from the start of the culture process and the result of determining the quality of differentiation are associated.

Also, the observer may not observe the final image P and determine the quality of cells. Although it is desirable to make the determination using the image P acquired near the time when the culture process ends, the determination may be made using the image P acquired at any time after the start of the culture process. Also, the observer may not determine the quality of cell differentiation by observing the cells. The observer may make the determination using, for example, an existing biochemical index. In this case, for example, the determination may be made in an ELISA method.

The effect quantity r is an index indicating the accuracy (effect) of a certain index (for example, an evaluation index such as an average value of the luminance values in the paving stone region in the present embodiment) with respect to a process of determining a certain phenomenon (the quality of differentiation into cells in the present embodiment). When the effect quantity r is calculated, the effect quantity calculation unit 219 calculates the effect quantity r using Eq. (1) when the number of images P determined by the observer to have high-quality cell differentiation among the images P stored in the storage unit 301 is set as the number of successful groups $n_1$ and the number of images P determined by the observer to have low-quality cell differentiation is set as the number of unsuccessful groups $n_2$. For example, the number of successful groups $n_1$ is the number of images P for which a ratio of the number of normal mature hepatocytes to the final number of cells is determined to be higher than or equal to a standard ratio (for example, 80%) and the number of unsuccessful groups $n_2$ is the number of images P for which the ratio of the number of normal mature hepatocytes to the final number of cells is determined to be lower than the standard ratio. A method of sorting the successful group and the unsuccessful group is not limited to the ratio between the numbers and the existing sorting method can be applied. For example, a sorting process may be performed on the basis of the shape of the final cell (for example, on the basis of a shape bias).

[Math. 1]

$$r = \frac{z}{\sqrt{(n_1 + n_2)}} \quad (1)$$

A test statistic z is a value based on the standard normal distribution and is a value acquired on the basis of a significance probability (a p value). Therefore, the accuracy of a process of determining a phenomenon increases as the value of the effect quantity r increases. Therefore, preferably, the image P at the time when the value of the effect quantity r is large is used for the determination process of the determination unit 220.

Figure 28:
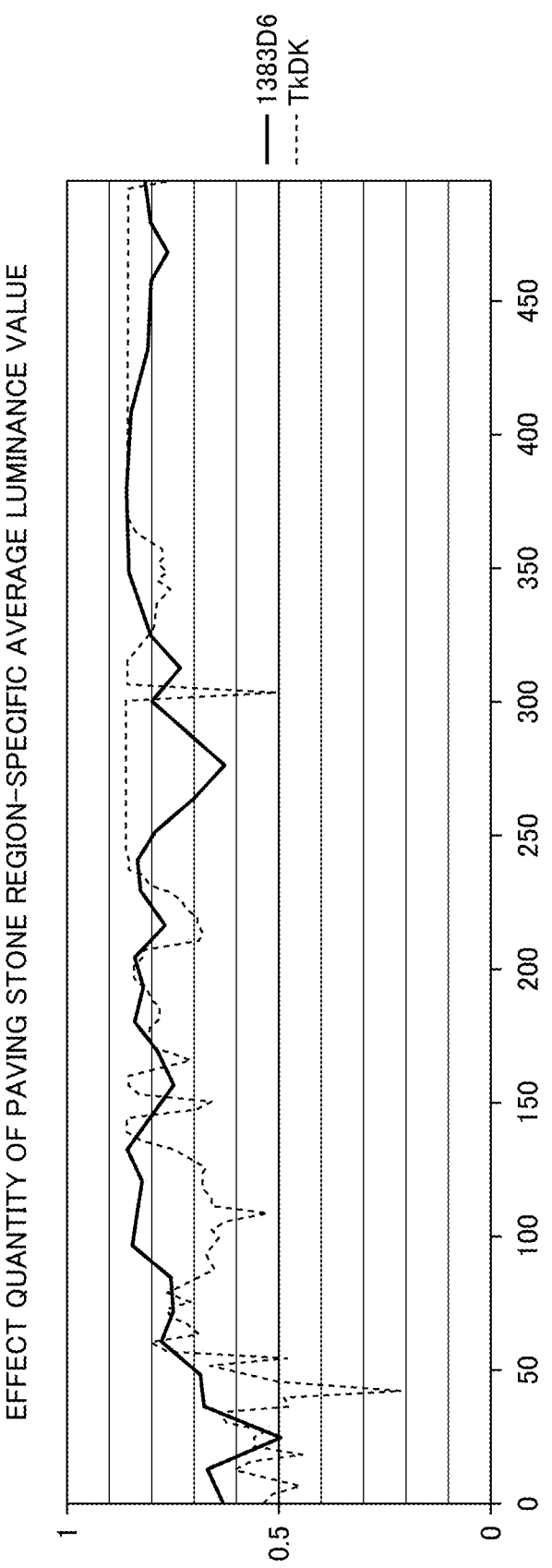
FIG. 28 is a diagram showing an example of an effect quantity of an average value of luminance values in the paving stone region.

FIG. 28 is a diagram showing an example of the effect quantity (hereinafter referred to as the effect quantity r) of the average value of the luminance values in the paving stone region. In FIG. 28, a change over time in the effect quantity r of the average value of the luminance values in the paving stone region based on images P obtained by imaging two types of iPS cells (TkDA and 1383D6) of different cell lines cultured in the culture medium is shown. As shown in FIG. 28, the time when the effect quantity r of the average value of the luminance values in the paving stone region becomes relatively greater than in other time periods is about 138 to 144 hours from the start of a cell culture process in the case of the iPS cells of the TkDA cell line and the time when the effect quantity r of the average value of the luminance values in the paving stone region becomes relatively greater than in other time periods is about 132 hours from the start of a cell culture process in the case of iPS cells of the 1383D6 cell line. Therefore, it is preferable that the image P used when the paving stone region-specific average luminance value calculation unit 162 for the luminance value of the paving stone region calculates the average value of the luminance values in the paving stone region be an image P captured during 138 to 144 hours from the start of the culture process in the case of the iPS cells of the TkDA cell line and it is preferable that the image P used when the paving stone region-specific average luminance value calculation unit 162 for the luminance values in the paving stone region calculates the average value of the luminance values in the paving stone region be an image P captured after 132 hours from the start of the culture process in the case of the iPS cells of the 1383D6 cell line. Also, the paving stone region-specific average luminance value calculation unit 162 may obtain the average value of the luminance values in the paving stone region in the image P of the cells of any one of cell lines including the TkDA cell line and the 1383D6 cell line captured at at least one point in time after about 132 hours or 138 to 144 hours from the start of the cell culture process. Also, the time such as 132 hours or 138 to 144 hours is an example and the present invention is not limited thereto. Any time period is preferred as long as it is a time period when the effect quantity r of the average value of the luminance values in the paving stone region in the image P used when the average value of the luminance values in the paving stone region is 0.5 or more. Here, it is generally considered that the reliability of a target index for which the effect quantity r is 0.5 or more is high. Thus, it is preferable to use the image P of the time period when the effect quantity r is 0.5 or more. For example, it is also preferable that the time period be a time period when the effect quantity r of the average value of the luminance values in the paving stone region in the image P of the cells of at least one of the TkDA cell line and the 1383D6 cell line is 0.5 or more. Also, the cells are not limited to the TkDA cell line or the 1383D6 cell line and cells of other cell lines may be determined by the determination unit 220. For example, the paving stone region-specific average luminance value calculation unit 162 may calculate an average value of the luminance values in the paving stone region from images of cells of other cell lines captured in a time period when the effect quantity r of the average value of the luminance values in the paving stone region in the image P of the cells of at least one of the TkDA cell line and the 1383D6 cell line is 0.5 or more. Also, the time period when effect quantities r of the average values of the luminance values in the paving stone regions in the images P of cells of both the TkDA cell line and the 1383D6 cell line are 0.5 or more is, for example, a time period after 57 hours from the start of the culture process for the iPS cells as an example. Alternatively, it may be a time period after 57 hours from the start of differentiation. Also, the determination unit 220 may not make the determination for the luminance values in the paving stone region in the image P captured in the time period when the effect quantity r is 0.5 or more on the basis of the effect quantity r or may make the determination on the basis of effect quantities r of other values.

Figure 29:
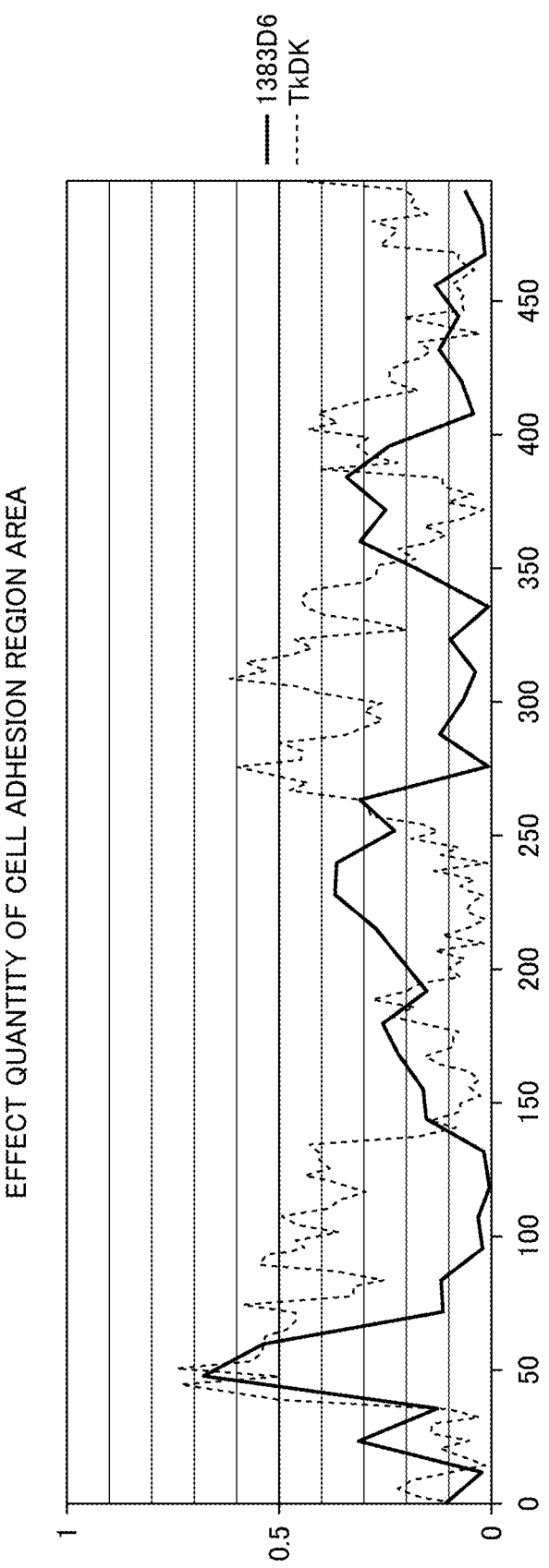
FIG. 29 is a diagram showing an example of an effect quantity of an area of the cell adhesion region.

FIG. 29 is a diagram showing an example of the effect quantity of the area of the cell adhesion region. In FIG. 29, a change over time in the effect quantity r of the area of the cell adhesion region based on an image P obtained by imaging two types of iPS cells (TkDA and 1383D6) of different cell lines cultured in the culture medium is shown. As shown in FIG. 29, the time when the effect quantity r of the area of the cell adhesion region becomes relatively greater than in other time periods is about 51 hours from the start of a cell culture process in the case of the iPS cells of the TkDA cell line and the time when the effect quantity r of the area of the cell adhesion region becomes relatively greater than in other time periods is about 48 hours from the start of a cell culture process in the case of iPS cells of the 1383D6 cell line. It is preferable that the image P used when the cell adhesion region extraction unit 180 extracts the cell adhesion region be an image P captured during 48 hours from the start of the culture process in the case of the iPS cells of the TkDA cell line and it is preferable that the image P used when the cell adhesion region extraction unit 180 extracts the cell adhesion region be an image P captured after 51 hours from the start of the culture process in the case of the iPS cells of the 1383D6 cell line. Also, the cell adhesion region area calculation unit 182 may obtain the area of the cell adhesion region in the image P of the cells of any one of cell lines including the TkDA cell line and the 1383D6 cell line captured at at least one point in time after about 51 hours and 48 hours from the start of the cell culture process. Also, the time such as 51 hours or 48 hours is an example and the present invention is not limited thereto. The image P used when the area of the cell adhesion region is calculated by the cell adhesion region area calculation unit 182 may be preferably an image captured in any time period as long as it is a time period when the effect quantity r of the area of the cell adhesion region is 0.5 or more. For example, it is also preferable that the time period be a time period when the effect quantity r of the area of the cell adhesion region in the image P of the cells of at least one of the TkDA cell line and the 1383D6 cell line is 0.5 or more. Also, the cell is not limited to the TkDA cell line or the 1383D6 cell line and cells of other cell lines may be determined by the determination unit 220. For example, the cell adhesion region area calculation unit 182 may calculate the area of the cell adhesion region from images of cells of other cell lines captured in a time period when the effect quantity r of the area of the cell adhesion region in the image P of the cells of at least one of the TkDA cell line and the 1383D6 cell line is 0.5 or more. Also, the time period when effect quantities r of the area of the cell adhesion region in the images P of cells of both the TkDA cell line and the 1383D6 cell line are 0.5 or more is, for example, a time period after 51 to 60 hours from the start of the culture process as an example. Also, the determination unit 220 may not make the determination for the area of the cell adhesion region in the image P captured in the time period when the effect quantity r is 0.5 or more on the basis of the effect quantity r or may make the determination on the basis of effect quantities r of other values.

Figure 30:
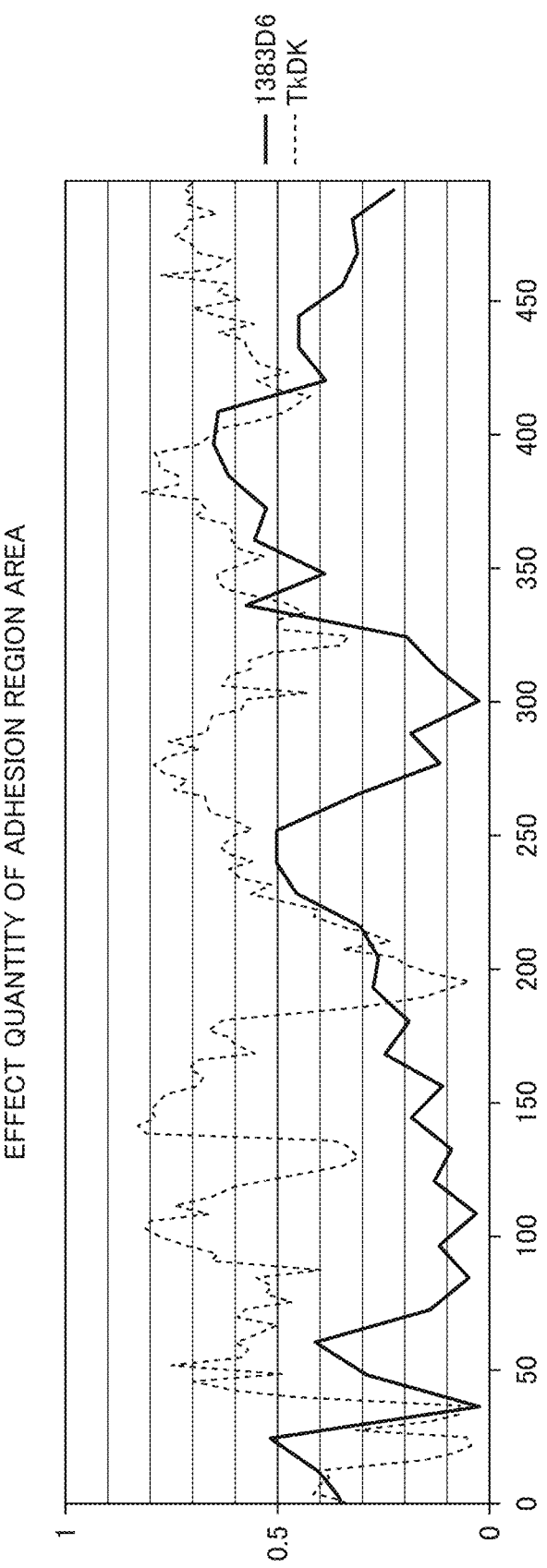
FIG. 30 is a diagram showing an example of an effect quantity of an area of the adhesion region.

FIG. 30 is a diagram showing an example of the effect quantity of the area of the adhesion region. In FIG. 30, a change over time in the effect quantity r of the area of the adhesion region based on an image P obtained by imaging two types of iPS cells (TkDA and 1383D6) cultured in the culture medium is shown. As shown in FIG. 30, the time when the effect quantity r of the area of the adhesion region becomes relatively greater than in other time periods is after about 141 hours from the start of a cell culture process in the case of the iPS cells of the TkDA cell line and the time when the effect quantity r of the area of the adhesion region becomes relatively greater than in other time periods is after about 3% hours from the start of a cell culture process in the case of iPS cells of the 1383D6 cell line. Therefore, it is preferable that the image P used when the adhesion region extraction unit 170 extracts the adhesion region be an image P captured after 141 hours from the start of the culture process in the case of the iPS cells of the TkDA cell line and it is preferable that the image P used when the adhesion region extraction unit 170 extracts the adhesion region be an image P captured after 3% hours from the start of the culture process in the case of the iPS cells of the 1383D6 cell line. Also, the adhesion region area calculation unit 172 may obtain the area of the adhesion region in the image P of the cells of any one of cell lines including the TkDA cell line and the 1383D6 cell line captured at at least one point in time after about 141 hours and 396 hours from the start of the cell culture process. Also, the time such as 141 hours or 396 hours is an example and the present invention is not limited thereto. The image P used when the area of the adhesion region is calculated by the adhesion region area calculation unit 172 may be preferably an image captured in any time period as long as it is a time period when the effect quantity r of the area of the adhesion region is 0.5 or more. For example, it is also preferable that the time period be a time period when the effect quantity r of the area of the adhesion region in the image P of the cells of at least one of the TkDA cell line and the 1383D6 cell line is 0.5 or more. Also, the cell is not limited to the TkDA cell line or the 1383D6 cell line and cells of other cell lines may be determined by the determination unit 220. For example, the adhesion region area calculation unit 172 may calculate the area of the adhesion region from images of cells of other cell lines captured in a time period when the effect quantity r of the area of the adhesion region in the image P of the cells of at least one of the TkDA cell line and the 1383D6 cell line is 0.5 or more. Also, the time period when effect quantities r of the area of the adhesion region in the images P of cells of both the TkDA cell line and the 1383D6 cell line are 0.5 or more is, for example, a time period after 240 hours or 360 to 405 hours from the start of the culture process as an example. Also, the determination unit 220 may not make the determination for the area of the adhesion region in the image P captured in the time period when the effect quantity r is 0.5 or more on the basis of the effect quantity r or may make the determination on the basis of effect quantities r of other values.

Figure 31:
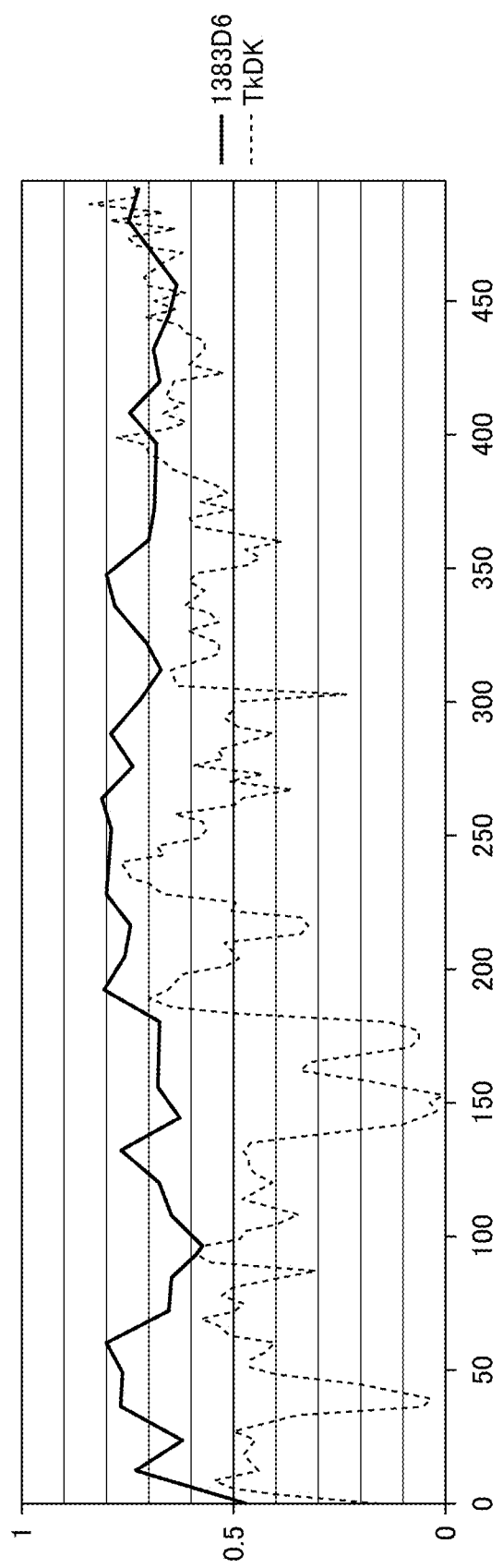
FIG. 31 is a diagram showing an example of an effect quantity of an area of the dead cell region.

FIG. 31 is a diagram showing an example of the effect quantity of the area of the dead cell region. In FIG. 31, a change over time in the effect quantity r of the area of the dead cell region based on an image P obtained by imaging two types of iPS cells (TkDA and 1383D6) cultured in the culture medium is shown. As shown in FIG. 31, the time when the effect quantity r of the area of the dead cell region becomes relatively greater than in other time periods is after about 486 hours from the start of a cell culture process in the case of the iPS cells of the TkDA cell line and the time when the effect quantity r of the area of the dead cell region becomes relatively greater than in other time periods is after about 264 hours from the start of a cell culture process in the case of iPS cells of the 1383D6 cell line. Therefore, it is preferable that the image P used when the dead cell region extraction unit 200 extracts the dead cell region be an image P captured after 486 hours from the start of the culture process in the case of the iPS cells of the TkDA cell line and it is preferable that the image P used when the dead cell region extraction unit 200 extracts the dead cell region be an image P captured after 264 hours from the start of the culture process in the case of the iPS cells of the 1383D6 cell line. Also, the dead cell region area calculation unit 202 may obtain the area of the dead cell region in the image P of the cells of any one of cell lines including the TkDA cell line and the 1383D6 cell line captured at at least one point in time after about 486 hours and 264 hours from the start of the cell culture process. Also, the time such as 486 hours or 264 hours is an example and the present invention is not limited thereto. The image P used when the area of the dead cell region is calculated by the dead cell region area calculation unit 202 may be preferably an image captured in any time period as long as it is a time period when the effect quantity r of the area of the dead cell region is 0.5 or more. For example, it is also preferable that the time period be a time period when the effect quantity r of the area of the dead cell region in the image P of the cells of at least one of the TkDA cell line and the 1383D6 cell line is 0.5 or more. Also, the cell is not limited to the TkDA cell line or the 1383D6 cell line and cells of other cell lines may be determined by the determination unit 220. For example, the dead cell region area calculation unit 202 may calculate the area of the dead cell region from images of cells of other cell lines captured in a time period when the effect quantity r of the area of the dead cell region in the image P of the cells of at least one of the TkDA cell line and the 1383D6 cell line is 0.5 or more. Also, the time period when effect quantities r of the area of the dead cell region in the images P of cells of both the TkDA cell line and the 1383D6 cell line are 0.5 or more is, for example, a time period of 6 to 9 hours, 63 to 69 hours, 78 to 81 hours, 90 to 96 hours, 186 to 201 hours, 207 to 210 hours, 222 hours, 228 to 261 hours, 270 hours, 276 to 282 hours, 294 hours, 300 hours, 306 to 348 hours, 366 to 369 hours, 375 to 492 hours, or the like from the start of the culture process as an example. Also, the determination unit 220 may not make the determination for the area of the dead cell region in the image P captured in the time period when the effect quantity r is 0.5 or more on the basis of the effect quantity r or may make the determination on the basis of effect quantities r of other values.

Figure 32:
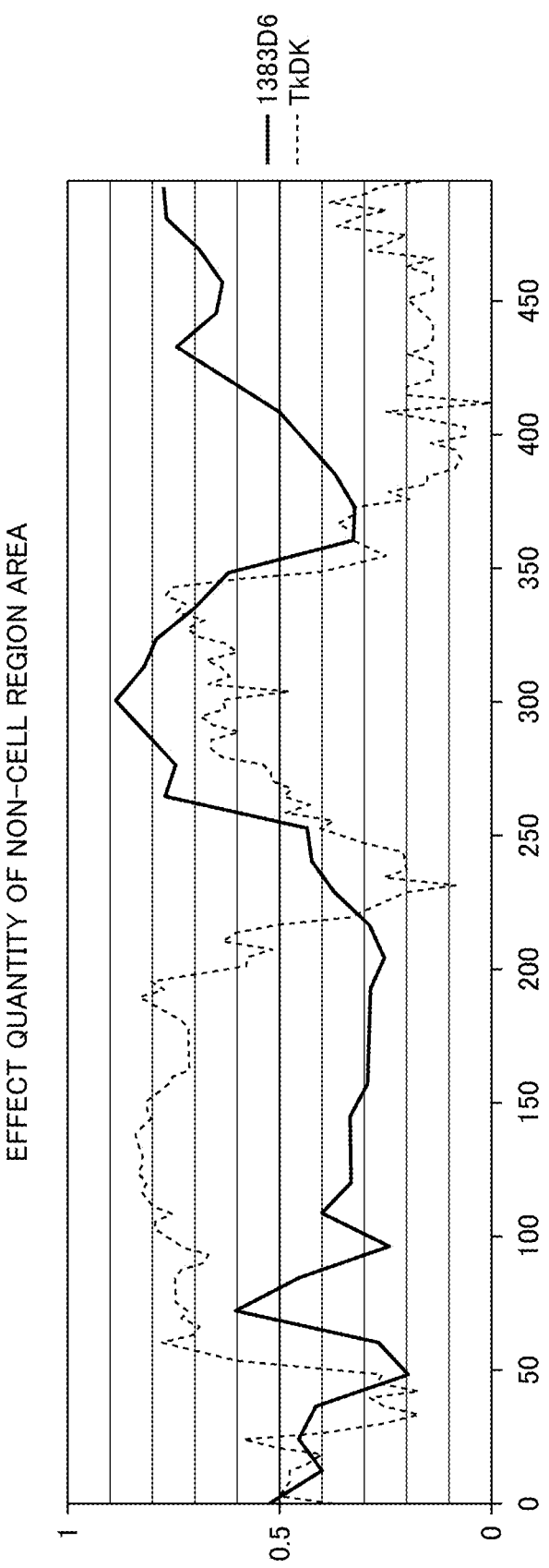
FIG. 32 is a diagram showing an example of an effect quantity of an area of the non-cell region.

FIG. 32 is a diagram showing an example of the effect quantity of the area of the non-cell region. In FIG. 32, a change over time in the effect quantity r of the area of the non-cell region based on an image P obtained by imaging two types of iPS cells (TkDA and 1383D6) cultured in the culture medium is shown. As shown in FIG. 32, the time when the effect quantity r of the area of the non-cell region becomes relatively greater than in other time periods is after about 138 hours from the start of a cell culture process in the case of the iPS cells of the TkDA cell line and the time when the effect quantity r of the area of the non-cell region becomes relatively greater than in other time periods is after about 300 hours from the start of a cell culture process in the case of iPS cells of the 1383D6 cell line. Therefore, it is preferable that the image P used when the non-cell region extraction unit 190 extracts the non-cell region be an image P captured after 138 hours from the start of the culture process in the case of the iPS cells of the TkDA cell line and it is preferable that the image P used when the non-cell region extraction unit 190 extracts the non-cell region be an image P captured after 300 hours from the start of the culture process in the case of the iPS cells of the 1383D6 cell line. Also, the non-cell region area calculation unit 192 may obtain the area of the non-cell region in the image P of the cells of any one of cell lines including the TkDA cell line and the 1383D6 cell line captured at at least one point in time after about 138 hours and 300 hours from the start of the cell culture process. Also, the time such as 138 hours or 300 hours is an example and the present invention is not limited thereto. The image P used when the area of the non-cell region is calculated by the non-cell region area calculation unit 192 may be preferably an image captured in any time period as long as it is a time period when the effect quantity r of the area of the non-cell region is 0.5 or more. For example, it is also preferable that the time period be a time period when the effect quantity r of the area of the non-cell region in the image P of the cells of at least one of the TkDA cell line and the 1383D6 cell line is 0.5 or more. Also, the cell is not limited to the TkDA cell line or the 1383D6 cell line and cells of other cell lines may be determined by the determination unit 220. For example, the non-cell region area calculation unit 192 may calculate the area of the non-cell region from images of cells of other cell lines captured in a time period when the effect quantity r of the area of the non-cell region in the image P of the cells of at least one of the TkDA cell line and the 1383D6 cell line is 0.5 or more. Also, the time period when effect quantities r of the area of the non-cell region in the images P of cells of both the TkDA cell line and the 1383D6 cell line are 0.5 or more is, for example, a time period of 72 hours, 270 to 300 hours, 306 to 345 hours, or the like from the start of the culture process as an example. Also, the determination unit 220 may not make the determination for the area of the non-cell region in the image P captured in the time period when the effect quantity r is 0.5 or more on the basis of the effect quantity r or may make the determination on the basis of effect quantities r of other values.

Figure 33:
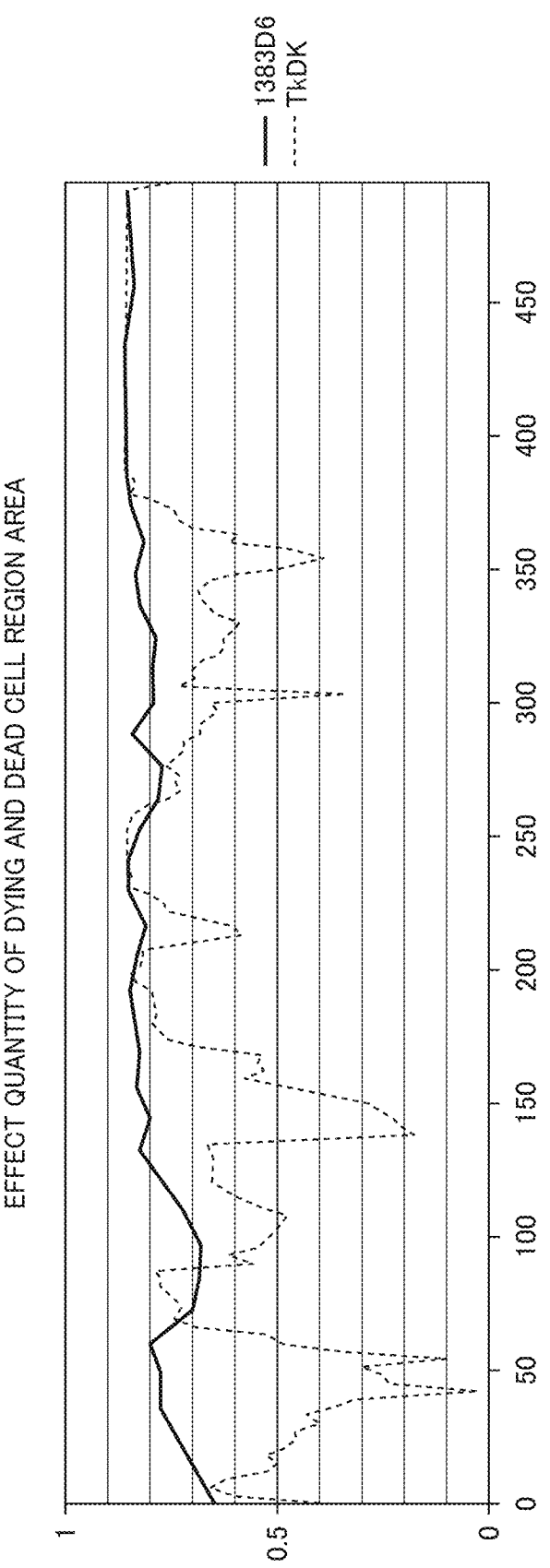
FIG. 33 is a diagram showing an example of an effect quantity of an area of the dying and dead cell region.

FIG. 33 is a diagram showing an example of the effect quantity of the area of the dying and dead cell region. In FIG. 33, a change over time in the effect quantity r of the area of the dying and dead cell region based on an image P obtained by imaging two types of iPS cells (TkDA and 1383D6) cultured in the culture medium is shown. As shown in FIG. 33, the time when the effect quantity r of the area of the dying and dead cell region becomes greatest is after about 387 hours from the start of a cell culture process in the case of the iPS cells of the TkDA cell line and the time when the effect quantity r of the area of the dying and dead cell region becomes greatest is after about 408 hours from the start of a cell culture process in the case of iPS cells of the 1383D6 cell line. Therefore, it is preferable that the image P used when the dying and dead cell region extraction unit 210 extracts the dying and dead cell region be an image P captured after 387 hours from the start of the culture process in the case of the iPS cells of the TkDA cell line and it is preferable that the image P used when the dying and dead cell region extraction unit 210 extracts the dying and dead cell region be an image P captured after 408 hours from the start of the culture process in the case of the iPS cells of the 1383D6 cell line. Also, the dying and dead cell region area calculation unit 212 may obtain the area of the dying and dead cell region in the image P of the cells of any one of cell lines including the TkDA cell line and the 1383D6 cell line captured at at least one point in time after about 387 hours and 408 hours from the start of the cell culture process. Also, the time such as 387 hours or 408 hours is an example and the present invention is not limited thereto. The image P used when the area of the dying and dead cell region is calculated by the dying and dead cell region area calculation unit 212 may be preferably an image captured in any time period as long as it is a time period when the effect quantity r of the area of the dying and dead cell region is 0.5 or more. For example, it is also preferable that the time period be a time period when the effect quantity r of the area of the dying and dead cell region in the image P of the cells of at least one of the TkDA cell line and the 1383D6 cell line is 0.5 or more. Also, the cell is not limited to the TkDA cell line or the 1383D6 cell line and cells of other cell lines may be determined by the determination unit 220. For example, the dying and dead cell region area calculation unit 212 may calculate the area of the dying and dead cell region from images of cells of other cell lines captured in a time period when the effect quantity r of the area of the dying and dead cell region in the image P of the cells of at least one of the TkDA cell line and the 1383D6 cell line is 0.5 or more. Also, the time period when effect quantities r of the area of the dying and dead cell region in the images P of cells of both the TkDA cell line and the 1383D6 cell line are 0.5 or more is, for example, a time period of 3 to 18 hours, 63 to 102 hours, 111 to 135 hours, 159 to 300 hours, 306 to 348 hours, 360 to 492 hours, or the like from the start of the culture process as an example. Also, the determination unit 220 may not make the determination for the area of the dying and dead cell region in the image P captured in the time period when the effect quantity r is 0.5 or more on the basis of the effect quantity r or may make the determination on the basis of effect quantities r of other values.

Although the case where the effect quantity r is used as a method of identifying a suitable time used for the determination process of the determination unit 220 has been described above, the present invention is not limited thereto. For example, the control unit 101 may derive a receiver operating characteristic (ROC) curve on the basis of the number of successful groups n1 and the number of unsuccessful groups n2 in the image P related to a certain region among the images P stored in the storage unit 301 and identify a time of the image P when an area under the curve (AUC), which is a value representing the accuracy of separation of the successful group and the unsuccessful group, is close to "1" (i.e., the separation accuracy between the successful group and the unsuccessful group is high). In this case, the determination unit 220 performs a determination process for each region on the basis of the image P at a time when the AUC is high.

<Regarding Operation of Image Determination Device 10>

Figure 34:
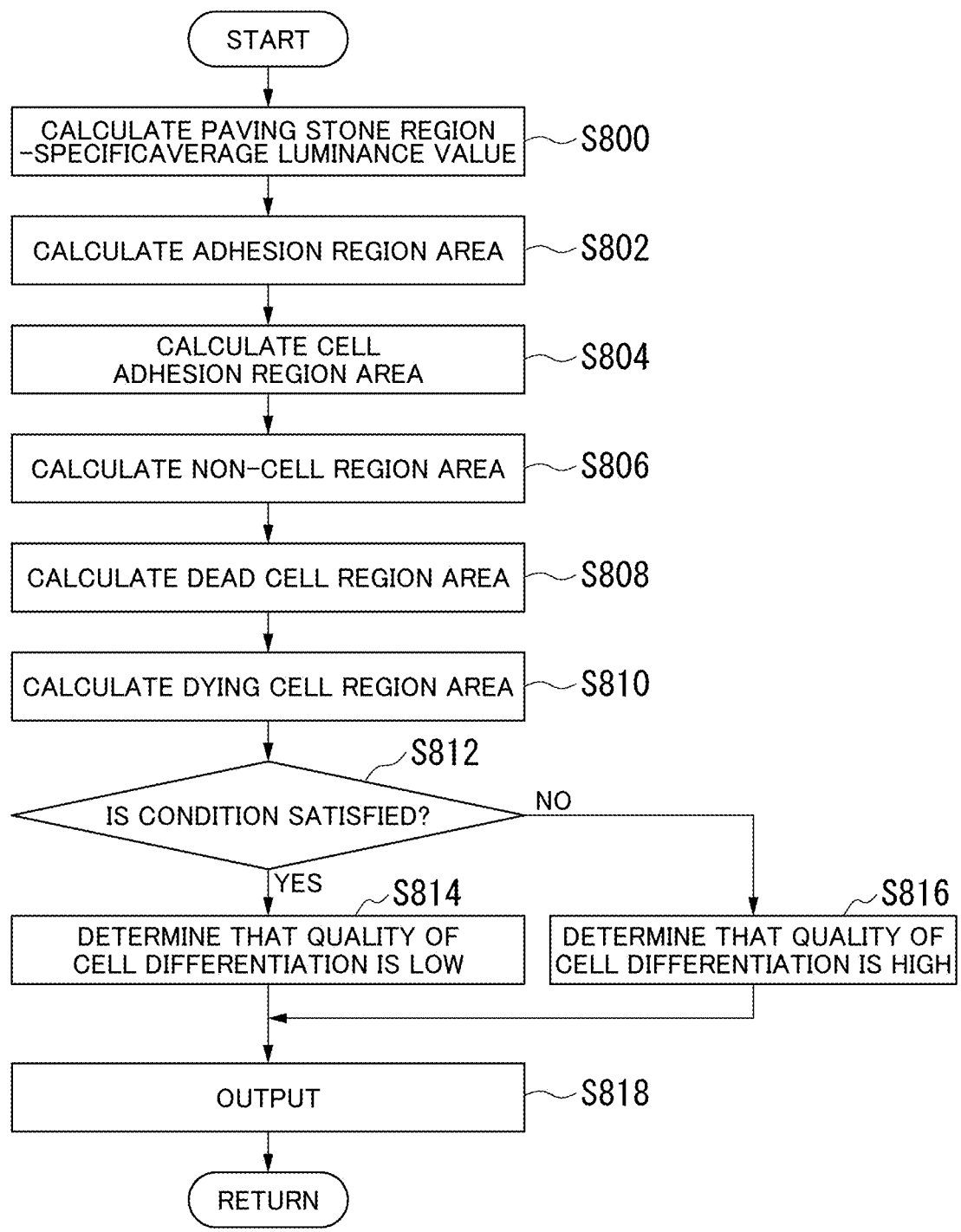
FIG. 34 is a diagram showing an example of an operation of the image determination device of the third embodiment.

FIG. 34 is a diagram showing an example of the operation of the image determination device 10 of the third embodiment. The paving stone region-specific average luminance value calculation unit 162 of the image determination device 10 calculates an average value of the luminance values in the paving stone region extracted by the paving stone region extraction unit 160 (step S800). Subsequently, the adhesion region area calculation unit 172 calculates an area of the adhesion region extracted by the adhesion region extraction unit 170 (step S802). Subsequently, the cell adhesion region area calculation unit 182 calculates an area of the cell adhesion region extracted by the cell adhesion region extraction unit 180 (step S804). Subsequently, the non-cell region area calculation unit 192 calculates an area of the non-cell region extracted by the non-cell region extraction unit 190 (step S806). Subsequently, the dead cell region area calculation unit 202 calculates an area of the dead cell region extracted by the dead cell region extraction unit 200 (step S808). Subsequently, the dying and dead cell region area calculation unit 212 calculates an area of the non-cell region extracted by the dying and dead cell region extraction unit 210 (step S810).

The determination unit 220 determines the quality of cell differentiation on the basis of information calculated by each functional unit (step S812). For example, the determination unit 220 determines that the quality of cell differentiation is low when any one of a condition (1) that the average value of the luminance values in the paving stone region calculated by the paving stone region-specific average luminance value calculation unit 162 is less than the threshold value for the average value of the luminance values in the paving stone region indicated by the paving stone region-specific average luminance threshold value 301a, a condition (2) that the value of the area of the adhesion region calculated by the adhesion region area calculation unit 172 is less than the threshold value for the area of the adhesion region indicated by the adhesion region area-specific threshold value 301b, a condition (3) that the value of the area of the cell adhesion region calculated by the cell adhesion region area calculation unit 182 is less than the threshold value for the area of the cell adhesion region indicated by the cell adhesion region area-specific threshold value 301c, a condition (4) that the value of the area of the non-cell region calculated by the non-cell region area calculation unit 192 is greater than or equal to the threshold value for the area of the non-cell region indicated by the non-cell region area-specific threshold value 301d, a condition (5) that the value of the area of the dead cell region calculated by the dead cell region area calculation unit 202 is greater than or equal to the threshold value for the area of the dead cell region indicated by the dead cell region area-specific threshold value 301e, and a condition (6) that the value of the area the dying and dead cell region calculated by the dying and dead cell region area calculation unit 212 is greater than or equal to the threshold value for the area of the dying and dead cell region indicated by the dying and dead cell region area-specific threshold value 301f is satisfied (step S814) and determines that the quality of cell differentiation is high when any condition is not satisfied (step S816).

A case where the quality of cell differentiation is high is, for example, a case where a ratio of the number of normal mature hepatocytes to the final number of cells is higher than or equal to a standard ratio (for example, 80%), a case where the bias of the shape of mature hepatocytes is less than a standard or the like, and a case where the quality of cell differentiation is low is, for example, a case where the ratio is less than the standard ratio, a case where the bias of the shape of mature hepatocytes is greater than or equal to the standard, or the like.

Also, the determination unit 220 may determine the quality of cell differentiation on the basis of the index value for determining the quality of differentiation in the time-lapse image before the cells form the paving stone region and the luminance value of the paving stone region in the time-lapse image after the cells form the paving stone region. Here, the index value for determining the quality of differentiation in the time-lapse image before the cells form the paving stone region is, for example, a value calculated for the above-described evaluation index before the paving stone region is formed. Values calculated for the evaluation index described above before the paving stone region is formed include, for example, the area of the adhesion region, the area of the cell adhesion region, the area of the non-cell region, the area of the dead cell region, and the area of the dying and dead cell region.

The determination unit 220 determines the quality of cell differentiation on the basis of, for example, a first condition, which is a condition indicating a magnitude relationship between an index value for determining the quality of differentiation in a time-lapse image before cells form a paving stone region and a threshold value for this index value, and a second condition, which is a condition indicating a magnitude relationship between the luminance value of the paving stone region in the time-lapse image after cells form the paving stone region and the paving stone region-specific average luminance threshold value 301*a*.

The determination unit 220 determines that the quality of cell differentiation is low, for example, when both the first condition and the second condition are satisfied. In this case, the determination unit 220 determines that the quality of cell differentiation is high when at least one of the first condition and the second condition is not satisfied. Also, the determination unit 220 may determine that the quality of cell differentiation is low, for example, when at least one of the first condition and the second condition is satisfied. In this case, the determination unit 220 determines that the quality of cell differentiation is high when both the first condition and the second condition are not satisfied. Also, the above-described condition is an example and the determination unit 220 may reverse signs of the index value and the threshold value for the index value to determine the quality of cell differentiation. In this case, the determination unit 220 determines that the quality of cell differentiation is low when both the first condition and the second condition are not satisfied.

Here, the first condition is, for example, a condition (referred to as a condition (2a)) that the value of the area of the adhesion region calculated by the adhesion region area calculation unit 172 under the above-described condition (2) is set as a value calculated before cells form the paving stone region. Also, as another example, the first condition is referred to as a condition (a condition (3a)) that the value of the area of the cell adhesion region calculated by the cell adhesion region area calculation unit 182 under the above-described condition (3) is set as a value calculated before the cells form the paving stone region. As another example, the first condition is a condition (referred to as a condition (4a)) that the value of the area of the non-cell region calculated by the non-cell region area calculation unit 192 under the above-described condition (4) is set as a value calculated before the cells form the paving stone region. Also, as another example, the first condition is a condition (referred to as a condition (5a)) that the value of the area of the dead cell region calculated by the dead cell region area calculation unit 202 under the above-described condition (5) is set as a value calculated before the cells form the paving stone region. Also, as another example, the first condition is a condition (referred to as a condition (6a)) that the value of the area of the dying and dead cell region calculated by the dying and dead cell region area calculation unit 212 under the above-described condition (6) is a value calculated before the cells form the paving stone region.

The second condition is, for example, a condition (referred to as condition (1a)) that the average value of the luminance values in the paving stone region calculated by the paving stone region-specific average luminance value calculation unit 162 under the above-described condition (1) is set as a value calculated after cells form the paving stone region.

Also, the determination unit 220 may determine the quality of cell differentiation on the basis of a third condition that is a condition based on the index value for determining the quality of differentiation in the time-lapse image before the cells form the paving stone region and the luminance value of the paving stone region in the time-lapse image after the cells form the paving stone region. For example, the third condition is a condition indicating a magnitude relationship between a prescribed value and an average, a difference, a weighted average, a product, or a ratio between an index value for determining the quality of differentiation in the time-lapse image before cells form the paving stone region and a luminance value of the paving stone region in the time-lapse image after cells form the paving stone region. When the dimension of the index value for determining the quality of differentiation in the time-lapse image before cells form the paving stone region is different from the dimension of the luminance value of the paving stone region in the time-lapse image after the cells form the paving stone region, the average, the difference, or the weighted average is calculated by multiplying a factor for aligning both dimensions when the average, the difference, or the weighted average is calculated.

The third condition is, for example, that an average value between the value of the area of the adhesion region calculated by the adhesion region area calculation unit 172 on the basis of the time-lapse image before cells form the paving stone region and the average value of the luminance values in the paving stone region calculated by the paving stone region-specific average luminance value calculation unit 162 on the basis of the time-lapse image after cells form the paving stone region is smaller than a prescribed threshold value. Here, the value of the area of the adhesion region is multiplied by a prescribed factor so that the dimension matches the luminance value and the average associated with the average value of the luminance values in the paving stone region is calculated. Also, the determination unit 220 may reverse the signs of the index and the index value of the third condition to determine the quality of cell differentiation.

Among the above-described threshold values, the adhesion region area-specific threshold value 301*b*, the cell adhesion region area-specific threshold value 301*c*, the non-cell region area-specific threshold value 301*d*, the dead cell region area-specific threshold value 301*e*, and the dying and dead cell region area-specific threshold value 301*f* are examples of an index for determining the quality of differentiation before cells form the paving stone region. Also, among the above-described threshold values, the paving stone region-specific average luminance threshold value 301*a*, the adhesion region area-specific threshold value 301*b*, the cell adhesion region area-specific threshold value 301*c*, the non-cell region area-specific threshold value 301*d*, the dead cell region area-specific threshold value 301*e*, and the dying and dead cell region area-specific threshold value 301*f* are examples of an index for determining the quality of differentiation after cells form the paving stone region. The average value of the luminance values in the paving stone region, the area of the adhesion region, the area of the cell adhesion region, the area of the non-cell region, the area of the dead cell region, and the area of the dying and dead cell region are examples of indices calculated in correspondence with these threshold values.

Therefore, the determination unit 220 determines the quality of cell differentiation on the basis of an index value (the area of the adhesion region, the area of the cell adhesion region, the area of the non-cell region, the area of the dead cell region, and the area of the dying and dead cell regions) calculated in correspondence with an index (the adhesion region area-specific threshold value 301*b*, the cell adhesion region area-specific threshold value 301*c*, the non-cell region area-specific threshold value 301*d*, the dead cell region area-specific threshold value 301*e*, and the dying and dead cell region area-specific threshold value 301*f*) for determining the quality of differentiation before cells form the paving stone region and an index value (the average value of the luminance values in the paving stone region, the area of the adhesion region, the area of the cell adhesion region, the area of the non-cell region, the area of the dead cell region, and the area of the dying and dead cell region) calculated in correspondence with an index (the paving stone region-specific average luminance threshold value 301a, the adhesion region area-specific threshold value 301b, the cell adhesion region area-specific threshold value 301c, the non-cell region area-specific threshold value 301d, the dead cell region area-specific threshold value 301e, and the dying and dead cell region area-specific threshold value 301f) for determining the quality of differentiation after cells form the paving stone region.

Also, the determination unit 220 may be configured to determine that the quality of differentiation is low when a prescribed number (for example, two or more) of conditions among the conditions (1) to (6) and (1a) to (6a) are satisfied. Also, the determination unit 220 may be configured to determine that the quality of cell differentiation is high when the number of satisfied conditions among the conditions (1) to (6) and (1a) to (6a) is less than a prescribed number (for example, two). Also, the determination unit 220 may be configured to reverse the signs of the indices and index values of the conditions (1) to (6) and (1a) to (6a) to determine the quality of cell differentiation.

Also, the determination unit 220 may not determine the quality of cell differentiation under all the conditions (1) to (6) and (1a) to (6a). For example, the determination unit 220 may determine the quality of cell differentiation on the basis of a condition selected by the user via an input device (not shown) among the conditions (1) to (6) and (1a) to (6a). In this case, the user may select the condition for the determination unit 220 to determine the quality of cell differentiation from the conditions (1) to (6) and (1a) to (6a) on the basis of a value of the effect quantity r of each of the conditions (1) to (6) and (1a) to (6a) (for example, an average value or a maximum value of the effect quantity r at each time). Also, the user may not select a condition and the control unit 101 may select the condition for the determination unit 220 to determine the quality of cell differentiation from the conditions (1) to (6) and (1a) to (6a). In this case, the control unit 101 may select the condition for the determination unit 220 to determine the quality of cell differentiation from the conditions (1) to (6) and (1a) to (6a) on the basis of a value of the effect quantity r of each of the conditions (1) to (6) and (1a) to (6a) (for example, an average value, a maximum value, or the like of the effect quantity r at each time). Also, when the user or the control unit 101 selects the condition for the determination unit 220 to determine the quality of cell differentiation from the conditions (1) to (6) and (1a) to (6a), a region extraction unit corresponding to the selected condition among the region extraction units (the paving stone region extraction unit 160, the adhesion region extraction unit 170, the cell adhesion region extraction unit 180, the non-cell region extraction unit 190, the dead cell region extraction unit 200, and the dying and dead cell region extraction unit 210) may be configured to perform a region extraction process.

The output unit 230 outputs a determination result of a determination process of the determination unit 220 (step S900).

As described above, the image determination device 10 of the present embodiment can reduce the time and effort for determining a cell culture state by calculating an evaluation index (for example, a paving stone region luminance value, an adhesion region area, a cell adhesion region area, a non-cell region area, a photoreceptor cell region area, a dying and dead cell region area, and the like) according to a cell differentiation-inducing process and determining the quality of cell differentiation on the basis of the calculated evaluation index.

According to the above-described embodiment, a cell evaluation method for use in the image determination device 10 includes acquiring a first evaluation index (for example, the average value of the luminance values in the paving stone region, the area of the adhesion region, the area of the cell adhesion region, the area of the non-cell region, the area of the dead cell region, and the area of the dying and dead cell region) and a first index (for example, indices such as the paving stone region-specific average luminance threshold value 301a, the adhesion region area-specific threshold value 301b, the cell adhesion region area-specific threshold value 301c, the non-cell region area-specific threshold value 301d, the dead cell region area-specific threshold value 301e, and the dying and dead cell region area-specific threshold value 301f) calculated using the first evaluation index with respect to comparative target cells in a culture process including a cell differentiation-inducing process; calculating a second index (for example, the average value of the luminance values in the paving stone region, the area of the adhesion region, the area of the cell adhesion region, the area of the non-cell region, the area of the dead cell region, and the area of the dying and dead cell region) on the basis of the first evaluation index with respect to evaluation target cells different from the comparative target cells; and evaluating differentiation of the evaluation target cells by comparing the first index with the second index.

The first evaluation index is acquired from a plurality of images associated with elapsed time from a start of the culture process and a high- or low-quality differentiation result.

In the cell evaluation method for use in the image determination device 10, the culture process includes a plurality of processes and the first evaluation index according to the process is acquired.

Although a case where the paving stone region-specific average luminance threshold value 301a, the adhesion region area-specific threshold value 301b, the cell adhesion region area-specific threshold value 301c, the non-cell region area-specific threshold value 301d, the dead cell region area-specific threshold value 301e, and the dying and dead cell region area-specific threshold value 301f are values predetermined by comparing indices based on an image P in which cells determined to become normal mature hepatocytes are imaged when the cell observer observes cells with indices based on an image P in which cells determined not to become normal mature hepatocytes are imaged when the cell observer observes cells has been described above, the present invention is not limited thereto. These threshold values are, for example, values acquired using images P of cells captured by the imaging device 34 at specific times in addition to images P captured after differentiation into normal mature hepatocytes is achieved or after differentiation into normal mature hepatocytes is not achieved.

Although the image determination device 10 determines the quality of cell differentiation on the basis of six evaluation indices (specifically, at least one evaluation index of six evaluation indices) obtained from the time-lapse images acquired during a period (for example, 21 days) of the first to fourth differentiation-inducing processes in the above-described embodiment, the present invention is not limited thereto. For example, the present invention can also be applied to processes including an undifferentiated state maintaining culture process for iPS cells before the first to fourth differentiation-inducing processes (i.e., processes from the undifferentiated state maintaining culture process to the first to fourth differentiation-inducing processes). As described above, the undifferentiated state maintaining culture process for iPS cells is a culture process (for example, 5 days) for increasing the number of iPS cells while maintaining the iPS cells in an undifferentiated state. In this case, the image determination device 10 determines the quality of cell differentiation on the basis of the above-described indices obtained from the time-lapse images acquired during a period (for example, 26 days) from the undifferentiated state maintaining culture process to the first to fourth differentiation-inducing processes. Here, because a method of determining the quality of cell differentiation based on each index is similar to the method as described above, description thereof will be omitted. Also, the present invention can be applied to some processes as well as all processes from the undifferentiated state maintaining culture process to the first to fourth differentiation-inducing processes.

Although the case where the time-lapse image after the cells form the paving stone region is a time-lapse image in which cells are determined to have formed the paving stone region by the paving stone region determination unit (the paving stone region extraction unit 160) has been described as an example in the present embodiment, the present invention is not limited thereto. The time-lapse image after cells form the paving stone region may be a time-lapse image for which the observer has predetermined that the cells have formed the paving stone region. In this case, the acquisition unit 110 acquires time-lapse images including a time-lapse image in which it is predetermined that cells have formed the paving stone region as the time-lapse image. Therefore, the time-lapse image after cells form the paving stone region may be a time-lapse image for which it has been predetermined that cells included in the time-lapse image acquired by the acquisition unit 110 have formed the paving stone region. In this case, the paving stone region extraction unit 160 may not have a function as the paving stone region determination unit.

Also, the index value based on a result of determining the quality of differentiation in the time-lapse image before cells form the paving stone region may be calculated after a process of capturing the time-lapse image is completed. In this case, the determination unit 220 determines the quality of cell differentiation on the basis of the captured time-lapse image after a process of capturing the time-lapse image is completed. Also, the index value based on the result of determining the quality of differentiation in the time-lapse image before cells form the paving stone region may be calculated immediately in a period of time until cells form the paving stone region. In this case, the determination unit 220 may determine the quality of cell differentiation for the time-lapse image after cells form the paving stone region before the process of capturing the time-lapse image is completed on the basis of the index value that has been calculated immediately.

Modified Example 3

Hereinafter, Modified Example 3 of the third embodiment described above will be described with reference to FIGS. 35 to 40.

Also, the evaluation index used for determining the quality of cell differentiation is not limited to the above-described six evaluation indices, and other evaluation indices may be used. For example, in the undifferentiated state maintaining culture process for iPS cells, a distance between iPS cells changes in accordance with the proliferation of the number of iPS cells. That is, the adhesion between cells is weakened. Because the distance between the iPS cells changes, the luminance value near the boundary between the adjacent iPS cells changes in the image (the phase difference image) acquired by the imaging device 34. Here, the image determination device 10 may determine the quality of cell differentiation using an area of a region having a prescribed luminance value near a boundary between adjacent iPS cells as an evaluation index. The region having the prescribed luminance value near the boundary between the adjacent iPS cells has a muscle-shaped form and the region having the prescribed luminance value near the boundary between the adjacent iPS cells is referred to as a muscle region in the following description. Therefore, the image determination device 10 may determine the quality of cell differentiation using an area of the muscle region as an evaluation index.

<Regarding Region within Image>

Figure 35:
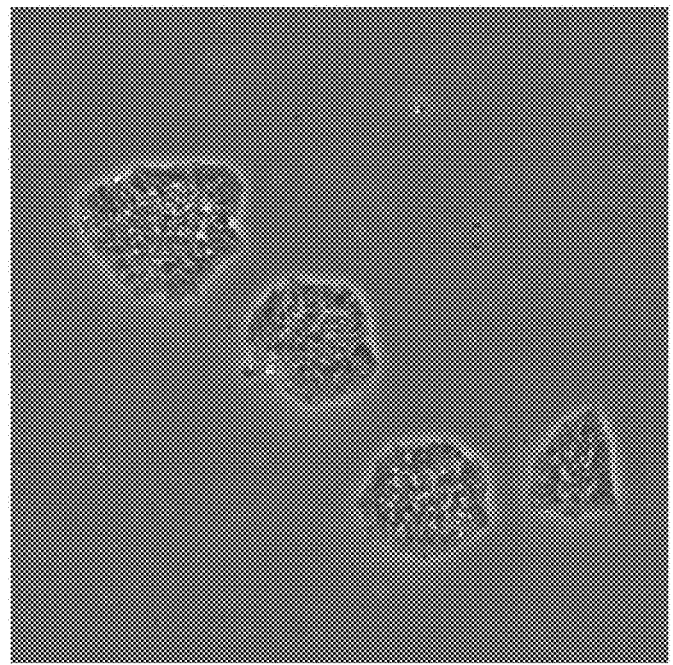
FIG. 35 is a diagram showing an example of an original image.
Figure 36:
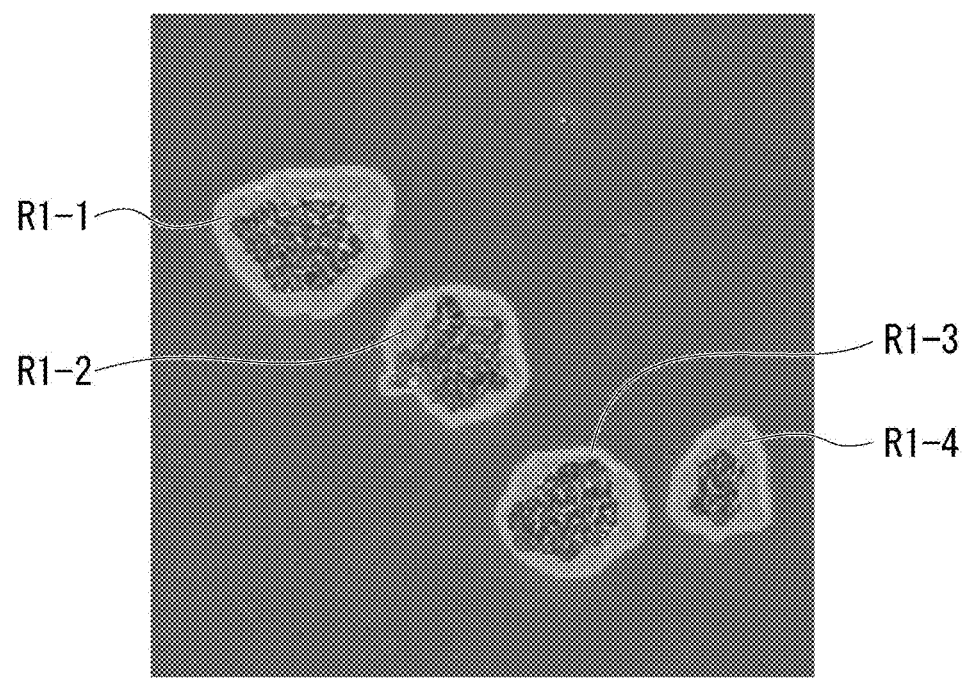
FIG. 36 is a diagram showing an example of a sparse mask.
Figure 37:
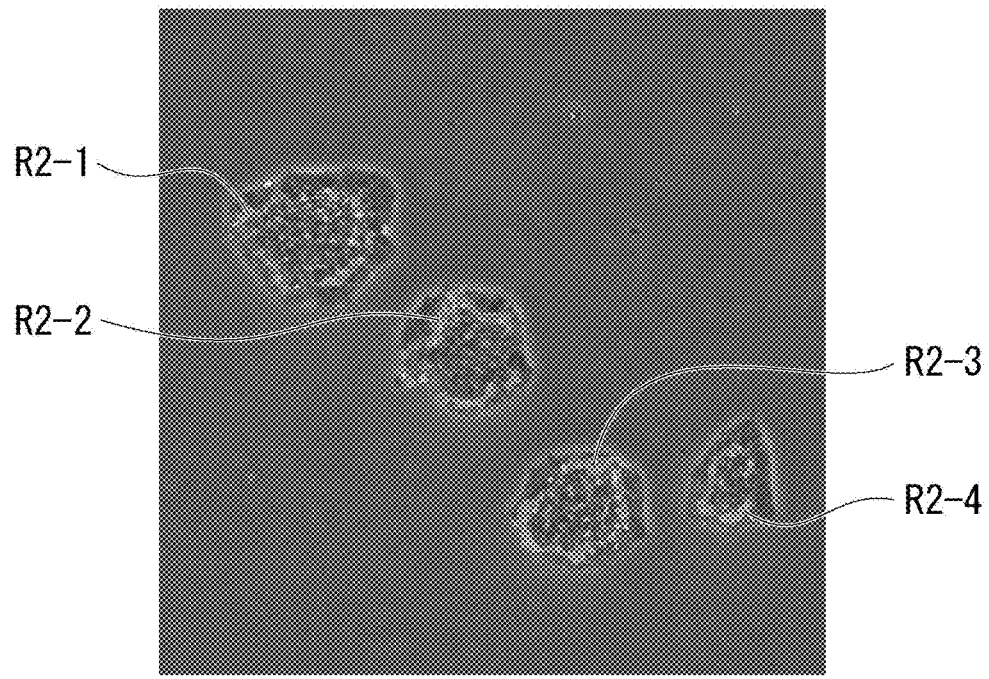
FIG. 37 is a diagram showing an example of a dense mask.
Figure 38:
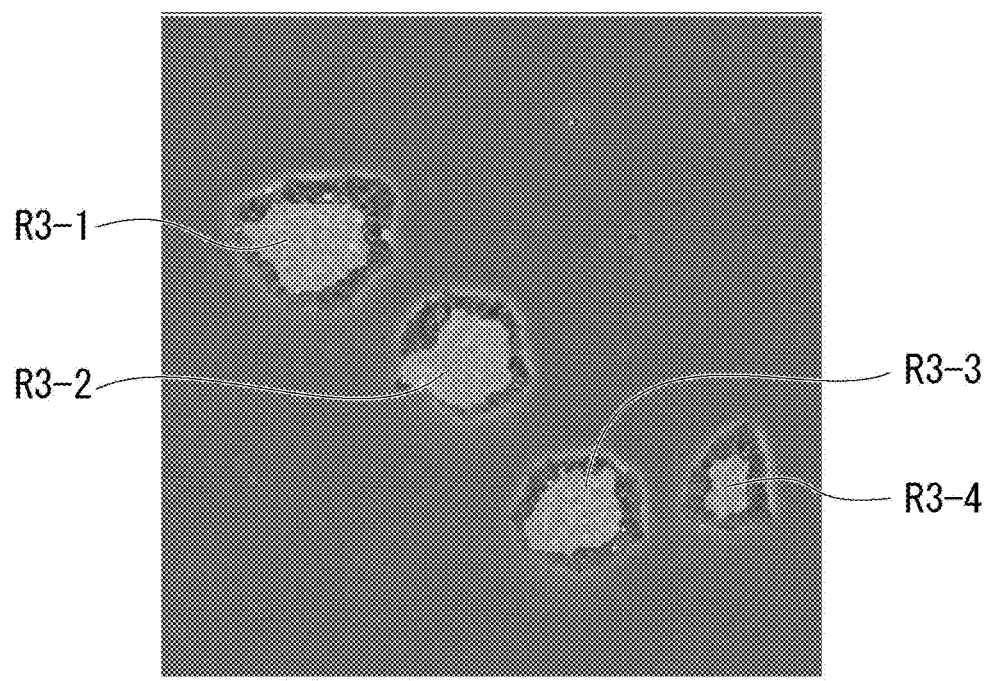
FIG. 38 is a diagram showing an example of a muscle mask.

Here, an original image which is an image before a region is extracted and a region within the original image will be described with reference to FIGS. 35 to 38. FIG. 35 is a diagram showing an example of the original image. Mask images corresponding to regions shown in FIGS. 36 to 38 are generated according to image processing to be described below from FIG. 35. The mask image is an image that masks a region other than a specific region of the original image.

FIG. 36 is a diagram showing an example of a sparse mask. The sparse mask is an image that masks a region other than a sparse region in the original image. The sparse region is a cell region having a low cell density around the colony. In FIG. 36, sparse regions R1-1 to R1-4 are shown as examples of the sparse region. In the sparse region, a boundary between the cytoplasm and the nucleus is clear.

FIG. 37 is a diagram showing an example of a dense mask according to the present embodiment. The dense mask is an image that masks a region other than a dense region in the original image. The dense region is a cell region having a high cell density around the colony. In FIG. 37, dense regions R2-1 to R2-4 are shown as examples of the dense region. In the dense region, a boundary between the cytoplasm and the nucleus is unclear.

FIG. 38 is a diagram showing an example of a muscle mask according to the present embodiment. The muscle mask is an image that masks a region other than the muscle region in the original image. As described above, the muscle region is a region having a prescribed luminance value near the cell boundary, in other words, a region formed by a gap between cells in the colony. In FIG. 38, muscle regions R3-1 to R3-4 are shown as examples of the muscle region.

<Regarding Image Processing on Image P>

Figure 39:
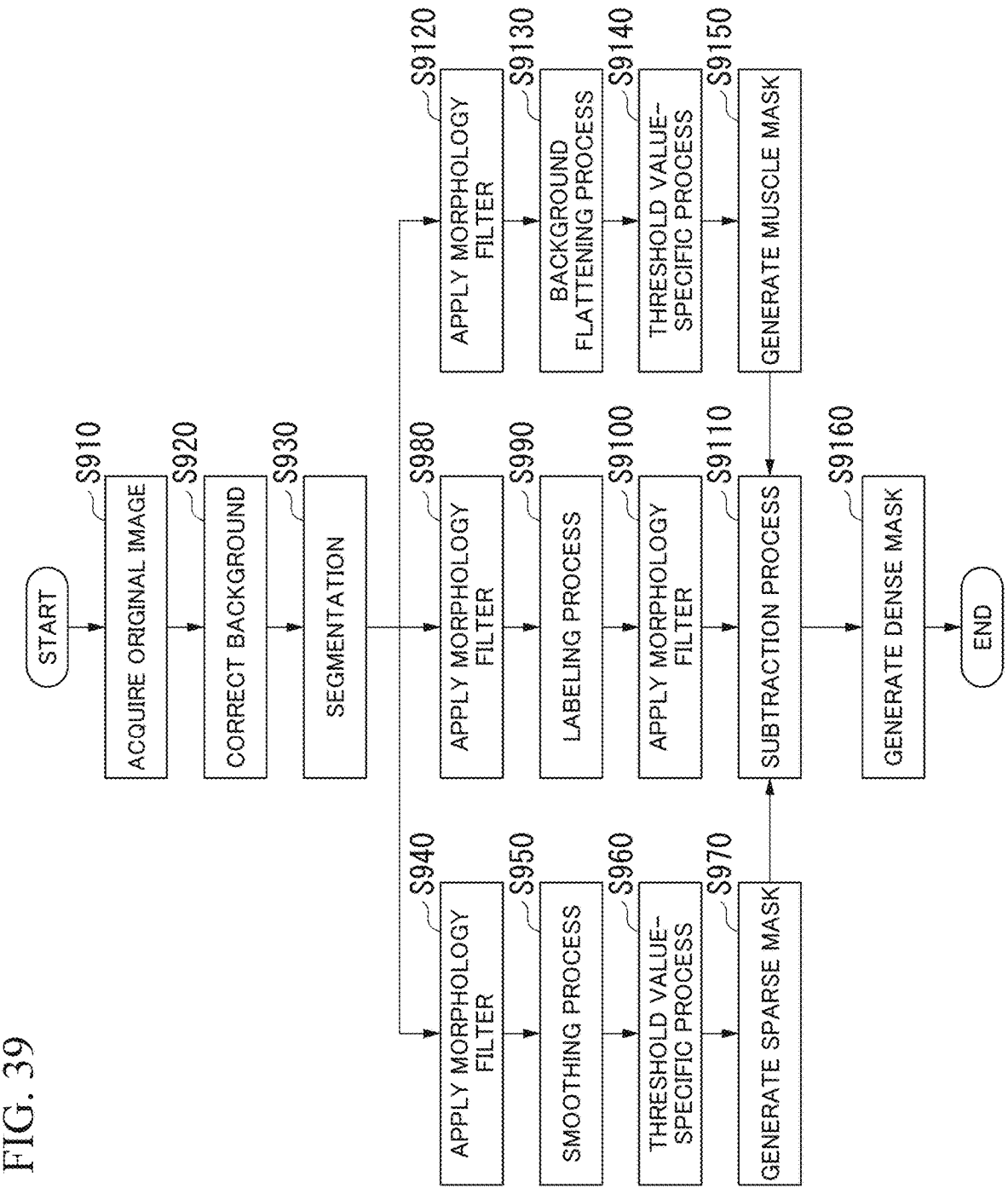
FIG. 39 is a diagram showing an example of an operation of an image determination device of a modified example of the third embodiment

FIG. 39 is a flowchart showing an example of an operation of the image determination device 10 of Modified Example 3. The acquisition unit 110 acquires an image P as an original image according to the processing of step S910. The processing of steps S920 to S9160 to be described below is executed by a muscle region extraction unit (not shown) in the control unit 101 of the image determination device 10.

The muscle region extraction unit (not shown) performs a process of correcting the background of the image P acquired by the acquisition unit 110 (step S920). The muscle region extraction unit (not shown) performs, for example, a process of flattening the background of the image P as a process of correcting the background. Subsequently, the muscle region extraction unit (not shown) performs a segmentation process for the image P whose background has been corrected (step S930). In the segmentation process, the muscle region extraction unit (not shown) determines a cell region in the image P and a region other than the cell and excludes the region other than the cell from the image P.

Hereinafter, the muscle region extraction unit (not shown) generates a sparse mask according to the processing of steps S940 to S970, generates a muscle mask according to the processing of steps S9120 to S9150, and generates a dense mask according to the processing of steps S980 to S9160. The muscle region extraction unit (not shown) executes the processing of steps S940 to S970, the processing of steps S9120 to S9150, and the processing of steps S980 to S9160 in parallel.

The muscle region extraction unit (not shown) applies a morphology filter to the image P processed in the processing of steps S920 and S930 (step S940) and performs a process of smoothing the entire image P (step S950). Subsequently, the muscle region extraction unit (not shown) performs a threshold value-specific process on the image P and extracts a region having a luminance value less than or equal to a luminance value of the sparse region (step S960). The muscle region extraction unit (not shown) extracts a sparse region from the image P by extracting a region having a luminance value less than or equal to the luminance value of the sparse region from the image P. The muscle region extraction unit (not shown) generates a sparse mask on the basis of the sparse region extracted according to the processing of step S960 (step S970).

The muscle region extraction unit (not shown) applies a morphology filter to the image P processed in the processing of steps S920 and S930 (step S9120). The muscle region extraction unit (not shown) clarifies the boundary of the muscle region by applying the morphology filter. The morphology filter is used to separate garbage and dying cells from a boundary between adjacent cells. The muscle region extraction unit (not shown) performs a process of flattening the background of the image P (step S9130) and performs a threshold value-specific process (step S9140). Here, the muscle region extraction unit (not shown) extracts a region having a luminance value greater than or equal to the threshold value TH4 and less than or equal to the threshold value TH5 as the muscle region in the threshold value-specific process in step S9140. The muscle region extraction unit (not shown) generates a muscle mask on the basis of the extracted muscle region (step S9150).

The muscle region extraction unit (not shown) applies a morphology filter to the image P on which the processing of steps S920 and S930 has been performed (step S980). Subsequently, the cell adhesion region extraction unit 180 performs a labeling process on a region clarified by the morphology filter (step S990). The muscle region extraction unit (not shown) applies the morphology filter to the image P in which the missing pixels have been filled according to the labeling process (step S9100).

The muscle region extraction unit (not shown) performs a subtraction process (step S9110). In the subtraction process, the muscle region extraction unit (not shown) excludes the sparse region corresponding to the sparse mask generated in step S970 and the muscle region corresponding to the muscle mask generated in step S9150 from the entire image P. The muscle region extraction unit (not shown) generates a dense mask on the basis of a result of excluding the sparse region and the muscle region from the cell region of the image P.

When the processing of steps S910 to S9160 ends, the muscle region area calculation unit (not shown) of the control unit 101 calculates an area of the muscle region extracted by the muscle region extraction unit (not shown) as an evaluation index and supplies the evaluation index to the determination unit 220. Also, because the other operations of the image determination device 10 are similar to those described above, description thereof will be omitted.

A series of processes of the threshold value-specific process, the smoothing process, the background flattening process, the labeling process, and the morphology filter process of the above-described muscle region extraction unit (not shown) are an example, and other existing image processing may be combined with the series of processes or may be replaced with a part of this series of processes. Also, the area of the cell boundary region may be calculated as an evaluation index not only in the undifferentiated state maintaining culture process for iPS cells but also in the other first to fourth differentiation-inducing processes. In this case, it is possible to suitably determine the quality of differentiation into hepatic endoderm cells particularly.

<Relationship Between Muscle Region and Amount of Albumin>

Figure 40:
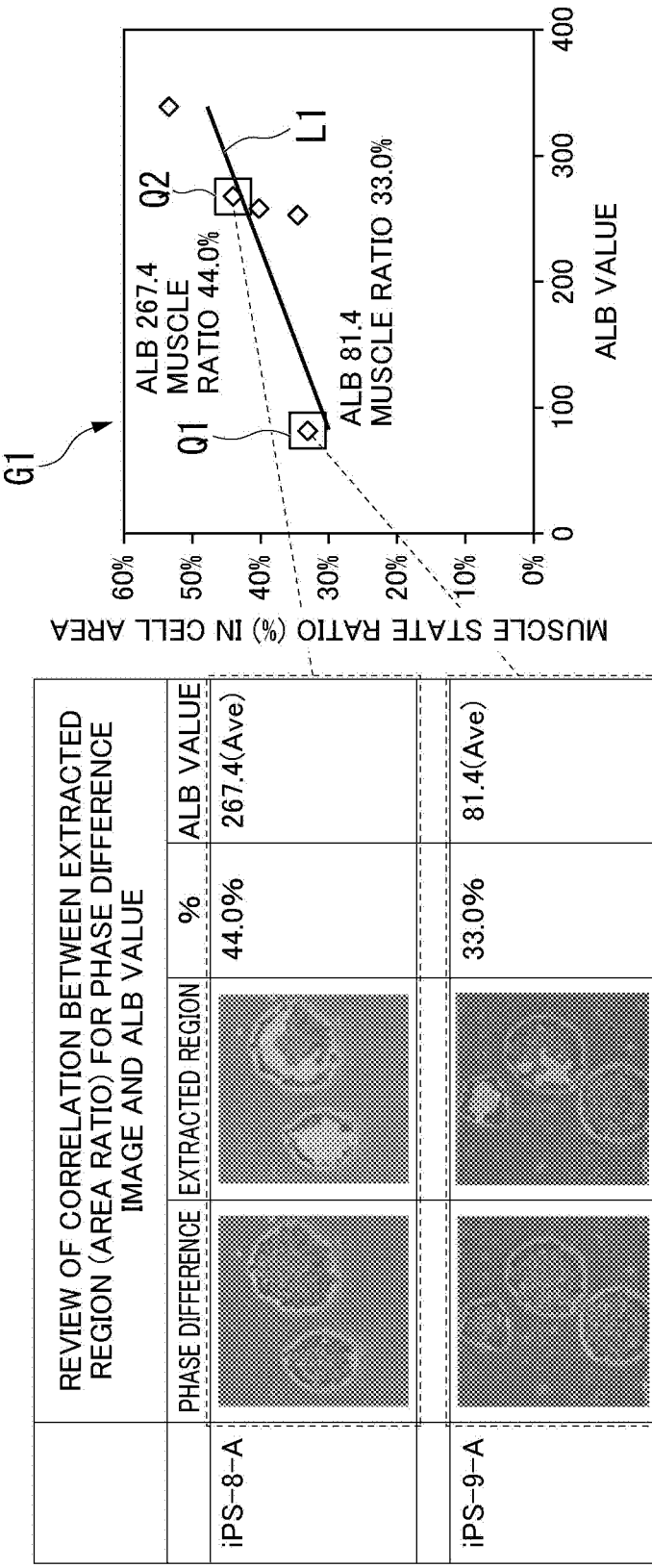
FIG. 40 is a diagram showing an example of a relationship between the muscle region and an amount of albumin.

Here, a relationship between a muscle region in the undifferentiated state maintaining culture process and an amount of albumin (ALB) in the differentiation-inducing process will be described with reference to FIG. 40. FIG. 40 is a diagram showing an example of the relationship between the muscle region and the amount of albumin. A graph G1 is a graph showing a ratio of the muscle region to the cell area in the undifferentiated state maintaining culture process with respect to the amount of albumin in the differentiation-inducing process. The amount of albumin is calculated in units of wells in which cells are cultured.

A point Q2 indicates a ratio of the muscle region to the cell area with respect to cells contained in a well having an albumin amount of 267.4 and this ratio is 44.0%. A point Q1 indicates a ratio of the muscle region to the cell area with respect to cells contained in a well having an albumin amount of 81.4, and this ratio is 33.0%. In the graph G1, a straight line L1 showing a result of fitting a plurality of points indicating the ratio of the muscle region to the cell area with respect to the albumin amount by a straight line is shown.

As shown in the graph G1, the expression level of albumin in the differentiation-inducing process after the undifferentiated state maintaining culture process increases as the ratio of a muscle region to a cell area in the undifferentiated state maintaining culture process increases and the correlation between the two can be confirmed. Also, the correlation coefficient of the entire sample was 0.79.

In addition to the above-described evaluation index (the area of the muscle region in the undifferentiated state maintaining culture process), an index value indicating the cell adhesion state in the undifferentiated state maintaining culture process may be used for the evaluation index used for determining the quality of cell differentiation. Therefore, the index value based on the result of determining the quality of differentiation in the time-lapse image before cells form the paving stone region includes an index value indicating the area of the muscle region in the time-lapse image in a process in which the cells are maintained and cultured in an undifferentiated state or an index value indicating the cell adhesion state.

Also, the evaluation index used for determining the quality of cell differentiation is not limited to the eight evaluation indices including the above-described evaluation index (the area of the muscle region in the undifferentiated state maintaining culture process) and existing evaluation indices may be used.

Also, as the threshold value of each evaluation index used for determining the quality of cell differentiation, statistics of indices of a plurality of images P related to a series of culture processes stored in the storage unit 301 may be used and statistics of index values of a plurality of images P for which the observer determines that the quality of cell differentiation is high among images P stores in the storage unit 301 may be used.

That is, statistics for a plurality of first indices calculated using a plurality of first evaluation indices acquired from each of the plurality of images P may be used as the first index. Here, the plurality of images P may be images in which a result of evaluating the differentiation of an evaluation target cell indicates that the quality of the differentiation is evaluated as high.

Also, in the cell evaluation method for use in the image determination device 10 according to the above-described embodiment, the first evaluation index includes any one of:
(a) a luminance value of a region containing paving stone-shaped cells;
(b) an area in which the comparative target cells adhere to a culture vessel;
(c) an area in which the comparative target cells are densely packed in the culture vessel;
(d) an area of a region where there are no comparative target cells;
(e) an area of dying cells or dead cells among the comparative target cells; and
(f) a ratio of a perimeter of a cell of the comparative target cells to an area of the cell.

Also, the first index includes a value of the area of the muscle region and/or an index value indicating the cell adhesion state in the process of maintaining and culturing the cells in an undifferentiated state.

In another example, the first index is a value of the area of the cell boundary region.

Also, each part provided in the image determination device 10 in the above-described embodiment may be implemented by dedicated hardware or may be implemented by a memory and a microprocessor.

Also, each part of the image determination device 10 includes a memory and a CPU and its function may be implemented by loading a program for implementing the function of each part of the image determination device 10 into the memory and executing the program.

Also, a process is performed by recording a program for implementing the functions of the parts provided in the image determination device 10 on a computer-readable recording medium and causing a computer system to read and execute the program recorded on the recording medium. Also, the "computer system" used here may include an operating system (OS) and hardware such as peripheral devices.

Also, the "computer system" is assumed to include a homepage providing environment (or displaying environment) when a World Wide Web (WWW) system is used.

Also, the "computer-readable recording medium" refers to a storage device such as a flexible disc, a magneto-optical disc, a ROM, a portable medium such as a compact disc-ROM (CD-ROM), and a hard disk embedded in the computer system. Further, the "computer-readable recording medium" is assumed to include a computer-readable recording medium for dynamically retaining the program for a short period of time as in a communication line when the program is transmitted via a network such as the Internet or a communication circuit such as a telephone circuit and a computer-readable recording medium for retaining the program for a given period of time as in a volatile memory inside the computer system including a server and a client when the program is transmitted. Also, the above-described program may be a program for implementing some of the above-described functions. Further, the above-described program may be a program capable of implementing the above-described function in combination with a program already recorded on the computer system.

REFERENCE SIGNS LIST

10 Image determination device
110 Acquisition unit
130 Non-adhesion ratio-specific arithmetic unit
140 Area-specific arithmetic unit
150 Density-specific arithmetic unit
131 Non-adhesion area calculation unit
141 Area calculation unit
151 Area/perimeter calculation unit
132 Non-adhesion ratio calculation unit
142 Average area calculation unit
152 Density calculation unit
133 Non-adhesion ratio determination unit
143 Area determination unit
153 Density determination unit

The invention claimed is:

1. A cell evaluation method for evaluating cell differentiation in a culture process including a cell differentiation-inducing process of stem cells in an undifferentiated state into mature somatic cells, the cell evaluation method comprising:
acquiring a first evaluation index which is a feature acquired from an image in which comparative target cells in the culture process are imaged and a first index calculated using the first evaluation index;
calculating, on the basis of the first evaluation index, a second index which is a feature acquired from an image in which evaluation target cells different from the comparative target cells are imaged; and
evaluating differentiation of the evaluation target cells by comparing the first index with the second index on the basis of a correlation between a value of an area of a muscle region of the stem cells in an undifferentiated state and an amount of the substance produced by the mature somatic cells, wherein
the first index includes the value of an area of a muscle region in a process of maintaining and culturing the cells in an undifferentiated state.

2. The cell evaluation method according to claim 1, wherein the first evaluation index is acquired from a plurality of images associated with elapsed time from a start of the culture process and a result of determining quality of the differentiation.

3. The cell evaluation method according to claim 2, wherein statistics for a plurality of first indices calculated using a plurality of first evaluation indices acquired from the plurality of images are used as the first index.

4. The cell evaluation method according to claim 3, wherein the plurality of images are images in which a result of evaluating the differentiation of the evaluation target cells indicates that the quality of the differentiation is evaluated as high.

5. The cell evaluation method according to claim 1, wherein the first evaluation index includes any one of:
(a) a luminance value of a region containing paving stone-shaped cells;
(b) an area in which the comparative target cells adhere to a culture vessel;

(c) an area in which the comparative target cells are densely packed in the culture vessel;

(d) an area of a region where there are no comparative target cells;

(e) an area of dying cells or dead cells among the comparative target cells; and (f) a ratio of a perimeter of a cell of the comparative target cells to an area of the cell.

6. The cell evaluation method according to claim 1, wherein the first index includes the value of an area of a muscle region and an index value indicating an adhesion state of the cells in the process of maintaining and culturing the cells in an undifferentiated state.

7. The cell evaluation method according to claim 1, wherein the first index is a value of an area of a cell boundary region.

8. The cell evaluation method according to claim 1, wherein, when a magnitude relationship between the second index and the first index has changed, a second evaluation index and a third index calculated using the second evaluation index are acquired with respect to the comparative target cells, and wherein the differentiation of the evaluation target cells is evaluated by calculating a fourth index calculated using the second evaluation index with respect to the evaluation target cells and comparing the third index with the fourth index.

9. The cell evaluation method according to claim 1, wherein the culture process includes a plurality of processes and the first evaluation index according to the process is acquired.

10. The cell evaluation method according to claim 1, wherein the first evaluation index based on elapsed time from a start of the culture process is acquired.

11. The cell evaluation method according to claim 1, wherein the cells are cells that differentiate into mature cells, and wherein the mature cells are mature epithelial cells.

12. The cell evaluation method according to claim 11, wherein the mature epithelial cells are mature hepatocytes.

13. A cell evaluation system for evaluating cell differentiation in a culture process including a cell differentiation-inducing process of stem cells in an undifferentiated state into mature somatic cells, the cell evaluation system comprising:

an acquisition unit configured to acquire a first evaluation index which is a feature acquired from an image in which comparative target cells in the culture process are imaged and a first index calculated using the first evaluation index;

a calculation unit configured to calculate, on the basis of the first evaluation index, a second index which is a feature acquired from an image in which evaluation target cells different from the comparative target cells are imaged; and an evaluation unit configured to evaluate differentiation of the evaluation target cells by comparing the first index with the second index on the basis of a correlation between a value of an area of a muscle region of the stem cells in an undifferentiated state and an amount of substance produced by the mature somatic cells, wherein the first index includes the value of an area of a muscle region in a process of maintaining and culturing the cells in an undifferentiated state.

14. A non-transitory computer readable storage medium storing a program for evaluating cell differentiation in a culture process including a cell differentiation-inducing process of stem cells in an undifferentiated state into mature somatic cells, the program causing a computer to execute processing comprising:

acquiring a first evaluation index which is a feature acquired from an image in which comparative target cells in the culture process are imaged and a first index calculated using the first evaluation index;

calculating, on the basis of the first evaluation index, a second index which is a feature acquired from an image in which evaluation target cells different from the comparative target cells are imaged; and evaluating differentiation of the evaluation target cells by comparing the first index with the second index on the basis of a correlation between a value of an area of a muscle region of the stem cells in an undifferentiated state and an amount of substance produced by the mature somatic cells, wherein the first index includes the value of an area of a muscle region in a process of maintaining and culturing the cells in an undifferentiated state.

* * * * *